(12) United States Patent
Chu et al.

(10) Patent No.: US 9,358,300 B2
(45) Date of Patent: *Jun. 7, 2016

(54) TRANSFECTION REAGENTS

(71) Applicant: LIFE TECHNOLOGIES CORPORATION, Carlsbad, CA (US)

(72) Inventors: Yongliang Chu, Rockville, MD (US); Malek Masoud, Gaithersburg, MD (US); Gulilat Gebeyehu, Potomac, MD (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/336,887

(22) Filed: Jul. 21, 2014

(65) Prior Publication Data

US 2015/0190522 A1  Jul. 9, 2015

Related U.S. Application Data

(63) Continuation of application No. 13/420,091, filed on Mar. 14, 2012, now Pat. No. 8,785,200, which is a continuation of application No. 12/353,371, filed on Jan. 14, 2009, now Pat. No. 8,158,827, which is a (Continued)

(51) Int. Cl.
A61K 47/48 (2006.01)
A61K 9/16 (2006.01)
(Continued)

(52) U.S. Cl.
CPC .............. *A61K 47/48046* (2013.01); *A61K 9/16* (2013.01); *A61K 31/14* (2013.01); *A61K 38/28* (2013.01); *A61K 38/40* (2013.01); *C07C 211/21* (2013.01); *C07C 211/63* (2013.01);
(Continued)

(58) Field of Classification Search
None
See application file for complete search history.

(56) References Cited

U.S. PATENT DOCUMENTS 2,046,720 A   7/1936  Bottoms
2,654,785 A  10/1953  Miescher et al.

(Continued)

FOREIGN PATENT DOCUMENTS

AU  2652692   5/1993
AU   158967  10/1997

(Continued)

OTHER PUBLICATIONS

Database Registry on STN; Eythylenediamine, registry No. 107-15-3; entered database, Nov. 1984.
"Transfection Reagent", *Genetic Engineering News*, col. 4, Jun. 15, 1993, 12 pages.
1993/07262; "Derwent WPI English language abstract for WO 93/07262 A2", Dialog File 351, Accession No. 9417386 (Document AL7), 1993.
Ahmed, O.A. et al., "N4,N9-dioleoyl spermine is a novel nonviral lipopolyamine vector for plasmid DNA formulation", *Pharmaceutical Research*, vol. 22, No. 6, Jun. 8, 2005, pp. 972-980.
Ahmed, O.A. et al., "Varying the Unsaturation in N4,N9-Dioctadecanoyl Spermines: Nonviral Lipopolyamine Vectors for More Efficient Plasmid DNA Formulation", *Pharmaceutical Research*, vol. 23, No. 1, Jan. 2006, pp. 31-40.
Albarella, J. P. et al., "Monoadduct forming photochemical reagents for labeling nucleic acids for hybridization", *Chemical Abstracts*, vol. 111, Abstract No. 130176h, American Chemical Society, 1989, 385-386.

(Continued)

*Primary Examiner* — Brian J Davis

(57) ABSTRACT

Disclosed are compounds capable of facilitating transport of biologically active agents or substances into cells having the general structure:

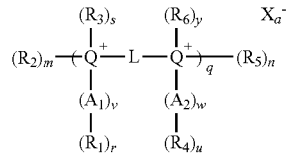

wherein Q is selected from the group consisting of N, O and S; L is any bivalent organic radical capable of linking each Q, such as C, CH, $(CH_2)_i$, or $\{(CH_2)_i-Y-(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $-X_1-L'-X_2-Z$ or $-Z$; $R_1$ $R_6$, independently of one another, are selected from the group consisting of H, $-(CH_2)_p$-D-Z, an alkyl, an alkenyl, an aryl, and an alkyl or alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and wherein at least one of $R_1$, $R_3$, $R_4$ and $R_6$ is a straight chain or branched, cyclic, alkyl, alkenyl, alkynyl or aryl group; and anyone of $R_1$, $R_3$, $R_4$ and/or $R_6$ may optionally be covalently linked with each other, with Y or with L when L is C or CH to form a cyclic moiety; Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, peptide, and protein; $X_1$ and $X_2$, independently of one another, are selected from the group consisting of NH, O, S, alkylene, and arylene; L' is selected from the group consisting of alkylene, alkenylene, alkynylene, arylene, alkylene ether, and polyether; D is Q or a bond; $A_1$ and $A_2$, independently of one another, are selected from the group consisting of $CH_2O$, $CH_2S$, $CH_2NH$, $C(O)$, $C(NH)$, $C(S)$ and $(CH_2)t$; X is a physiologically acceptable anion; m, n, r, s, u, v, w and y are 0 or 1, with the proviso that when both m and n are 0 at least one of r, s, u and y is other than 0; i, j, k, l, p and are integers from 0 to about 100; q is an integer from 1 to about 1000; and a is the number of positive charge divided by the valence of the anion.

28 Claims, 4 Drawing Sheets

Related U.S. Application Data continuation of application No. 11/040,687, filed on Jan. 21, 2005, now Pat. No. 7,479,573, which is a continuation of application No. 09/438,365, filed on Nov. 12, 1999, now Pat. No. 7,166,745.

(60) Provisional application No. 60/108,117, filed on Nov. 12, 1998.

(51) Int. Cl.

| | | |
|---|---|---|
| *A61K 38/40* | (2006.01) | |
| *A61K 38/28* | (2006.01) | |
| *C07C 211/64* | (2006.01) | |
| *A61K 31/14* | (2006.01) | |
| *C07C 211/63* | (2006.01) | |
| *C07C 211/21* | (2006.01) | |
| *C07C 229/26* | (2006.01) | |
| *C07D 209/48* | (2006.01) | |
| *C12N 15/88* | (2006.01) | |
| *C07D 241/12* | (2006.01) | |

(52) U.S. Cl.
CPC ............. *C07C211/64* (2013.01); *C07C 229/26* (2013.01); *C07D 209/48* (2013.01); *C07D 241/12* (2013.01); *C12N 15/88* (2013.01); *Y10S 435/81* (2013.01)

(56) References Cited

U.S. PATENT DOCUMENTS

| | | |
|---|---|---|
| 2,695,314 A | 11/1954 | Kusmln |
| 2,867,665 A | 1/1959 | Dornfeld |
| 2,901,461 A | 8/1959 | Auerbach et al. |
| 2,933,529 A | 4/1960 | Jesse |
| 3,152,188 A | 10/1964 | Kirkpatrick et al. |
| 3,324,182 A | 6/1967 | DeBrunner et al. |
| 3,369,905 A | 2/1968 | Jones et al. |
| 4,143,003 A | 3/1979 | Haas et al. |
| 4,235,871 A | 11/1980 | Papahadjopoulos et al. |
| 4,501,728 A | 2/1985 | Geho et al. |
| 4,625,064 A | 11/1986 | Kumoi et al. |
| 4,683,195 A | 7/1987 | Mullis et al. |
| 4,683,202 A | 7/1987 | Mullis |
| 4,737,323 A | 4/1988 | Martin et al. |
| 4,767,699 A | 8/1988 | Vary et al. |
| 4,800,159 A | 1/1989 | Mullis et al. |
| 4,812,449 A | 3/1989 | Rideout |
| 4,837,028 A | 6/1989 | Allen |
| 4,889,818 A | 12/1989 | Gelfand et al. |
| 4,889,953 A | 12/1989 | Inoue et al. |
| 4,897,355 A | 1/1990 | Eppstein et al. |
| 4,946,787 A | 8/1990 | Eppstein et al. |
| 4,959,217 A | 9/1990 | Sanders et al. |
| 4,962,022 A | 10/1990 | Fleming et al. |
| 4,965,188 A | 10/1990 | Mullis et al. |
| 4,967,008 A | 10/1990 | Friedli et al. |
| 5,047,342 A | 9/1991 | Chatterjee |
| 5,049,386 A | 9/1991 | Eppstein et al. |
| 5,079,352 A | 1/1992 | Gelfand et al. |
| 5,091,576 A | 2/1992 | Bergeron |
| 5,165,925 A | 11/1992 | Leong |
| 5,166,320 A | 11/1992 | Wu et al. |
| 5,171,678 A | 12/1992 | Behr et al. |
| 5,186,923 A | 2/1993 | Piwnica-Worms et al. |
| 5,187,085 A | 2/1993 | Lee |
| 5,196,135 A | 3/1993 | Merianos |
| 5,198,423 A | 3/1993 | Taguchi et al. |
| 5,208,036 A | 5/1993 | Eppstein et al. |
| 5,242,684 A | 9/1993 | Merianos |
| 5,244,797 A | 9/1993 | Kotewicz et al. |
| 5,264,423 A | 11/1993 | Cohen et al. |
| 5,264,618 A | 11/1993 | Felgner et al. |
| 5,266,106 A | 11/1993 | Breton |
| 5,270,179 A | 12/1993 | Chatterjee |
| 5,276,019 A | 1/1994 | Cohen et al. |
| 5,277,897 A | 1/1994 | Piwnica-Worms et al. |
| 5,279,833 A | 1/1994 | Rose |
| 5,283,185 A | 2/1994 | Epand et al. |
| 5,286,717 A | 2/1994 | Cohen et al. |
| 5,328,470 A | 7/1994 | Nabel et al. |
| 5,328,984 A | 7/1994 | Pastan et al. |
| 5,334,761 A | 8/1994 | Gebeyehu et al. |
| 5,338,532 A | 8/1994 | Tomalia et al. |
| 5,350,672 A | 9/1994 | Oberst et al. |
| 5,354,844 A | 10/1994 | Beug et al. |
| 5,374,553 A | 12/1994 | Gelfand et al. |
| 5,401,084 A | 3/1995 | Volz et al. |
| 5,409,818 A | 4/1995 | Davey et al. |
| 5,436,149 A | 7/1995 | Barnes |
| 5,455,166 A | 10/1995 | Walker |
| 5,455,335 A | 10/1995 | Kahne et al. |
| 5,459,127 A | 10/1995 | Felgner et al. |
| 5,484,702 A | 1/1996 | Ludwig |
| 5,498,522 A | 3/1996 | Porter |
| 5,498,523 A | 3/1996 | Tabor et al. |
| 5,500,356 A | 3/1996 | Li et al. |
| 5,506,212 A | 4/1996 | Hoke et al. |
| 5,510,239 A | 4/1996 | Baracchini, Jr. et al. |
| 5,510,476 A | 4/1996 | Ravikumar et al. |
| 5,512,438 A | 4/1996 | Ecker |
| 5,512,462 A | 4/1996 | Cheng |
| 5,514,577 A | 5/1996 | Draper et al. |
| 5,514,787 A | 5/1996 | Atkinson |
| 5,519,134 A | 5/1996 | Acevedo et al. |
| 5,521,291 A | 5/1996 | Curiel et al. |
| 5,521,302 A | 5/1996 | Cook |
| 5,527,524 A | 6/1996 | Tomalia et al. |
| 5,527,928 A | 6/1996 | Nantz et al. |
| 5,532,142 A | 7/1996 | Johnston et al. |
| 5,541,307 A | 7/1996 | Cook et al. |
| 5,543,507 A | 8/1996 | Cook et al. |
| 5,545,412 A | 8/1996 | Eppstein et al. |
| 5,545,540 A | 8/1996 | Mian |
| 5,547,932 A | 8/1996 | Curiel et al. |
| 5,550,289 A | 8/1996 | Eppstein et al. |
| 5,554,746 A | 9/1996 | Ravikumar et al. |
| 5,560,929 A | 10/1996 | Hedstrand et al. |
| 5,574,142 A | 11/1996 | Meyer et al. |
| 5,578,475 A | 11/1996 | Jessee |
| 5,580,859 A | 12/1996 | Felgner et al. |
| 5,583,198 A | 12/1996 | Whittaker |
| 5,587,441 A | 12/1996 | Frechet et al. |
| 5,587,446 A | 12/1996 | Frechet et al. |
| 5,588,718 A | 12/1996 | Winner et al. |
| 5,589,392 A | 12/1996 | Short |
| 5,589,466 A | 12/1996 | Felgner et al. |
| 5,595,096 A | 1/1997 | Coffman |
| 5,595,897 A | 1/1997 | Midoux et al. |
| 5,596,091 A | 1/1997 | Switzer |
| 5,602,240 A | 2/1997 | De Mesmaeker et al. |
| 5,614,365 A | 3/1997 | Tabor et al. |
| 5,621,730 A | 4/1997 | Kelley et al. |
| 5,627,159 A | 5/1997 | Shih et al. |
| 5,631,329 A | 5/1997 | Yin et al. |
| 5,635,487 A | 6/1997 | Wolff et al. |
| 5,641,662 A | 6/1997 | Debs et al. |
| 5,650,096 A | 7/1997 | Harris et al. |
| 5,658,776 A | 8/1997 | Flotte et al. |
| 5,661,025 A | 8/1997 | Szoka et al. |
| 5,667,774 A | 9/1997 | Figuly |
| 5,670,347 A | 9/1997 | Gopal |
| 5,674,908 A | 10/1997 | Haces et al. |
| 5,676,954 A | 10/1997 | Brigham |
| 5,681,944 A | 10/1997 | Crooke et al. |
| 5,691,460 A | 11/1997 | Duvic et al. |
| 5,693,509 A | 12/1997 | Cotten et al. |
| 5,693,773 A | 12/1997 | Kandimalla et al. |
| 5,703,055 A | 12/1997 | Felgner et al. |
| 5,705,385 A | 1/1998 | Bally et al. |
| 5,714,166 A | 2/1998 | Tomalia et al. |
| 5,719,131 A | 2/1998 | Harris et al. |
| 5,726,298 A | 3/1998 | Hirai et al. |

(56) References Cited

U.S. PATENT DOCUMENTS

| | | |
|---|---|---|
| 5,736,387 A | 4/1998 | Paul et al. |
| 5,736,392 A | 4/1998 | Hawley-Nelson et al. |
| 5,744,335 A | 4/1998 | Wolff et al. |
| 5,744,625 A | 4/1998 | Nantz et al. |
| 5,753,613 A | 5/1998 | Ansell et al. |
| 5,756,353 A | 5/1998 | Debs |
| 5,759,778 A | 6/1998 | Li et al. |
| 5,759,805 A | 6/1998 | Feldhaus et al. |
| 5,773,527 A | 6/1998 | Tomalia et al. |
| 5,780,053 A | 7/1998 | Ashley et al. |
| 5,783,565 A | 7/1998 | Lee et al. |
| 5,783,566 A | 7/1998 | Mislick |
| 5,785,992 A | 7/1998 | Ansell et al. |
| 5,795,587 A | 8/1998 | Gao et al. |
| 5,807,746 A | 9/1998 | Lin et al. |
| 5,824,812 A | 10/1998 | Nantz et al. |
| 5,827,703 A | 10/1998 | Debs et al. |
| 5,830,430 A | 11/1998 | Unger et al. |
| 5,830,878 A | 11/1998 | Gorman et al. |
| 5,834,439 A | 11/1998 | Haces et al. |
| 5,837,092 A | 11/1998 | Grieves et al. |
| 5,837,283 A | 11/1998 | McDonald et al. |
| 5,837,533 A | 11/1998 | Boutin |
| 5,840,710 A | 11/1998 | Lee et al. |
| 5,854,224 A | 12/1998 | Lockett et al. |
| 5,861,397 A | 1/1999 | Wheeler |
| 5,866,613 A | 2/1999 | Bergeron |
| 5,869,606 A | 2/1999 | Whittaker |
| 5,869,715 A | 2/1999 | Nantz et al. |
| 5,871,929 A | 2/1999 | Barnes |
| 5,877,309 A | 3/1999 | McKay et al. |
| 5,885,970 A | 3/1999 | Bennett et al. |
| 5,886,165 A | 3/1999 | Kandimalla et al. |
| 5,892,071 A | 4/1999 | Nantz et al. |
| 5,906,922 A | 5/1999 | Whittaker et al. |
| 5,908,635 A | 6/1999 | Thierry |
| 5,908,777 A | 6/1999 | Lee et al. |
| 5,916,807 A | 6/1999 | Bennett et al. |
| 5,919,772 A | 7/1999 | Szyf et al. |
| 5,925,623 A | 7/1999 | Nantz et al. |
| 5,929,226 A | 7/1999 | Padmapriya et al. |
| 5,935,936 A | 8/1999 | Fasbender et al. |
| 5,948,614 A | 9/1999 | Chatterjee |
| 5,948,767 A | 9/1999 | Scheule et al. |
| 5,948,925 A | 9/1999 | Keynes et al. |
| 5,962,533 A | 10/1999 | Bergeron, Jr. |
| 5,976,567 A | 11/1999 | Wheeler et al. |
| 5,977,084 A | 11/1999 | Szoka, Jr. et al. |
| 5,977,306 A | 11/1999 | Grieve et al. |
| 5,985,558 A | 11/1999 | Dean et al. |
| 6,013,448 A | 1/2000 | Braxton et al. |
| 6,017,735 A | 1/2000 | O'Hare et al. |
| 6,020,202 A | 2/2000 | Jessee |
| 6,022,874 A | 2/2000 | Wheeler |
| 6,022,950 A | 2/2000 | Murphy |
| 6,030,626 A | 2/2000 | Kolattukudy et al. |
| 6,031,086 A | 2/2000 | Switzer |
| 6,034,137 A | 3/2000 | Belloni et al. |
| 6,043,339 A | 3/2000 | Lin et al. |
| 6,051,429 A | 4/2000 | Hawley-Nelson et al. |
| 6,054,439 A | 4/2000 | Szyf et al. |
| 6,056,938 A | 5/2000 | Unger et al. |
| 6,074,826 A | 6/2000 | Hogan et al. |
| 6,075,012 A | 6/2000 | Gebeyehu et al. |
| 6,086,913 A | 7/2000 | Tam et al. |
| 6,090,627 A | 7/2000 | Kemp et al. |
| 6,093,564 A | 7/2000 | Budowsky |
| 6,103,492 A | 8/2000 | Yu |
| 6,110,662 A | 8/2000 | Foung et al. |
| 6,110,916 A | 8/2000 | Haces et al. |
| 6,126,965 A | 10/2000 | Kasid et al. |
| 6,180,784 B1 | 1/2001 | Wolff et al. |
| 6,211,140 B1 | 4/2001 | Sivik et al. |
| 6,214,804 B1 | 4/2001 | Felgner et al. |
| 6,251,390 B1 | 6/2001 | Harman et al. |
| 6,287,817 B1 | 9/2001 | Davis et al. |
| 6,333,433 B1 | 12/2001 | Banerjee et al. |
| 6,335,199 B1 | 1/2002 | Bischoff et al. |
| 6,346,516 B1 | 2/2002 | Banerjee et al. |
| 6,350,796 B1 | 2/2002 | Dworak et al. |
| 6,376,248 B1 | 4/2002 | Hawley-Nelson et al. |
| 6,387,395 B1 | 5/2002 | Eppstein et al. |
| 6,399,663 B1 | 6/2002 | Haces et al. |
| 6,495,518 B1 | 12/2002 | Hawiger et al. |
| 6,503,945 B2 | 1/2003 | Banerjee et al. |
| 6,521,455 B2 | 2/2003 | O'Hare et al. |
| 6,541,649 B2 | 4/2003 | Banerjee et al. |
| 6,716,882 B2 | 4/2004 | Haces et al. |
| 6,733,777 B2 | 5/2004 | Erbacher et al. |
| 6,773,920 B1 | 8/2004 | Dalby et al. |
| 6,890,554 B2 | 5/2005 | Jessee et al. |
| 6,989,434 B1 | 1/2006 | Gebeyehu et al. |
| 7,074,556 B2 | 7/2006 | Li et al. |
| 7,145,039 B2 * | 12/2006 | Chu et al. ............. 564/503 |
| 7,166,298 B2 | 1/2007 | Jessee et al. |
| 7,166,745 B1 | 1/2007 | Chu et al. |
| 7,173,154 B2 | 2/2007 | Chu et al. |
| 7,323,594 B2 | 1/2008 | Chu et al. |
| 7,470,817 B2 * | 12/2008 | Chu et al. ............. 564/506 |
| 7,479,573 B2 | 1/2009 | Chu et al. |
| 7,531,676 B2 | 5/2009 | Eaton et al. |
| 7,601,872 B2 | 10/2009 | Chu et al. |
| 7,915,450 B2 | 3/2011 | Chu et al. |
| 2002/0028447 A1 | 3/2002 | Li et al. |
| 2002/0039765 A1 | 4/2002 | O'Hare et al. |
| 2002/0062044 A1 | 5/2002 | Banerjee et al. |
| 2002/0062489 A1 | 5/2002 | Silver et al. |
| 2002/0077305 A1 | 6/2002 | Jessee et al. |
| 2002/0086849 A1 | 7/2002 | Gebeyehu et al. |
| 2002/0106378 A1 | 8/2002 | O'Hare et al. |
| 2002/0156049 A1 | 10/2002 | Haces et al. |
| 2003/0069173 A1 | 4/2003 | Hawley-Nelson et al. |
| 2003/0144230 A1 | 7/2003 | Hawley-Nelson et al. |
| 2004/0152770 A1 | 8/2004 | Haces et al. |
| 2004/0176282 A1 | 9/2004 | Dalby et al. |
| 2005/0014962 A1 | 1/2005 | Gebeyehu et al. |
| 2005/0164391 A1 | 7/2005 | Chu et al. |
| 2005/0164971 A1 | 7/2005 | Chu et al. |
| 2005/0164972 A1 | 7/2005 | Chu et al. |
| 2005/0208657 A1 | 9/2005 | Dalby et al. |
| 2005/0260757 A1 | 11/2005 | Gebeyehu et al. |
| 2007/0202598 A1 | 8/2007 | Chu et al. |
| 2007/0202600 A1 | 8/2007 | Chu et al. |
| 2009/0143583 A1 | 6/2009 | Chu et al. |
| 2010/0159593 A1 | 6/2010 | Chu et al. |

FOREIGN PATENT DOCUMENTS

| | | |
|---|---|---|
| DE | 4411588 | 9/1995 |
| DE | 4411594 | 12/1995 |
| EP | 2046720 | 7/1936 |
| EP | 0000406 | 1/1979 |
| EP | 0168930 | 1/1986 |
| EP | 0187702 | 7/1986 |
| EP | 0329822 B1 | 8/1989 |
| EP | 0359347 | 3/1990 |
| EP | 0394111 | 10/1990 |
| EP | 0304111 | 10/1991 |
| EP | 0544292 | 6/1993 |
| EP | 0821059 | 1/1998 |
| EP | 0846680 | 6/1998 |
| EP | 0684315 B1 | 6/2002 |
| EP | 1275735 | 1/2003 |
| EP | 1187807 | 7/2007 |
| EP | 1829856 | 9/2007 |
| FR | 1146332 | 7/1915 |
| FR | 1567214 | 5/1969 |
| GB | 0823303 | 11/1959 |
| GB | 892413 | 3/1962 |
| GB | 901187 | 7/1962 |
| JP | 08509953 | 10/1996 |
| JP | 09509402 | 9/1997 |
| JP | 09510435 | 10/1997 |
| JP | 10152461 | 6/1998 |

(56) References Cited

FOREIGN PATENT DOCUMENTS

| | | |
|---|---|---|
| JP | 10510813 | 10/1998 |
| JP | 2001525419 | 12/2001 |
| WO | 87/02061 | 4/1987 |
| WO | 94/02499 | 2/1989 |
| WO | 90/09180 | 8/1990 |
| WO | 90/09786 | 9/1990 |
| WO | 90/11092 | 10/1990 |
| WO | 91/04668 | 4/1991 |
| WO | 91/04753 | 4/1991 |
| WO | 91/07947 | 6/1991 |
| WO | 91/08191 | 6/1991 |
| WO | 91/15501 | 10/1991 |
| WO | 91/16024 | 10/1991 |
| WO | 91/17424 | 11/1991 |
| WO | 92/06188 | 4/1992 |
| WO | 92/06200 | 4/1992 |
| WO | 92/13570 | 8/1992 |
| WO | 92/20697 | 11/1992 |
| WO | 92/21752 | 12/1992 |
| WO | 92/22635 A1 | 12/1992 |
| WO | 93/03709 | 3/1993 |
| WO | 93/05162 | 3/1993 |
| WO | 93/07282 | 4/1993 |
| WO | 93/07283 | 4/1993 |
| WO | 93/08130 | 4/1993 |
| WO | 93/14778 | 8/1993 |
| WO | 93/19768 | 10/1993 |
| WO | 94/02499 A1 | 2/1994 |
| WO | 94/04696 | 3/1994 |
| WO | 94/05624 | 3/1994 |
| WO | 94/07899 | 4/1994 |
| WO | 94/08004 | 4/1994 |
| WO | 94/14475 | 7/1994 |
| WO | 94/17093 | 8/1994 |
| WO | 94/23751 | 10/1994 |
| WO | 94/27433 A1 | 12/1994 |
| WO | 94/27435 | 12/1994 |
| WO | 95/02397 | 1/1995 |
| WO | 95/02698 | 1/1995 |
| WO | 95/16028 A1 | 6/1995 |
| WO | 95/16664 | 6/1995 |
| WO | 95/17373 | 6/1995 |
| WO | 95/20682 | 8/1995 |
| WO | 95/21259 | 8/1995 |
| WO | 95/24221 | 9/1995 |
| WO | 95/31557 | 11/1995 |
| WO | 96/01841 | 1/1996 |
| WO | 96/05218 | 2/1996 |
| WO | 96/08723 | 3/1996 |
| WO | 96/10038 | 4/1996 |
| WO | 96/10640 | 4/1996 |
| WO | 96/15811 | 5/1996 |
| WO | 96/18372 | 6/1996 |
| WO | 96/22321 A1 | 7/1996 |
| WO | 96/22765 | 8/1996 |
| WO | 96/26179 | 8/1996 |
| WO | 96/29337 | 9/1996 |
| WO | 96/31549 | 10/1996 |
| WO | 96/32474 | 10/1996 |
| WO | 96/35706 | 11/1996 |
| WO | 96/40961 | 12/1996 |
| WO | 97/02061 A1 | 1/1997 |
| WO | 97/05265 | 2/1997 |
| WO | 97/09451 | 3/1997 |
| WO | 97/42819 | 11/1997 |
| WO | 98/02190 | 1/1998 |
| WO | 98/06736 | 2/1998 |
| WO | 98/14439 | 4/1998 |
| WO | 98/19709 | 5/1998 |
| WO | 98/29541 | 7/1998 |
| WO | 98/32866 | 7/1998 |
| WO | 98/40499 | 9/1998 |
| WO | 98/40502 | 9/1998 |
| WO | 98/47912 | 10/1998 |
| WO | 99/02190 | 1/1999 |
| WO | 99/05302 | 2/1999 |
| WO | 99/11809 | 3/1999 |
| WO | 99/24559 | 5/1999 |
| WO | 99/29712 | 6/1999 |
| WO | 99/41410 | 8/1999 |
| WO | 99/46400 | 9/1999 |
| WO | 00/12454 | 3/2000 |
| WO | 00/27795 | 5/2000 |
| WO | 00/58488 | 10/2000 |
| WO | 00/64858 | 11/2000 |
| WO | 01/07548 | 2/2001 |
| WO | 02/34879 | 5/2002 |
| WO | 2004/063342 | 7/2004 |
| WO | 2004/105697 | 12/2004 |

OTHER PUBLICATIONS

Albrecht, T. et al., "Cationic lipide mediated transfer of c-abl and bcr antisense oligonucleotides to immature normal myeloid cells: Uptake, biological effects and modulation of gene expression", *Annals of Hematology*, vol. 72, Springer-Verlag, 1996, 73-79.

Aslanyan, V. M. et al., "Conformation and Thermal Stability of DNA in Aqueous Solutions of Beta-Alanine and gama-Aminobutyric Acid", *Biophysics*, 29 (4), Pergamon Press, Ltd.,, 1984, 615-620.

Asokan, Aravind et al., "Cytosolic Delivery of Macromolecules. 3. Synthesis and Characterization of Acid-Sensitive Bis-Detergents", *Bioconjugate Chemistry*, vol. 15, No. 6, 2004, 1166-1173.

Astatke, Mekbib et al., "How *E. coli* DNA Polymerase I (Klenow fragment) distinguishes between Deoxy-and Dideoxynucleotides", *The Journal of Molecular Biology,*, vol. 278, Academic Press Ltd.,, Apr. 1998, pp. 147-165.

Astatke, Mekbib et al., U.S. Appl. No. 09/570,526, filed May 12, 2000, 67 pages.

Aumailley, Monique et al., "Cell attachment properties of collagen type VI and Arg-Gly-Asp dependent binding to its alpha 2(VI) and alpha 3(VI) chains", *Experimental Cell Research*, vol. 181, No. 2, Apr. 1989, 463-474.

Balle, et al., Database CAPLUS on STN, Acc. No. 1936:19559 DE 624443 (Jan. 21, 1936) (abstract).

Baltzly, R. et al., "The Preparation of N-Mono-substituted and Unsymmetrically Disubstituted Piperazines", *Journal of the American Chemical Society*, vol. 66, Jan. 1, 1944, 263-266.

Banerjee, Rajkumar et al., "Design, Synthesis, and Transfection Biology of Novel Cationic Glycolipids for Use in Liposomal Gene Delivery", *Journal of Medicinal Chemistry*, vol. 44, No. 24, 2001, 4176-4185.

Banerjee, Rajkumar et al., "Novel Series of Non-Glycerol-Based Cationic Transfection Lipids for Use in Liposomal Gene Delivery", *Journal of Medicinal Chemistry*, vol. 42, No. 21, Oct. 1, 1999, 4292-4299.

Bangham, A. et al., "Diffusion of Univalent Ions Across the Lamellae of Swollen Phospholipids", *J. Mol. Biol. 13:*, 1965, 238-252.

Barefield, E K. et al., "Synthesis of Macrocyclic Tetramines by Metal Ion Assisted Cyclization Reactions", *Inorganic Chemistry*, vol. 15, No. 6, 1976, 1370-1377.

Barnes, , "The Fidelity of Taq Polymerase Catalyzing PCR is Improved by an N-Terminal Deletion", *Gene*, vol. 112, No. 1, Mar. 1, 1992, 29-35.

Barthel, Fabrice et al., "Laboratory Methods: Gene Transfer Optimization with Lipospermine-Coated DNA", *DNA and Cell Biology*, vol. 12, No. 6, Mary Ann Liebert, Inc., 1993, 553-560.

Baskaran, N. et al., "Uniform Amplification of a Mixture of Deoxyribonucleic Acids with Varying GC Content", *Genome Research*, vol. 6, 1996, 633-638.

Behr, Jean-Paul et al., "Efficient Gene Transfer Into Mammalian Primary Endocrine Cells with Lipopolyamine-Coated DNA", *Proceedings of the National Academy of Sciences (PNAS)*, vol. 86, Sep. 1989, 6982-6986.

Behr, Jean-Paul , "Gene Transfer with Synthetic Cationic Amphiphiles:Prospects for Gene Therapy", *Bioconjugate Chemistry*, vol. 5, No. 5, American Chemical Society, Sep. 1994, 382-389.

Behr, Jean-Paul , "Synthetic Gene-Transfer Vectors", *Accounts of Chemical Research*, vol. 26, No. 5, 1993, 274-278.

Belyaev, et al., "Nitrosoalkylureas with a quaternary nitrogen atom. 4. Synthesis of new nitrosoalkylureas based on bisquaternary

(56) References Cited

OTHER PUBLICATIONS ethylenediammonium salts", *Izvestiya Akademii Nauk SSSR, Seriya Khimicheskaya*, vol. 3, abstract, Acc. No. 1987:101731 CAPLUS, 1986, 610-13.

Bennett, C. F. et al., "Cationic lipids enhance cellular uptake and activity of phosphorothioate antisense oligonucleotides", *Molecular Pharmacology*, vol. 41, 1992, 1023-1033.

Bennett, Michael J. et al., "Cationic Lipid-Mediated Gene Delivery to Murine Lung: Correlation of Lipid Hydration with in Vivo Transfection Activity", *Journal of Medicinal Chemistry*, vol. 40, No. 25, 1997, 4069-4078.

Benoist, Christophe et al., "In vivo sequence requirements of the SV40 early promoter region", vol. 290, *Nature*, Mar. 26, 1981, 304-310.

Bergeron, R. J. et al., "Metabolically Programmed Polyamine Analogue Antidiarrheals", *J. Med. Chem.*, vol. 39, No. 13, 1996, 2461-2471.

Bielinska, Anna et al., "Regulation of in vitro gene expression using antisense oligonucleotides or antisense expression plasmids transfected using starburst PAMAM dendrimers", *Nucleic Acids Research*, vol. 24, No. 11, Jun. 1996, 2176-2182.

Blagbrough, I.S. et al., "Polyamines and novel polyamine conjugates interact with DNA in ways that can be exploited in non-viral gene therapy", *Biochemical Society Transactions*, Polyamines and Their Role in Human Disease, vol. 31, Part 2, 2003, pp. 397-406.

Boehme, et al., "Tertiary and quaternary salts of hexahydropyrimidines", *Justus Liebigs Annalen der Chemie*, vol. 723, Database CAPLUS on STN, Acc. No. 1969:430441, 1969, 41-46.

Bond, V. C. et al., "Poly-L-Ornithine-Mediated Transformation of Mammalian Cells", *Mol. Cell. Biol.*, vol. 7, No. 6, Jun. 1987, 2286-2293.

Bonfanti, Marina et al., "p21WAF1-derived Peptides Linked to an Internalization Peptide Inhibit Human Cancer Cell Growth", *Cancer Research*, vol. 57, No. 8, Apr. 15, 1997, 1442-1446.

Bonifaci, Neris et al., "Nuclear translocation of an exogenous fusion protein containing HIV Tat requires unfolding", *AIDS*, vol. 9, No. 9, Sep. 1995, 995-1000.

Bottger, M. et al., "Condensation of vector DNA by the chromosomal protein HMG1 results in efficient transfection", *Biochemica et Biophysica Acta*, vol. 950, No. 2, 1988, 221-228.

Boussif, Otmane et al., "A versatile vector for gene and oligonucleotide transfer into cells in culture and in vivo: polyethylenimine", *Proceedings of the National Academy of Sciences (PNAS)*, vol. 92, No. 16, Aug. 1, 1995, 7297-7301.

Braunlin, W. H. et al., "Equilibrium dialysis studies of polyamine binding to DNA", *Biopolymers*, vol. 21, No. 7, Jul. 1982, 1301-1314.

Brunette, Elisa et al., "Lipofection does not require the removal of serum" *Nucleic Acids Research*, vol. 20, No. 5, Mar. 11, 1992, 1151.

Buche, A. et al., "Effect of Organic Effectors on Chromatin Solubility, DNA-Histone H1 Interactions, DNA and Histone H1 Structures", *J. Biomol. Struct. & Dynam*, vol. 11, 1993, 95-119.

Buche, A. et al., "Glycine and other amino compounds prevent chromatin precipitation at physiological ionic strength", *FEBS Letters*, vol. 247, Federation of European of European Biochemical Societies and Elsevier Science Publishers B. V. (Biomedical Division), 1989, 367-370.

Buche, A. et al., "Organic Osmotic Effectors and Chromatin Structure", *J. Biomol. Struct. & Dynam*, vol. 8, Adenine Press, 1990, 301-618.

Budker, V. et al., "Protein/Amphipathic Polyamine Complexes Enable Highly Efficient Transfection with Minimal Toxicity", *Biotechniques*, vol. 23, No. 1, Jul. 1997, 139-147.

Butler, George B. et al., "Preparation and Polymerization of Unsaturated Quaternary Ammonium Compounds", *J. Am. Chem. Soc.*, vol. 71, No. 9, 1949, 3120-3122.

Caminati, Gabriella et al., "Photophysical Investigation of Starburst Dendrimers and Their Interactions with Anionic and Cationic Surfactants", *Journal of the American Chemical Society*, vol. 112, No. 23, Nov. 1990, 8515-8522.

Canovas, D. et al., "Isolation and Characterization of Salt-sensitive Mutants of the Moderate Halophile Halomonas elongate and Clonging of the Ectoine Synthesis Genes", *J. Biol. Chem.*, vol. 272, Oct. 1997, 25794-25801.

Canovas, D. et al., "Osmoprotectants in Halomonas elongate : High-Affinity Betaine Transport System and Choline-Betaine Pathway", *J. Bacteriol . 178:*, American Society for Microbiology, Dec. 1996, 7221-7226.

Carninci, Piero et al., "Thermostabilization and thermoactivation of thermolabile enzymes by trehalose and its application for the synthesis of full length cDNA,", *Proceedings of the National Academy of Sciences (PNAS)*, vol. 95, No. 2, Jan. 20, 1998, 520-524.

Carrasco, Luis et al., "Modification of membrane permeability in vaccinia virus-infected cells", *Virology*, vol. 117, No. 1, Feb. 1982, 62-69.

Carrasco, Luis , "Modification of membrane permeability induced by animal viruses early in infection", *Virology*, vol. 113, No. 2, Sep. 1981, 623-629.

Casapullo, A. et al., "Coriacenins: A New Class of Long Alkyl Chain Amino Alcohols from the Meditteranean Sponge *Clathrina coriacea*", *Journal of Organic Chemistry*, vol. 61, 1996, 7415-7419.

Chambers, S. T. et al., "Dimethylthetin Can Substitute for Glycine Betaine as an Osmoprotectant Molecule for *Escherichia coli*", *J. Bacteriol. 169:*, American Society for Microbiology, 1987, 4845-4847.

Chaney, W. G. et al., "High-Frequency Transfection of CHO Cells Using Polybrene", *Som. Cell Mol. Genet. 12(3):*, 1986, 237-244.

Chen, Xiaozhuo et al., "A self-initiating eukaryotic transient gene expression system based on contransfection of bacteriophage T7 RNA polymerase and DNA vectors containing a T7 autogene", *Nucleic Acids Research*, vol. 22, No. 11, Oxford University Press, Jun. 11, 1994, 2114-2120.

Ciccarone, V. et al., "Cationic Liposome-Mediated Transfection of Eukaryotic Cells: High Efficiency Nucleic Acid Delivery with Lipofectin, Lipofectace, Lipofectamine Reagents.", *The FASEB Journal*, vol. 7, No. 7, Abstract No. 454, Abstracts, Federation of American Societies for Experimental Biology, 1993, A1131.

Ciccarone, Valentina et al., "DMRIE-C reagent for transfection of suspension cells and for RNA transfections", *Focus*, vol. 17, No. 3, Sep. 1995, 84-87.

Citovsky, Vitaly et al., "Nuclear localization of Agrobacterium VirE2 protein in plant cells", *Science*, vol. 256, No. 5056, American Association for the Advancement of Science, Jun. 26, 1992, 1802-1805.

Cohen, J. , "Naked DNA points way to vaccines", *Science*, vol. 259, 1993, 1691-1692.

Cotten, Matt et al., "High-Efficiency Receptor-Mediated Delivery of Small and Large (48 Kilobase Gene Constructs Using the Endosome-Disruption Activity of Defective or Chemically Inactivated Adenovirus Particles", vol. 89, *Proceedings of the National Academy of Sciences (PNAS)*, The National Academy of Sciences, Jul. 1992, 6094-6098.

Cotten, Matt et al., "Non-viral approaches to gene therapy", *Current Opinion in Biotechnology*, vol. 4, No. 6, Dec. 1993, 705-710.

Cotten, Matt et al., "Transferrin-Polycation-Mediated Introduction of DNA into Human Leukemic Cells: Stimulation by Agents that Affect the Survival of Transfected DNA or Modulate Transferrin Receptor Levels", *Proceedings of the National Academy of Sciences (PNAS)*, vol. 87, No. 11, National Academy Press, Jun. 1, 1990, 4033-4037.

Curiel, David T. et al., "Adenovirus enhancement of transferrin-polylysine-mediated gene delivery", vol. 88, *Proceedings of the National Academy of Sciences (PNAS)*, Oct. 1991, 8850-8854.

Curiel, David T. et al., "Gene Transfer to Respiratory Epithelial Cells via the Receptor-mediated Endocytosis Pathway", *American Journal of Respiratory Cell and Molecular Biology*, vol. 6, American Thoracic Society, 1992, 247-252.

Curiel, David T. et al., "High-efficiency gene transfer mediated by adenovirus coupled to DNA-polylysine complexes", *Human Gene Therapy*, vol. 3, No. 2, Apr. 1992, 147-154.

Dattagupta, N. et al., "Photochemical nucleic acid-labeling reagent having a polyalkylamine spacer", *Chemical Abstracts 114:*, Abstract No. 114: 78227w, American Chemical Society, 1991, 383.

(56) References Cited

OTHER PUBLICATIONS

Dayhoff, Margaret O. et al., "A Model of Evolutionary Change in Proteins", *Chapter 22, Atlas of Protein Sequence and Structure*, vol. 5, Supplement 3, National Biomedical Research Foundation, 1978, 345-352.
DE 44 11 588 C1; "Derwent WPI English language abstract for DE 44 11 588 C1", (Document AN14), Dialog File 351, Accession No. 10428036, 1995.
DE 44 11 594 C1; "Derwent WPI English language abstract for DE 44 11 594 C1", (Document AP14), Dialog File 351, Accession No. 10524091, 1995.
De Robertis, E. M. et al., "Intracellular migration of nuclear proteins in Xenopus oocytes", *Nature*, vol. 272, Mar. 16, 1978, 254-256.
Deamer, D. W. et al., "Liposome Preparation: Methods and Mechanisms", in *Liposomes*, Marc J. Ostro, ed., Marcel Dekker, Inc. NY, 1983, 27-51.
Dean, Nicholas M. et al., "Inhibition of protein kinase C-alpha expression in mice after systemic administration of phosphorothioate antisense oligodeoxynucleotides", *Proceedings of the National Academy of Sciences (PNAS)*, vol. 91, No. 24, National Academy Press, Nov. 22, 1994, 11762-11766.
Dedhar, Shoukat et al., "A cell surface receptor complex for collagen type I recognizes the Arg-Gly-Asp sequence", *Journal of Cell Biology*, vol. 104, No. 3, Mar. 1, 1987, 585-593.
Delcros, J.G. et al., "Effect of Spermine Conjugating on the Cytotoxicity and Cellular Transport of Acridine", *J. Med. Chem.*, vol. 45, 2002, pp. 5098-5111.
Demeneix, B. A. et al., "Gene transfer into intact vertebrate embryos", *International Journal of Developmental Biology*, vol. 35, 1991, 481-484.
Derwent; "Dialog File 351, Accession No. 10655226", Derwent WPI English language abstract for WO 96/08723 A1 (Document AL15), 1996.
Dingwall, C. et al., "Human immunodeficiency virus 1 tat protein binds trans-activation-responsive region (TAR) RNA in vitro", *Proceedings of the National Academy of Sciences (PNAS)*, vol. 86, No. 18, National Academy Press, Sep. 15, 1989, 6925-6929.
Dingwall, Colin et al., "Nuclear targeting sequences—a consensus?", *Trends in Biochemical Sciences*, vol. 16, Elsevier Science Publishers (UX), Dec. 1991, 478-481.
Dong, Yonghe et al., "Efficient DNA transfection of quiescent mammalian cells using poly-L-orinithine", *Nucleic Acids Research*, vol. 21, No. 3, Feb. 11, 1993, 771-772.
Donnelly-Roberts, D. L. et al., "Structural and Conformational Similarity Between Synthetic Peptides of Curaremimetic neurotoxins and rabies virus glycoprotein", *Mol. Brain Res. 11:*, 1991, 107-113.
Duzgunes, Nejat et al., "Fusion of Liposomes Containing a Novel Cationic Lipid, N[2,3-(Dioleyloxy)propyl]-N,N,N-trimethylammonium: Induction by Multivalent Anions and Asymmetric Fusion with Acidic Phospholipid Vesicles", *Biochemistry*, vol. 28, No. 23, American Chemical Society, 1989, 9179-9184.
Duzgunes, Nejat et al., "Intracellular Delivery of Nucleic Acids and Transcription Factors by Cationic Liposomes", *Meth. Enzymol.*, vol. 221, 1993, 303-317.
Dwarki, V. J. et al., "Cationic Liposome-Mediated RNA Transfection", *Methods in Enzymology*, vol. 217, 1993, 644-654.
Edwards, Michael L. et al., "Synthesis and DNA Binding Properties of Polyamine Analogues", *Journal of Medicinal Chemistry*, vol. 34, No. 8, 1991, 2414-2420.
Elliott, G. et al., "Intercellular trafficking of VP22-GFP fusion proteins", *Gene Therapy*, vol. 6, Jan. 1999, 149-151.
EP0544292, , "Derwent WPI English language abstract for EP 0 544 292 A2", Dialog File 351, Accession No. 9488543 (Document AO7), 1993.
EP07110415; "European Search Report mailed Jan. 26, 2009".
Epand, Richard M. et al., "Peptide models for the membrane destabilizing actions of viral fusion proteins", *Biopolymers*, vol. 32, No. 4, Apr. 1992, 309-314.

Eytan, Gera D. , "Use of Liposomes for reconstitution of biological functions", *Biochimica et Biophysica Acta(BBA)—Reviews on Biomembranes*, vol. 694, No. 2, Oct. 20, 1982, 185-202.
Farhood, H. et al., "Effect of cationic cholesterol derivatives on gene transfer and protein kinase C activity", *Biochim. Biophys. Acta 1111:*, XP000607544, 1992, 239-246.
Fawell, Stephen et al., "Tat-mediated delivery of heterologous proteins into cells", *Proceedings of the National Academy of Sciences (PNAS)*, vol. 91, No. 2, National Academy Press, Jan. 18, 1994, 664-668.
Felgner, et al., "Keystone Symposium on Genetic Targeted Research and Therapeutics: Antisense and Gene Therapy", *J. Cell. Biochem.*, Suppl. 0( 17 Part E), Keystone, CO;, 1993, 206, S306.
Felgner, P. L. , "Cationic Lipid/Polynucleotide Condensates for In vitro and In Vivo Polynucleotide Delivery—The Cytofectins", *J. Liposome Research*, vol. 3, No. 1, 1993, 3-16.
Felgner, P. L. et al., "Cationic liposome-mediated transfection", *Focus*, vol. 11, Life Technologies, Inc., 1989, 21-25.
Felgner, P. L. et al., "Gene Therapeutics", *Nature*, vol. 349, Macmillan Journals, Ltd., Jan. 24, 1991, 351-352.
Felgner, Philip L. et al., "Cationic liposome-mediated transfection", *Nature*, vol. 337, No. 6205, Jan. 26, 1989, 387-388.
Felgner, Philip L. et al., "Lipofection: A Highly Efficient, Lipid-Mediated DNA Transfection Procedure", *Proceedings of the National Academy of Sciences (PNAS)*, vol. 84, 1987, 7413-7417.
Fenyes, Joseph G. et al., "Database CAPLUS on STN", Acc No. 1986:479564,GB 2160538 A, Dec. 24, 1985.
Finlay, D. R. et al., "Nuclear transport in vitro", *Journal of Cell Science—Supplement*, vol. 11, 1989, 225-242.
Fitzgerald, David J. et al., "Adenovirus-induced release of epidermal growth factor and pseudomonas toxin into the cytosol of KB cells during receptor-mediated endocytosis", *Cell*, vol. 32, No. 2, Feb. 1983, 607-617.
Flaman, et al., "A Rapid PCR Fidelity Assay", *Nucleic Acids Research*, vol. 22, No. 15, Aug. 11, 1994, 3259-3260.
Flock, S. et al., "23Na NMR Study of the Effect of Organic Osmolytes on DNA Counterion Atmosphere", *Biophys. J. 71:*, Biophysical Society, Sep. 1996, 1519-1529.
Flock, S. et al., "Dielectric Constant and Ionic Strength Effects on DNA Precipitation", *Biophys. J. 70:*, Biophysical Society, Mar. 1996, 1456-1465.
Flock, S. et al., "Osmotic Effectors and DNA Structure : Effect of Glycine on Precipitation of DNA by Multivalent Cations", *J. Biomol . Struct. & Dynam. 13:*, Adenine Press, 1995, 87-102.
Foecking, M. K. et al., "Powerful and versatile enhancer-promoter unit for mammalian expression vectors", *Gene 45:*, Elsevier Science Publishers B. V., 1986, 101-105.
Fourneau, Mmet et al., "Sur Deux Nouvelles Series D'Anesthesiques Locaux Derives De La Piperazine", *Bulletin De La Societe Chimique De France*, vol. 47(4), May 23, 1930, 1003-1016.
Frackman, S. et al., "Betaine and DMSO: Enhancing Agents for PCR", *Promega Notes 65:*, Promega Corporation, Feb. 1998, 27-29.
Frankel, Alan D. et al., "Activity of Synthetic Peptides from the Tat Protein of Human Immunodeficiency Virus Type 1", *Proceedings of the National Academy of Sciences (PNAS)*, vol. 86, No. 19, National Academy Press, Oct. 1, 1989, 7397-7401.
Friedlander, David R. et al., "Functional mapping of cytotactin: proteolytic fragments active in cell-substrate adhesion", *Journal of Cell Biology*, vol. 107, No. 6, Dec. 1988, 2329-2340.
Fritz, Jeffrey D. et al., "Gene transfer into mammalian cells using histone-condensed Plasmid DNA", *Human Gene Therapy*, vol. 7, Mary Ann Liebert, Inc., Aug. 1, 1996, 1395-1404.
Fukunaga, M. et al., "Liposome entrapment enhances the hypocalcemic action of parenterally administered calcitonin", *Endocrinology*, vol. 115, 1984, 757-761.
Gao, et al., "Potentiation of Cationic Liposome-Mediated Gene Delivery by Polycations", *Biochemistry*, vol. 35, 1996, 1027-1036.
Gao, X. et al., "Cationic Liposomes and Polymers for Gene Transfer", *J. Liposome Res*, vol. 3, No. 1, 1993, 17-30.
Gao, X. et al., "Cytoplasmic expression of a reporter gene by co-delivery of T7 RNA polymerase and T7 promoter sequence with cationic liposomes", *Nucleic Acids Research*, vol. 21, No. 12, 1993, 2867-2872.

(56) References Cited

OTHER PUBLICATIONS

Gao, Xiang et al., "A Novel Cationic Liposome Reagent for Efficient Transfection of Mammalian Cells", *Biochemical and Biophysical Research Communications*, vol. 179, Aug. 30, 1991, 280-285.

Garcia-Bustos, J. et al., "Nuclear protein localization", *Biochim. Biophys. Acta 1071*, Elsevier Science Publishers B.V., 1991, 83-101.

Gardner, John M. et al., "Interaction of fibronectin with its receptor on platelets", *Cell*, vol. 42, No. 2, Sep. 1985, 439-448.

Garrigues, B. et al., "Synthesis of spermine and spermidine selectively substituted on the secondary amine functions", *Chemical Abstracts 111*:, Abstract No. 23282t, American Chemical Society, 1989, 593.

Geall, A.J. et al., "The regiochemical distribution of positive charges along cholesterol polyamine carbamates plays significant roles in modulating DNA binding affinity and lipofection", *FEBS Letters 459*, 1999, pp. 337-342.

Ghonaim, H.M., "Very Long Chain N4,N9-Diacyl Spermines: Non-Viral Lipopolyamine Vectors for Efficient Plasmid DNA and siRNA Delivery", *Pharmaceutical Research*, vol. 26, No. 1, Jan. 2009, pp. 19-31.

Giles, Richard V., "Antisense oligonucleotide technology: From EST to therapeutics", *Current Opinion in Molecular Therapeutics*, vol. 2, No. 3, Pharma Press, Ltd., Jun. 2000, 238-252.

Goldfarb, David et al., "Pathways for the nuclear transport of proteins and RNAs", *Trends in Cell Biology*, vol. 1, No. 1, Jul. 1991, 20-24.

Goldfarb, David S. et al., "Synthetic peptides as nuclear localization signals", *Nature*, vol. 322, Aug. 14, 1986, 641-644.

Goldman, Corey K. et al., "In vitro and in vivo gene delivery mediated by a synthetic polycationic amino polymer", *Nature Biotechnology*, vol. 15, Nature America Publishing, May 1, 1997, 462-466.

Gorman, C., "High Efficiency Gene Transfer into Mammalian Cells", *DNA Cloning*, vol. II, Jul. 1985, 143-190.

Gouesbet, G. et al., "Characterization Transporter of the Erwinia chrysanthemi Osmoprotectant Transporter Gene ousA.", *J. Bacteriol 178*:, American Society for Microbioloby, Jan. 1996, 447-455.

Gould-Fogerite, Susan et al., "Chimerasome-mediated gene transfer in vitro and in vivo", *Gene*, vol. 84, No. 2, Dec. 14, 1989, 429-438.

Grant, Derrick S. et al., "Two different laminin domains mediate the differentiation of human endothelial cells into capillary-like structures in vitro", *Cell*, vol. 58, No. 5, Cell Press, Sep. 8, 1989, 933-943.

Grant, Julius, "Hackh's Chemical Dictionary, 4th ed.", *McGraw-Hill Book Company*, 4th edition, 1969, 391.

Gubler, et al., "A Simple and Very Efficient Method for Generating cDNA Libraries", *Gene*, vol. 25, Nos. 2-3, Nov. 1983, 263-269.

Haensler, Jean et al., "Polyamidoamine cascade polymers mediate efficient transfection of cells in culture", *Bioconjugate Chemistry*, vol. 4, No. 5, Sep. 1993, 372-379.

Hagstrom, James E. et al., "Complexes of non-cationic liposomes and histone H1 mediate efficient transfection of DNA without encapsulation", *Biochimica et Biophysica Acta (BBA)—Biomembranes*, vol. 1284, No. 1, Oct. 2, 1996, 47-55.

Hamana, K. et al., "N'-Methylthermospermine in leguminous seeds", *Chemical Abstracts 117*, Abstract No. 117:86723g, American Chemical Society, 1992, 427.

Hamlin, K. E. et al., "Histamine antagonists. II. Unsymmetrical 1,4-disubstituted piperazines", *J. Am. Chem. Soc.*, vol. 71(8), 1949, 2731-2734.

Harbottle, R. C. et al., "RGD-mediated gene delivery and expression in epithelial cells",*Journal of Cellular Biochemistry. Supplement*, vol. 21A, Abstract No. C6-321, Gene Therapy and Molecular Medicine, Keystone Symposium, Steamboat Springs, CO, Wiley-Liss (1995), Mar. 26-Apr. 1, 1995, 394.

Harfenist, M. et al., "Quarternary Piperazines with Anti-pinworm Activity", *J. Am. Chem. Soc.*, vol. 79, No. 9, 1957, 2211-2215.

Harfenist, M. et al., "Synthesis and Some Stereochemical Aspects of Carbon-methylated Piperazine Quarternary Salts and Related Compounds", *J. Am. Chem. Soc.*, vol. 80 (23), 1958, 6257-6261.

Harrison, G. S. et al., "Optimization of Gene Transfer Using Cationic Lipids in Cell Lines and Primary Human CD4 and CD34 Hematopoietic Cells", *BioTechniques*, vol. 19, Eaton Publishing Company, 1995, 816-823.

Hart, Stephen L. et al., "Lipid-Mediated Enhancement of Transfection by a Nonviral Integrin-Targeting Vector", *Human Gene Therapy*, vol. 9, No. 4, Mar. 1998, 575-585.

Hart, W. et al., "New compounds N,N, N',N'-tetraalkylhomopiperazinium salts", *Journal of Medicinal Chemistry*, vol. 11(6), 1968, 1270-1271.

Haverstick, Doris M. et al., "Inhibition of Platelet Adhesion to Fibronectin, Fibrinogen, and von Willebrand Factor Substrates by a Synthetic Tetrapeptide Derived from the Cell-Binding Domain of Fibronectin", *Blood*, vol. 66, No. 4, Oct. 1, 1985, 946-952.

Hawley-Nelson, Pamela et al., "Lipofectamine Reagent: A New, Higher Efficiency Polycationic Liposome Transfection Reagent", *Focus*, vol. 15, No. 3, Life Technologies Inc., 1993, 73-79.

Hazinski, T. A. et al., "Localization and Induced Expression of Fusion Genes in the Rat Lung", *Am. J. Respir. Cell Mol. Biol. 4*:, American Thoracic Society, 1991, 206-209.

Hengen, P. N., "Optimizing multiplex and LA-PCR with betaine", *Trends Biochem. Sci. 22*:, Elsevier Science, Ltd., Jun. 1997, 225-226.

Henke, W. et al., "Betaine Improves the PCR amplification of GC-rich DNA sequences", *Nucl. Acids Res. 25*:, Oxford University Press, Oct. 1997, 3957-3958.

Henkel und Cie, G.M.B.H. et al., "Low-foaming detergents containing bisquaternary compounds", *Chemical Abstracts*, vol. 72, No. 14, Abstract# 68522p, Apr. 6, 1970, 116.

Hetschko, M. et al., "Reaktionen von Sulfoniumsalzen DES 1,3-Dithiolans und Seiner 2, 2-Substitutionsprodukte", *Tetrahedron Letters*, vol. 17 CAPLUS, Acession No. 1972:461856, STNEasy CAPLUS English language abstract ,Pergamon Press, 1972, 1691-1692.

Heywood, S. M., "tcRAN as a naturally occurring antisense RNA in eukaryotes", *Nucleic Acids Research 14*:, IRL Press, 1986, 6771-6772.

Hogrefe, H. et al., "Novel PCR Enhancing Factor Improves Performance of Pfu DNA Polymerase", *Stratagene Strategies 10*:, Stratagene Cloning Systems, Aug. 1997, 93-96.

Holt, C. E. et al., "Lipofection of cDNAs in the Embryonic Vertebrate Central Nervous System", *Neuron*, vol. 4, Cell Press, 1990, 203-214.

Hope, M. J. et al., "Generation of Multilamellar and Unilamellar Phospholipid Vesicles", *Chem. Phys. Lipids 40*:, Elsevier Scientific Publishers Ireland, Ltd., 1986, 89-107.

Houssier, C. et al., "Effects of Compensatory Solutes on DNA and Chromatin Structural Organization in Solution", *Comp. Biochem. Physiol. 117A*:, Elsevier Science, Inc., Jul. 1997, 313-318.

Houts, et al., "Reverse Transcriptase from Avian Myeloblastosis Virus", *Journal of Virology*, vol. 29, No. 2, Feb. 1979, 517-522.

Huang, L. et al., "Liposome and Immunoliposome Mediated Delivery of Proteins and Peptides", *Targeting of Drugs 3—The Challenge of Peptides and Proteins*, Gregoriadis, G. and Florence, AT. (eds.), Plenum Press, New York, NY., 1992, 45-50.

Huckett, Barbara et al., "Evidence for targeted gene transfer by receptor-mediated endocytosis. Stable expression following insulin-directed entry of NEO into HepG2 cells", *Biochemical Pharmacology*, vol. 40, No. 2, Jul. 15, 1990, 253-263.

Humphries, Martin J. et al., "Identification of an alternatively spliced site in human plasma fibronectin that mediates cell type-specific adhesion", *Journal of Cell Biology*, vol. 103, No. 6, Dec. 1986, 2637-2647.

Humphries, Martin J. et al., "Identification of two distinct regions of the type III connecting segment of human plasma fibronectin that promote cell type-specific adhesion", *Journal of Biological Chemistry*, vol. 262, No. 14, May 15, 1987, 6886-6892.

Iakobashvili, R. et al., "Low temperature cycled PCR protocol for Klenow fragment of DNA polymerase I in the presence of proline", *Nucl. Acids Res. 27*:, Oxford University Press, 1999, 1566-1568.

Innis, M. A., "PCR with 7-Deaza-2 Deoxyguanosine Triphosphate", *PCR Protocols: A Guide to Methods and Applications*, Academic Press, Inc., San Diego, CA, 1990, 54-59.

Invitrogen, , "GIBCO BRL Product Catalogue and Reference Guide", *Life Techonologies, Inc.*, 1995, 19-10 and 19-12.

(56) References Cited

OTHER PUBLICATIONS

Invitrogen, , "Instruction manual for Gene TrapperTM cDNA Positive Selection System", Catalog No. 10356-020, GIBCO BRL, Life Technologies, Gathersburg, MD, 1995, 1-26.
Invitrogen, , "Instruction Manual for GeneTrapper cDNA Positive Selection System", Catalog No. 10356-020, GIBCO BRL, Life Technologies, Jul. 1996, 1-26.
Invitrogen, , "Life Technologies 1993-1994 Catalog and Reference Guide", *Life Technologies, Inc.*, 1993, 9-19,9-21,I-66,R-48-R-51.
Invitrogen, , "Life Technologies Inc. catalogue, Spectrum", Sep. 1999, 1-8.
Ito, A. et al., "Synthetic cationic amphiphiles for liposome-mediated DNA transfection", *Biochemistry International*, vol. 22, Oct. 1990, 235-241.
Iyer, R. P. et al., "3H-1,2-Benzodithiole-3-one 1,1-Dioxide as an Improved Sulfurzing Reagent in the Solid-Phase Synthesis of Oligodeoxyribonucleoside Phosphorothioates", *J. Am. Chem. Soc*, vol. 112, American Chemical Society, 1990, 1253-1254.
Iyer, R. P. et al., "The Automated Synthesis of Sulfur-Containing Oligodeoxyribonucleotides Using 3H-1,2-Benzodithiol-3-one 1,1-Dioxide as a Sulfur-Transfer Reagent", *J. Org. Chem.*, vol. 55, American Chemical Society, 1990, 4693-4699.
Jakob, R. et al., "Reversed-phase ion-pair chromatographic separation of ribulose 1, 5-bisphosphate from 3-phosphoglycerate and its application as a new enzyme assay for RuBP carboxylase-oxygenase", *FEBS Letters*, vol. 183, Elsevier Science Publishers B. V., 1985, 111-114.
Jayatilake, Gamini S. et al., "Rhapsamine, a Cytotoxin from the Antarctic Sponge *Leucetta leptorhapsis*", *Tetrahedron Letters*, vol. 38, No. 43, Oct. 27, 1997, 7507-7510.
Johnstone, et al., "Production of Antibodies", in *Immunochemistry in Practice*, Johnstone. A. and Thorpe, R. eds.Blackwell Scientific Publications, Oxford, Great Britain, 1987, 30-47.
Joung, I et al., "Mutations in two Cysteine-hystidine-rich clusters in adenovirus type 2 DNA Polymerase affect DNA binding", *J. Virol. 66:*, American Society for Microbiology, 1992, 5788-5796.
Kalderon, Daniel et al., "A Short Amino Acid Sequence Able to Specify Nuclear Location", *Cell*, vol. 39, No. 3, Dec. 1, 1984, 499-509.
Kamata, Hideaki et al., "Amphiphilic peptides enhance the efficiency of liposome-mediated DNA transfection", *Nucleic Acids Research*, vol. 22. No. 3, Oxford University Press, Feb. 11, 1994, 536-537.
Kaneda, Yasufumi et al., "Increased Expression of DNA Cointroduced with Nuclear Protein in Adult Rat Liver", *Science*, vol. 243 American Association for the Advancement of Science, Jan. 20, 1989, 375-378.
Kaneda, Yasufumi et al., "Introduction and expression of the human insulin gene in adult rat liver", *Journal of Biological Chemistry*, vol. 264, No. 21, The American Society for Biochemistry and Molecular Biology, Inc., Jul. 25, 1989, 12126-12129.
Kaneda, Yasufumi et al., "The improved efficient method for introducing macromolecules into cells using HVJ (Sendai virus) liposomes with gangliosides", *Experimental Cell Research*, vol. 173, Academic Press Inc., 1987, 56-69.
Karlsson, Stefan et al., "Transfer of Genes into Hematopoietic Cells Using Recombinant DNA Viruses", *Proceedings of the National Academy of Sciences (PNAS)*, vol. 82, No. 1, National Academy Press, Jan. 1, 1985, 158-162.
Kielian, M. et al., "Entry of alphaviruses", *The Togaviridae and Flaviviridae (The Viruses)*, Schlesinger S. and Schlesinger, M.J., eds., May 31, 1986, 91-119.
Kim, et al., "Preparation of multivesicular liposomes", *Biochim Biophys. Acta.*, 728, 1983, 339-348.
Kim, S. et al., "Preparation of Multivesicular Liposomes", *Biochim. Biophys. Acta*, vol. 728, 1983, 339-348.
Kirsch, Thomas et al., "Cloning, High-Yield Expression in *Escherichia coli*, and Purification of Biologically Active HIV-1 Tat Protein", *Protein Expression and Purification*, vol. 8, No. 1, Academic Press, Inc., Aug. 1996, 75-84.

Klappe, Kai M. et al., "Parameters Affecting Fusion between Sendai Virus and Liposomes. Role of ViralProteins, Liposome Composition, and pH", *Biochemistry*, vol. 25, No. 25, Dec. 1986, 8252-8260.
Knodis, Z. et al., "New reactions of 1,1-diamines", *Chemical Abstracts 120*, Abstract No. 270276b, American Chemical Society, 1994, 1056.
Kondakova, N. V. et al., "Effect of Low-molecular Amines on DNA Conformation and Stability of Double Helix", *Mol. Biol. (Mosk) 9:*, Izdatelstvo Nauka, 1975, 742-745.
Konopka, Krystyna et al., "Enhancement of human immunodeficiency virus type 1 infection by cationic liposomes: the role of CD4, serum and liposome-cell interactions", *Journal of General Virology*, vol. 72, No. 11, Nov. 1991, 2685-2696.
Kotewicz, et al., "Isolation of cloned Moloney murine leukemia virus reverse transcriptase lacking ribonuclease H activity", *Nucleic Acids Research*, vol. 16, No. 1, IRL Press Limited, Oxford, England, Jan. 11, 1988, 265-277.
Kraaijeveld, C. A. et al., "The effect of liposomal charge on the neutralizing antibody response against inactivated encephalomyocarditis and Semliki Forest viruses", *Clinical & Experimental Immunology*, vol. 56, No. 3, Jun. 1984, 509-514.
Kukowska-Latallo, Jolanta F. et al., "Efficient Transfer of Genetic Material into Mammalian Cells Using Starburst Polyamidoamine Dendrimers", *Proceedings of the National Academy of Sciences (PNAS)*, vol. 93, No. 10, National Academy Press, May 14, 1996, 4897-4902.
Landre, P. A. et al., "The Use of Cosolvents to Enhance Amplification by the Polymerase Chain Reaction", In: *PCR Strategies*, Innis, M.A. et al., eds.,, Academic Press, 1995, 3-16.
Lanford, R. E. et al., "Induction of Nuclear Transport with a Synthetic Peptide Homologous to the SV40 T Antigen Transport Signal", *Cell*, vol. 46, Cell Press, Aug. 15, 1986, 575-582.
Lanford, Robert E. et al., "Comparison of diverse transport signals in synthetic peptide-induced nuclear transport", *Experimental Cell Research*, vol. 186, No. 1, Jan. 1990, 32-38.
Langel, U. et al., "Cell penetrating PNA constructs", *Journal of Neurochem*, vol. 69 (suppl), Abstract B, Lippincott-Raven Publishers, Jul. 1997, S260.
Lapidot, Moshe et al., "Fusion-mediated microinjection of liposome-enclosed DNA into cultured cells with the aid of influenza virus glycoproteins", *Experimental Cell Research*, vol. 189, No. 2, Elsevier, Aug. 1990, 241-246.
Lau, Quek C. et al., "Abrogation of c-Raf expression induces apoptosis in tumor cells", *Oncogene*, vol. 16, Stockton Press, Apr. 8, 1998, 1899-1902.
Lawler, Jack et al., "Cell attachment to thrombospondin: the role of ARG-GLY-ASP, calcium, and integrin receptors", *The Journal of Cell Biology*, vol. 107, No. 6, Dec. 1, 1988, 2351-2631.
Lawyer, Frances C. et al., "High-level Expression, Purification, and Enzymatic characterization of Full-length Thermus aquaticus DNA polymerase and a Truncated Form Deficient in 5' to 3' Exonuclease activity", *PCR Methods and Applications*, vol. 2, No. 4, May 1993, 275-287.
Le Rudulier, D. et al., "Molecular Biology of Osmoregulation", *Science 224:*, American Association for the Advancement of Science, 1984, 1064-1068.
Ledley, Fred D. , "Clinical Considerations in the Design of Protocols for Somatic Gene Therapy", *Human Gene Therapy*, vol. 2, No. 1, Apr. 1991, 77-83.
Legendre, Jean-Yves "Cyclic Amphipathic Peptide-DNA Complexes Mediate High-efficiency Transfection of", *Proceedings of the National Academy of Sciences (PNAS)*, vol. 90, Feb. 1993, 893-897.
Legendre, Jean-Yves et al., "Delivery of Plasmid DNA into Mammalian Cell Lines Using pH-Sensitive Liposomes: Comparison with Cationic Liposomes", *Pharmaceutical Research*, vol. 9, No. 10, Oct. 1992, 1235-1242.
Li, Cong-Jun et al., "Nonprotein Amino Acids from Seeds of Cycas circinalis and Phaseolus vulgaris", *Phytochemistry*, vol. 42, No. 2, Pergamon Press, May 1996, 443-445.
Liljestrom, P. et al., "A New Generation of Animal Cell Expression Vectors Based on the Semliki Forest Virus Replicon", *Biotechnology*, vol. 9, Nature Publishing Company, 1991, 1356-1361.

(56) References Cited

OTHER PUBLICATIONS

Litzinger, David C. et al., "Amphipathic poly(ethylene glycol) 5000-stabilized dioleoylphosphatidylethanolamine liposomes accumulate in spleen", *Biochimica et Biophysica Acta*, vol. 1127, 1992, 249-254.

Litzinger, David C. et al., "Phosphatidylethanolamine liposomes:drug delivery, gene transfer and immunodiagnostic applications", *Biochimica et Biophysica Acta*, vol. 1113, 1992, 201-227.

Liu, X. et al., "Hypoglycemia-induced c-Jun Phosphorylation Is Mediated by c-Jun N-terminal Kinase 1 and Lyn Kinase in Drug-resistant Human Breast Carcinoma MCF-7/ADR Cells", *J. Biol. Chem*, vol. 272, The American Society for Biochemistry and Molecular Biology, Inc., May 1997, 11690-11693.

Loeffler, Jean-Philippe et al., "Gene Transfer into Primary and Established Mammalian Cell Lines with Lipopolyamine-Coated DNA", *Methods in Enzymology*, vol. 217, Academic Press, Inc., 1993, 599-618.

Loyter, Abraham et al., "Mechanisms of DNA Uptake by Mammilian Cells: Fate of Exoneneously Added DNA Monitored by the Use of Fluorescent Dyes", *Proceedings of the National Academy of Sciences (PNAS)*, vol. 79, No. 2, Jan. 15, 1982, 422-426.

Mack, Karl D. , "Cationic lipid enhances in vitro Receptor-mediated Transfection", *The American Journal of the Medical Sciences*, vol. 307, No. 2, Feb. 1994, 138-143.

Malin, G. et al., "Induction of Synthesis of Tetrahydropyrimidine Derivatives in Streptomyces Strains and Their Effect on Bscherichia coli in Response to Osmotic and Heat Stress", *J. Bacteriol. 178:*, American Society for Microbiology, Jan. 1996, 385-395.

Malone, Robert W. et al., "Cationic Llposome-Mediated RNA Transfection", *Proceedings of the National Academy of Sciences (PNAS)*, vol. 86, No. 16, Aug. 15, 1989, 6077-6081.

Maniatis, Tom et al., "The Isolation of Structural Genes from Libraries of Eucaryotic DNA", *Cell*, vol. 15, No. 2, Oct. 1978, 687-701.

Mann, D. A. et al., "Endocytosis and targeting of exogenous HIV-1 Tat protein", *The EMBO Journal*, vol. 10, No. 7, 1991, 1733-1739.

Marquet, R. et al., "Thermodynamics of Cation-Induced DNA Condensation", *J. Biomol. Struct. & Dynam. 9:*, Adenine Press, 1991, 159-167.

Marsh, Mark et al., "Interactions of Semliki Forest virus spike glycoprotein rosettes and vesicles with cultured cells", *Journal of Cell Biology*, vol. 96, No. 2, Feb. 1, 1983, 455-461.

Mason, Peter W. et al., "RGD sequence of foot-and-mouth disease virus is essential for infecting cells via the natural receptor but can be bypassed by an antibody-dependent enhancement pathway", *Proceedings of the National Academy of Sciences (PNAS)*, vol. 91, No. 5, Mar. 1, 1994, 1932-1936.

Mayer, L. D. et al., "Vesicles of Variable Sizes Produced by a Rapid Extrusion Procedure.", *Biochimica et Biophysica Acta*, vol. 858, 1986, 161-168.

Mayhew, E. et al., "Characterization of liposomes prepared using a microemulsifier", *Biochim Biophys. Acta*, vol. 775, No. 2, Aug. 22, 1984, 169-174.

Mazur, W. et al., "Direct Gene Transfer into the Coronary Arteries of Intact Animals via Infusion Balloon Catheters: Comparison of Canine and Porcine Model Systems", *Journal of the American College of Cardiology*, vol. 21, No. 2, Abstract 889-30, Feb. 1993, 186A.

Mazur, W. et al., "The Efficiency of Lipofectin-Mediated Gene Transfer into Porcine and Human Coronary Smooth Muscle Cells is Dramatically Improved by the Influenza Virus Hemagglutinin Antigen", *Journal of the American College of Cardiology*, Sppl. 21, Abstract No. 889-31, 1993, 186A.

McCluskie, et al., "Direct gene transfer to the respiratory tract of mice with pure plasmid and lipid-formulated DNA (Chemical Abstract)", CAPLUS ACS on STN, AN 1998:736678, 1998.

McCluskie, M. J. et al., "Direct gene transfer to the respiratory tract of mice with pure plasmid and lipid-formulated DNA", *Antisense Nucleic Acid Drug Dev.*, vol. 8, No. 5., Oct. 1998, 401-414.

McCluskie, Michael J. et al., "Direct gene transfer to the respiratory tract of mice with pure plasmid and lipid-formulated DNA", *Chemical Abstracts*, vol. 130, No. 8, abstract No. 91045k, Feb. 1999, 151.

Miescher, K. et al., "Imidazoline and tetrahydrophyrimidine compounds", Database CAPLUS on STN, Acc. No. 1941:47840, DE 701322, Dec. 12, 1940.

Miyanohara, A. et al., "Partial Cell-Free Assembly of VSV-G Pseudotyped Retrovirus Particles", *Molecular and Cell Biology of Gene Therapy*, Abstract No. 007, Keystone Symposia, Keystone, Colorado, meeting date Jan. 19-25, 1998, Dec. 1997, 34.

Mizuno, T. et al., "A Unique Mechanism Regulating Gene Expression: Translational Inhibition by a Complementary RNA Transcript (micRNA)", *Proceedings of the National Academy of Sciences (PNAS)*, vol. 81, 1984, 1966-1970.

Monia, B. P. et al., "Sequence-specific antitumor activity of a phosphorothioate oligodeoxyribonucleotide targeted to Human C-raf kinase supports an antisense mechanism of action in vivo", *Proceedings of the National Academy of Sciences (PNAS)*, vol. 93, 1996, 15481-15484.

Murata, M. et al., "Modification of the N-terminus of membrane fusion-active peptides blocks the fusion activity", *Biochemical and Biophysical Research Communications*, vol. 179, No. 2, 1991, 1050-1055.

Murphy, Anthea L. et al., "Catch VP22: the hitch-hiker's ride to gene therapy?", *Gene Therapy*, vol. 6, No. 4-5, Jan. 1999, 4-5.

Mytelka, D. S. et al., "Analysis and suppression of DNA polymerase pauses associated with a trinucleotide consensus", *Nucl. Acids Res.*, vol. 24, No. 14, Jul. 1996, 2774-2781.

Nabel, G. J. et al., "Direct Gene Transfer for Treatment of Human Cancer", *Annals of the New York Academy of Sciences*, vol. 772, 1995, 227-231.

Nabel, Gary J. et al., "Direct gene transfer for immunotherapy and immunization", *Trends in Biotechnology*, vol. 11, No. 5, May 1993, 211-215.

Nabel, Gary J. et al., "Immune responses in human melanoma after transfer of an allogeneic class I major histocompatibility complex gene with DNA-liposome complexes", *Proceedings of the National Academy of Science (PNAS)*, vol. 93, No. 26, Dec. 24, 1996, 15388-15393.

Nair, Smita et al., "Class I restricted CTL recognition of a soluble protein delivered by liposomes containing lipophilic polylysines", *Journal of Immunological Methods*, vol. 152, No. 2, Aug. 10, 1992, 237-243.

Neckers, Leonard M. , "Ch 25: Cellular Internalization of Oligodeoxynucleotides", *Antisense Research and Applications*, Crooke S.T. and Leblue, B., eds., CRC Press, Inc., Boca Raton, FL., May 1993, 451-460.

Neugebauer, Judith M. , "Detergents: An Overview", *Methods in Enzymology*, vol. 182, 1990, 239-253.

Neurath, et al., "B cell epitope mapping of human immunodeficiency virus envelope glycoproteins with long (19- to 36-residue) synthetic peptides", *J. Gen. Virol.*, vol. 71, 1990, 85-95.

Niidome, Takuro et al., "Binding of Cationic alpha-Helical Peptides to Plasmid DNA and Their Gene Transfer Abilities into Cells", *The Journal of Biological Chemistry*, vol. 272, No. 24, Jun. 13, 1997, 15307-15312.

Okayama, et al., "High-efficiency cloning of full length cDNA", *Molecular and Cellular Biology*, vol. 2, No. 2, 1982, 161-170.

Olson, F. et al., "Preparation of liposomes of defined size distribution by extrusion through polycarbonate membranes", *Biochimica et Biophysica Acta*, vol. 557, 1979, 9-23.

Otero, M. J. et al., "Proteins are Cointernalized with Virion Particles during Early Infection", *Virology*, vol. 160, No. 1, Sep. 1987, 75-80.

Panaccio, M. et al., "FoLT PCR: A Simple PCR Protocol for Amplifying DNA Directly from Whole Blood", *Bio Tech.*, vol. 14, 1993, 238-243.

Parente, Roberta A. et al., "Association of a pH-sensitive peptide with membrane vesicles: role of amino acid sequence", *Biochemistry*, vol. 29, No. 10, Sep. 1990, 8713-8719.

Parente, Roberta A. et al., "Mechanism of Leakage of Phospholipid Vesicle Contents Induced by the Peptide GALA", *Biochemistry*, vol. 29, No. 37, Sep. 1990, 8720-8728.

Park, Y. S. et al., "Interaction of synthetic glycophospholipids with phospholipid bilayer membranes", *Biochimica et Biophysica Acta*, vol. 1112, 1992, 251-258.

(56) References Cited

OTHER PUBLICATIONS

Park, Y. S. et al., "Some negatively charged phospholipid derivatives prolong the liposome circulation in vivo", *Biochimica et Biophysica Acta*, vol. 1108, 1992, 257-260.
Pastan, Ira H. et al., "Journey to the center of the cell: role of the receptosome", *Science*, vol. 214, No. 4520, Oct. 30, 1981, 504-509.
Paterson, B. M. et al., "Structural Gene Identification and Mapping by DNA-mRNA Hybrid-Arrested Cell-Free Translation", *Proceedings of the National Academy of Sciences (PNSA)*, vol. 74, No. 10, 1977, 4370-4374.
PCT/US99/026825; International Search Report mailed Feb. 22, 2000, 5 pages.
Pepinsky, R. B. et al., "Specific inhibition of a human papillomavirus E2 trans-activator by intracellular delivery of its repressor", *DNA and Cell Biology*, vol. 13, No. 10, 1994, 1011-1019.
Phalen, Thomas et al., "Cholesterol is required for infection by Semliki Forest virus", *Journal of Cell Biology*, vol. 112, No. 4, Feb. 1, 1991, 615-623.
Pierschbacher, Michael D. et al., "Cell attachment activity of fibronectin can be duplicated by small synthetic fragments of the molecule", *Nature*, vol. 309, May 3, 1984, 30-33.
Pierschbacher, Michael D. et al., "Influence of stereochemistry of the sequence Arg-Gly-Asp-Xaa on binding specificity in cell adhesion", *The Journal of Biological Chemistry*, vol. 262, No. 36, Dec. 25, 1987, 17294-17298.
Pinnaduwage, Purnima et al., "Use of a Quaternary Ammonium Detergent in Liposome Mediated DNA Transfection of Mouse L-cells", *Biochimica et Biophysica Acta (BBA)—Biomembranes*, vol. 985, No. 1, Oct. 2, 1989, 33-37.
Polesky, et al., "Identification of Residues Critical for the Polymerase Activity of the Klenow Fragment of DNA Polymerase I from *Escherichia coli*", *The Journal of Biological Chemistry*, vol. 265, No. 24, Aug. 25, 1990, 14579-14591.
Poste, George et al., "Lipid vesicles as carriers for introducing biologically active materials into cells", *Methods in Cell Biology*, vol. 14, 1976, 33-71.
Prochiantz, Alain, "Getting hydrophilic compounds into cells: lessons from homeopeptides", *Current Opinion in Neurobiology*, vol. 6, 1996, 629-634.
Prochiantz, Alain, "Peptide nucleic acid smugglers", *Nature Biotechnology*, vol. 16, Sep. 1998, 819-820.
Promega, "Eukaryotic transcription and Reporter Systems", *1993/94 Promega Catalog*, Promega Corporation, 1993, 251.
Rafferty, J. A. et al., "Sequence Analysis of a Family of Highly Repeated DNA Units in Stauroderus Scalaris (Orthoptera)", *Intl. J. Genome Res.*, vol. 1, 1992, 1-16.
Rajendrakumar, C. S. et al., "DNA helix destabilization by proline and betaine: possible role in the salinity tolerance process", *FEBS Lett.*, vol. 410, Jun. 1997, 201-205.
Randall, K. et al., "Accumulation of natural and synthetic betaines by a mammalian renal cell line", *Biochem. Cell Biol.*, vol. 74, Apr. 1996, 283-287.
Randall, K. et al., "Natural and synthetic betaines counter the effects of high NaCl and urea concentrations", *Biochim. Biophys. Acta*, vol. 1291, 1996, 189-194.
Rees, W. A. et al., "Betaine Can Eliminate the Base Pair Composition Dependence of DNA Melting", *Biochemistry*, vol. 32, 1993, 137-144.
Remy, Jean-Serge et al., "Targeted gene transfer into hepatoma cells with lipopolyamine-condensed DNA particles presenting galactose ligands: a stage toward artificial viruses", *Proceedings of the National Academy of Sciences (PNAS)*, vol. 92, No. 5, Feb. 28, 1995, 1744-1748.
Rihs, Hans-Peter et al., "Nuclear transport kinetics depend on phosphorylation-site-containing sequences flanking the karyophilic signal of the Simian virus 40 T-antigen", *The EMBO Journal*, vol. 8, No. 5, IRL Press, 1989, 1479-1484.
Rihs, Hans-Peter et al., "The rate of nuclear cytoplasmic protein transport is determined by the casein kinase II site flanking the nuclear localization sequence of the SV40 T-antigen", *EMBO J.* vol. 10, No. 3, Mar. 1991, 633-639.
Rose, John K. et al., "A new cationic liposome reagent mediating nearly quantitative transfection of animal cells", *Biotechniques*, vol. 10, No. 4, Apr. 1991, 520-525.
Rosenkranz, Andrey A. et al., "Receptor-Mediated Endocytosis and Nuclear Transport of a Transfecting DNA Construct", *Experimental Cell Research*, vol. 199, No. 2, Apr. 1992, 323-329.
Rosenthal, A. F. et al., "A Synthetic Inhibitor of Venom Lecithinase A", *J. Biol. Chem.*, vol. 235, 1960, 2202-2206.
Rothenberg, Mace et al., "Oligodeoxynucleotides as Anti-Sense Inhibitors of Gene Expression: Therapeutic Implications", *Journal of the National Cancer Institute*, vol. 81, No. 20, Oct. 18, 1989, 1539-1544.
Ruoslahti, Erkki et al., "New perspectives in cell adhesion: RGD and integrins", *Science*, vol. 238, Oct. 23, 1987, 491-497.
Saiki, Randall K. et al., "Primer-Directed Enzymatic Amplification of DNA with a Thermostable DNA Polymerase", *Science*, Reports, vol. 239,, Jan. 29, 1988, 487-491.
Sands, J. A., "Virucidal activity of cetyltrimethylammonium bromide below the critical micelle concentration", *FEMS Microbiology Letters*, vol. 36, Nov. 1, 1986, 261-263.
Scheule, Ronald K., "Novel Preparation of Functional Sindbis Virosomes", *Biochemistry*, vol. 25, No. 15, Jul. 1986, 4223-4232.
Schlegel, Richard et al., "Biologically Active Peptides of the Vesicular Stomatitis Virus Glycoprotein", *The Journal of Virology*, vol. 53, No. 1, Jan. 1985, 319-323.
Schlegel, Richard et al., "Inhibition of VSV binding and infectivity by phosphatidylserine: Is phosphatidylserine a VSV-binding site?", *Cell*, vol. 32, No. 2, Feb. 1983, 639-646.
Schmid, Nathalie et al., "Location of spermine and other polyamines on DNA as revealed by photoaffinity cleavage with polyaminobenzenediazonium salts", *Biochemistry*, vol. 30, 1991, 4357-4361.
Schusteritz, et al., "Struktur und Wirkung von Piperazin- und Athylendiamin-Derivaten", vol. 9(10) Arzneimittel Forschung. Drug Research, ECV Editio Cantor Verlag, Aulendorf, DE,, Jan. 1, 1959, 628-633.
Seth, P. et Cells Crowell al., "Pathway of Adenovirus Entry into Cells", *Virus Attachment and Entry into Cells*, Crowell R. L. and Longberg-Holm K. eds., American Society for Microbiology, WA., D.C., 1986, 191-195.
Shepard, A. R. et al., "Magnetic Bead Capture of cDNAs from Double-Stranded Plasmid cDNA Libraries", *Nucl. Acids Res.*, vol. 25, No. 15, Aug. 1997, 3183-3185.
Sigma,, "Bioactive Peptides", *Sigma Chemical Company Catalogue*, St. Louis, MO, 1993, 1028-1034.
Silver, Pamela A., "How Proteins Enter the Nucleus", *Cell*, vol. 64, No. 3, Feb. 8, 1991, 489-497.
Singh, R. S. et al., "Anchor Dependency for Non-Glycerol Based Cationic Lipofectins: Mixed Bag of Regular and Anomalous Transfection Profiles", *Chem. Eur. J.*, vol. 8, No. 4, 2002, 900-909.
Smith, D. R. et al., "Preparation of Symmetrical N,N'-Disubstituted Piperazines and their Quaternary Ammonium Salts", *J. Am. Chem. Soc.*, vol. 72, No. 7, 1950, 2969-2970.
Smull, Christine E. et al., "Enhancement of the Plaque-Forming Capacity of Poliovirus Ribonucleic Acid with Basic Proteins", *Journal of Bacteriology*, vol. 84, No. 5, Nov. 1962, 1035-1040.
Soltis, et al., "The α and β Chains of Avian Retrovirus Reverse Transcriptase Independently Expressed in *Escherichia coli*: Characterization of Enzymatic Activities", *Proceedings of the National Academy of Sciences*, vol. 85, No. 10, May 1988, 3372-3376.
Stegmann, T. et al., "Protein-Mediated Membrane Fusion", *Annu. Rev. Biophys. Biophys. Chem.*, vol. 18, 1989, 187-211.
Stewart, Mark J. et al., "Gene Transfer In Vivo with DNA-Liposome Complexes: Safety and Acute Toxicity in Mice", *Human Gene Therapy*, vol. 3, No. 3, 1992, 267-275.
Stopeck, A. T. et al., "Phase I study of direct gene transfer of an allogeneic histocompatibility antigen, HLA-B7, in patients with metastatic melanoma", *Journal of Clinical Oncology*, vol. 15, Jan. 1997, 341-349.

(56) References Cited

OTHER PUBLICATIONS

Sugawa, Hideo et al., "Large Macromolecules can be Introduced into Cultured Mammalian Cells Using Erythrocyte Membrane Vesicles", *Experimental Cell Research*, vol. 159, No. 2, Aug. 1985, 410-418.

Suzuki, Shintaro et al., "Complete amino acid sequence of human vitronectin deduced from cDNA. Similarity of cell attachment sites in vitronectin and fibronectin", *The EMBO Journal*, vol. 4, No. 10, IRL Press, Ltd., Oct. 1985, 2519-2524.

Szoka, Francis et al., "Procedure for Preparation of Liposomes with Large Internal Aqueous Space and High Capture by Reverse-Phase Evaporation.", *Proceedings of the National Academy of Sciences (PNAS)*, vol. 75, No. 9, Sep. 1978, 4194-4198.

Szoka, Francis J. et al., "Comparative Properties and Methods of Preparation of Lipid Vesicles (Liposomes)", *Annu. Rev. Biophys. Bioeng*, vol. 9, 1980, 467-508.

Tang, De-Chu et al., "Genetic Immunization is a Simple Method for Eliciting an Immune Response", *Nature*, vol. 356, Mar. 12, 1992, 152-154.

Tang, Mary X. et al., "In Vitro Gene Delivery by Degraded Polyamidoamine Dendrimers", *Bioconjugate Chemistry*, vol. 7, 1996, 703-714.

Thompson, L., "A Shot in the Arm for Vaccine Problems", *Washington Post*, Jun. 7, 1993, AO3.

Tikchonenko, Thomas I. et al., "Transfer of condensed viral DNA into eukaryotic cells using proteoliposomes", *Gene*, vol. 63, No. 2, Mar. 31, 1988, 321-330.

Trubetskoy, V. S. et al., "Cationic liposomes enhance targeted delivery and expression of exogenous DNA mediated by N-terminal modified poly(L-lysine)-antibody conjugate in mouse lung endothelial cells", *Biochim. Biophys. Acta.*, vol. 1131, 1992, 311-313.

Trubetskoy, Vladimir S. et al., "Use of N-Terminal Modified Poly (L-Lysine)-Antibody Conjugates as a Carrier for Targeted Gene Delivery in Mouse Lung Endothelial Cells", *Bioconjug. Chem.*, vol. 3, 1992, 323-327.

Uhlmann, E. et al., "Antisense Oligonucleotides: A New Therapeutic Principle", *Chemical Reviews*, vol. 90 (4), Jun. 1990, 543-584.

Ulmer, et al., "Heterologous Protection Against Influenza by Injection of DNA Encoding a Viral Protein", *Science*, vol. 259, No. 4102, Mar. 19, 1993, 1745-1749.

Urdea, Mickey S. , "Branched DNA Signal Amplification", *Bio/Technology*, vol. 12, Sep. 1994, 926-928.

Vaananen, Pertti et al., "Fusion and Haemolysis of Erythrocytes caused by Three Togaviruses: Semliki Forest, Sindbis and Rubella", *Journal of General Virology*, vol. 46, No. 2, Feb. 1980, 467-475.

Van Der Krol, Alexander R. et al., "Modulation of Eukaryotic Gene Expression by Complementary RNA or DNA Sequences", *Biotechniques*, vol. 6, No. 10, 1988, 958-976.

Van Zee, Karen et al., "A hydrophobic protein sequence can override a nuclear localization signal independently of protein context", *Molecular and Cellular Biology*, vol. 11, No. 10, 1991, 5137-5146.

Varadaraj, K. et al., "Denaturants or cosolvents improve the specificity of PCR amplification of a G+C-rich DNA using genetically engineered DNA polymerases", *Gene*, vol. 140, 1994, 1-5.

Vives, Eric et al., "A truncated HIV-1 Tat protein basic domain rapidly translocates through the plasma membrane and accumulates in the cell nucleus", *The Journal of Biological Chemistry*, vol. 272, No. 25, Jun. 20, 1997, 16010-16017.

Voyager, , "The Power of Translocation", *Expression 6*, Life Technologies, Inc. Invitrogen, Feb. 1999, 6.

Voytik-Harbin, S. L. et al., "Identification of extractable growth factors from small intestinal submucosa", *Journal of Cellular Biochemistry*, vol. 67, Dec. 1997, 478-491.

Wagner, Ernst et al., "Coupling of adenovirus to transferrin-polylysine/DNA complexes greatly enhances receptor-mediated gene delivery and expression of transfected genes", *Proceedings of the National Academy of Sciences (PNAS)*, vol. 89, Jul. 1992, 6099-6103.

Wagner, Ernst et al., "DNA-binding transferrin conjugates as functional gene-delivery agents: synthesis by linkage of polylysine or ethidium homodimer to the transferrin carbohydrate moiety", *Bioconjug Chem*, vol. 2, No. 4, 1991, 226-231.

Wagner, Ernst et al., "Influenza virus hemagglutinin HA-2 N-terminal fusogenic peptides augment gene transfer by transferrin-polylysine-DNA complexes: toward a synthetic virus-like gene-transfer vehicle", *Proceedings of the National Academy of Sciences (PNAS)*, vol. 89, No. 17, Sep. 1, 1992, 7934-7938.

Wagner, Ernst et al., "Transferrin-Polycation Conjugates as Carriers for DNA Uptake into Cells", *Proceedings of the National Academy of Sciences (PNAS)*, vol. 87, May 1990, 3410-3414.

Wagner, Ernst et al., "Transferrin-Polycation-DNA Complexes: The Effect of Polycations on the Structure of the Complex and DNA Delivery to Cells", *Proceedings of the National Academy of Sciences (PNAS)*, vol. 88, May 1991, 4255-4259.

Walker, Christopher et al., "Cationic lipids direct a viral glycoprotein into the class I major histocompatibility complex antigen-presentation pathway", *Proceedings of the National Academy of Sciences (PNAS)*, vol. 89, No. 17, Sep. 1, 1992, 7915-7918.

Wang, Bin et al., "Gene Inoculation Generates Immune Responses Against Human Immunodeficiency virus Type 1", *Proceedings of the National Academy of Sciences (PNAS)*, vol. 90, May 1, 1993, 4156-4160.

Wayner, Elizabeth A. et al., "Identification and characterization of the T lymphocyte adhesion receptor for an alternative cell attachment domain (CS-1) in plasma fibronectin", *The Journal of Cell Biology*, vol. 109, No. 3, Sep. 1, 1989, 1321-1330.

Weinstock, L. T. et al., "Synthesis of new polyamine derivatives for cancer Chemotherapeutic studies", *J. Pharm. Sci.*, vol. 70, 1981, 956-959.

Weissensteiner, T. et al., "Strategy for Controlling Preferential Amplification and Avoiding False Negatives in PCR Typing", *BioTechniques*, vol. 21, Dec. 1996, 1102-1108.

Wen, Wei et al., "Identification of a signal for rapid export of proteins from the nucleus", *Cell*, vol. 82, Aug. 11, 1995, 463-473.

White, J. M., "Cell-to-cell fusion", *Current Opinion in Cell Biology*, vol. 1, 1989, 934-939.

White, J. M., "Viral and Cellular Membrane Fusion Proteins", *Ann. Rev. Physiol.*, vol. 52, 1990, 675-697.

Whitmore, et al., "Journal of the American Chemical Society", Database CAPLUS on STN, Acc. No. 1944:24921, 1944, 725-731.

Wickham, T. J. et al., "Targeting of adenovirus penton base to new receptors through replacement of its RGD motif with other receptor-specific peptide motifs", *Gene Therapy*, vol. 2, 1995, 750-756.

Wickstrom, E. et al., "Down-regulation of c-Myc antigen expression in lymphocytes of E.mu.-c-myc transgenic mice treated with anti-c-myc DNA methylphosphonates", *Cancer Res.*, 52, 1992, 6741-6745.

Wickstrom, E. L. et al., "Human Promyelocytic Leukemia HL-60 Cell Proliferation and c-myc Protein Expression are Inhibited by an Antisense Pentadecadeoxynucleotide Targeted against c-myc mRNA", *Proceedings of the National Academy of Sciences (PNAS)*, vol. 85, 1988, 1028-1032.

Wilson, James M. et al., "Hepatocyte-directed gene transfer in vivo leads to transient improvement of hypercholesterolemia in low density lipoprotein receptor-deficient rabbits", *Journal of Biological Chemistry*, vol. 267, No. 2, Jan. 15, 1992, 963-967.

Wolff, Jon A. et al., "Direct Gene Transfer into Mouse Muscle in Vivo", *Science*, vol. 247, No. 4949, Mar. 23, 1990, 1465-1468.

Woodford, K. et al., "The Use of K+-free buffers eliminates a common cause of premature chain termination in PCR and PCR sequencing", *Nucl. Acids Res.*, vol. 23, 1995, 539.

Wu, Catherine H. et al., "Targeting genes: delivery and persistent expression of a foreign gene driven by mammalian regulatory elements in vivo", *Journal of Biological Chemistry*, vol. 264, No. 29, Oct. 15, 1989, 16985-16987.

Wu, George Y. et al., "Evidence for targeted gene delivery to Hep G2 hepatoma cells in vitro", *Biochemistry*, vol. 27, No. 3, 1988, 887-892.

Wu, George Y. et al., "Receptor-mediated gene delivery and expression in vivo", *Journal of Biological Chemistry*, vol. 263, No. 29, The American Association for Biochemistry and Molecular Biology, Inc., Oct. 15, 1988, 14621-14624.

(56) References Cited

OTHER PUBLICATIONS

Wu, George Y. et al., "Receptor-mediated gene delivery in vivo: Partial correction of genetic analbuminemia in Nagase rats", *Journal of Biological Chemistry*, vol. 266, No. 22, Aug. 5, 1991, 14338-14342.

Yagi, K. et al., "Incorporation of histone into liposomes increases the efficiency of liposome-mediated gene transfer", *Journal of Clinical Biochemistry and Nutrition*, vol. 10, 1991, 21-25.

Yoshimura, Kunihiko et al., "Adenovirus-mediated augmentation of cell transfection with unmodified plasmid vectors", *Journal of Biological Chemistry*, vol. 268, No. 4, Feb. 5, 1993, 2300-2303.

Young, John D. et al., "Interaction of Enveloped Viruses with Planar Bilayer Membranes: Observations on Sendai, Influenza, Vesicular Stomatitis, and Semliki Forest Viruses", *Virology*, vol. 128, No. 1, Jul. 15, 1983, 186-194.

Zaitsev, S. V. et al., "H1 and HMG17 extracted from calf thymus nuclei are efficient DNA carriers in gene transfer", *Gene Therapy*, vol. 4, No. 6, 1997, 586-592.

Zana, R et al., "Dependence of aggregate morphology on structure of dimeric surfactants", Department of Chemlc:ai Engineering,. Technion-Israel Instituteof Technology. Halla 32000. Israel *Nature •* vol. 362. Mar. 18, 1993, 228-230.

Zenke, Martin et al., "Receptor-Mediated Endocytosis of Transferrin-Polycation Conjugates: An Efficient Way to Introduce DNA Into Hematopoietic Cells", *Proceedings of the National Academy of Sciences (PNAS)*, vol. 87, May 1990, 3655-3659.

Zhou, X. et al., "Targeted delivery of DNA by liposomes and polymers", *Journal of Controlled Release*, vol. 19, 1992, 269-74.

Zhou, Xiaohuai et al., "DNA transfection mediated by cationic liposomes containing lipopolylysine: characterization and mechanism of action", *Biochimica et Biophysica Acta 1994*, vol. 1189, No. 2, especially pp. 195-197, Jan. 19, 1994, 195-203.

Zhou, Xiaohuai et al., "Lipophilic Polylysines Mediate Efficient DNA Transfection in Mammalian Cells", *Biochimica et Biophysica Acta*, vol. 1065, 1991, 8-14.

Zhu, Zhen et al., "Transformation of tobacco protoplasts with DNA entrapped in pH-sensitive liposomes", *Plant Cell, Tissue and Organ Culture*, vol. 22,, 1990, 135-145.

US 7,189,874, 03/2007, Chu et al. (withdrawn)

\* cited by examiner

TRANSFECTION REAGENTS

CROSS-REFERENCE TO RELATED APPLICATIONS

This application is a continuation of U.S. application Ser. No. 13/420,091, filed Mar. 14, 2012, which application is a continuation of U.S. application Ser. No. 12/353,371 filed Jan. 14, 2009, which application is a continuation of U.S. application Ser. No. 11/040,687, filed Jan. 21, 2005, now U.S. Pat. No. 7,479,573, which is a continuation of U.S. application Ser. No. 09/438,365, filed Nov. 12, 1999, now U.S. Pat. No. 7,166,745, which claims the benefit under 35 U.S.C. §119(e) of U.S. provisional application Ser. No. 60/108,117, filed Nov. 12, 1998, the disclosures of which applications are incorporated herein by reference in their entirety.

BACKGROUND OF THE INVENTION

1. Field of the Invention

The present invention relates to cationic lipids and compositions of cationic lipids having utility in lipid aggregates for delivery of macromolecules and other compounds into cells.

2. Related Art

Lipid aggregates such as liposomes have been found to be useful as agents for delivery to introduce macromolecules, such as DNA, RNA, protein, and small chemical compounds such as pharmaceuticals, to cells. In particular, lipid aggregates comprising cationic lipid components have been shown to be especially effective for delivering anionic molecules to cells. In part, the effectiveness of cationic lipids is thought to result from enhanced affinity for cells, many of which bear a net negative charge. Also in part, the net positive charge on lipid aggregates comprising a cationic lipid enables the aggregate to bind polyanions, such as nucleic acids. Lipid aggregates containing DNA are known to be effective agents for efficient transfection of target cells.

The structure of various types of lipid aggregates varies, depending on composition and method of forming the aggregate. Such aggregates include liposomes, unilamellar vesicles, multilameller vesicles, micelles and the like, having particular sizes in the nanometer to micrometer range. Methods of making lipid aggregates are by now well-known in the art. The main drawback to use of conventional phospholipid containing liposomes for delivery is that the material to be delivered must be encapsulated and the liposome composition has a net negative charge which is not attracted to the negatively charged cell surface. By combining cationic lipid compounds with a phospholipid, positively charged vesicles and other types of lipid aggregates can bind DNA, which is negatively charged, can be taken up by target cells, and can transfect target cells. (Felgner, P. L. et al. (1987) Proc. Natl. Acad. Sci. USA 84:7413-7417, Eppstein, D. et al., U.S. Pat. No. 4,897,355.)

A well-known cationic lipid is N-[1-(2,3-dioleoyloxy)propyl]-N,N,N-trimethylammonium chloride (DOTMA). The structure of DOTMA is:

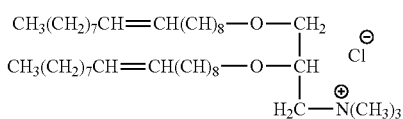

DOTMA by itself or in 1:1 combination with dioleoylphosphatidylethanolamine (DOPE) is formulated into liposomes using standard techniques. Feigner, et al. supra demonstrated that such liposomes provided efficient delivery of nucleic acids to some types of cells. A DOTMA:DOPE (1:1) formulation is sold under the trade name LIPOFECTIN (Life Technologies. Inc., Rockville, Md.). Another commercially available cationic lipid is 1,2-bis(oleoyloxy)-3-3-(trimethylammonia) propane (DOTAP), which differs from DOTMA only in that the oleoyl moieties are linked via ester, rather than ether bonds to the propylamine. A related group of compounds differ from DOTMA and DOTAP in that one of the methyl groups of the trimethylammonium group is replaced by a hydroxyethyl group. Compounds of this type are similar to the Rosenthal Inhibitor (RI) of phospholipase A (Rosenthal, A. F. and Geyer, R. P. (1960) J. Biol. Chem. 235:2202-2206) which has stearoyl esters linked to the propylamine core. The dioleoyl analogs of RI are commonly abbreviated as DORI-ether and DORI-ester, depending on the linkage of the fatty acid moieties to the propylamine core. The hydroxy group can be used as a site for further functionalization.

The dimyristyloxy analog of RI is known as DRMIE. A 1:1 (M/M) DMRIE:cholesterol formulation is sold under the trade name DMRIE-C (Life Technologies, Inc., Rockville. Md.). The structure of DMRIE is:

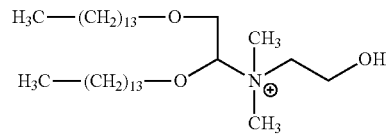

Another class of compounds has been disclosed by Behr et al. (1989) Proc. Natl. Acad. Sci. USA 86:6982-6986; EPO publication 0 394 111 (Oct. 24, 1990), in which carboxyspermine has been conjugated to two types of lipids. The structure of 5-carboxyspermylglycine dioctadecylamide (DOGS) is:

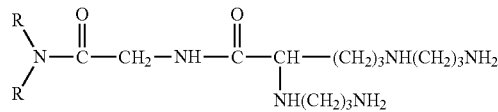

R = CH$_3$(CH$_2$)$_{17}$

The structure of dipalmitoylphosphatidylethanolamine 5-carboxyspermylamide (DPPES) is:

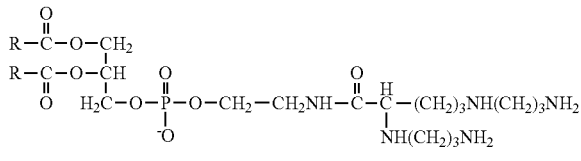

R = CH$_3$(CH$_2$)$_{15}$

Both DOGS and DPPES have been used to coat plasmids, forming a lipid aggregate complex that provides efficient transfection. The compounds are claimed to be more efficient and less toxic than DOTMA for transfection of some cell lines. DOGS is available commercially as TRANSFECTAM™ (Promega. Madison. Wis.).

Another class of compounds has been also described in which carboxy spermine has been conjugated to lipids via an amide bond (Gebeyehu, G. et al., U.S. Pat. No. 5,334,761). These compounds are useful for an efficient delivery of nucleic acids into various cells and also are intermediates for making other such lipids. 2,3-di-oleyloxy-N-[2(spermine-carboxamido)ethyl]-N,N-dimethyl-1-propan-aminium (DOSPA) is available as a 3:1 (w/w) formulation with DOPE under the trade name LIPOFECTAMINE® (available from Life Technologies, Inc., Rockville, Md.). The structure of DOSPA is as follows:

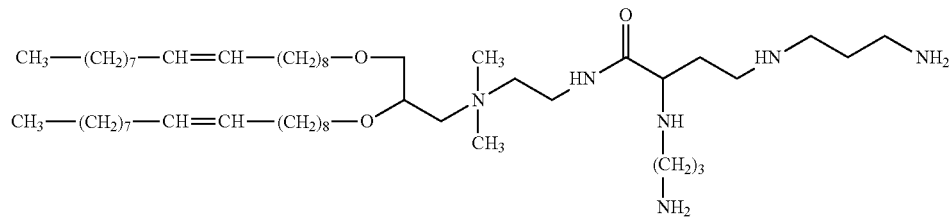

Lipid compounds with a spermine head group have also been described (Haces, A., et al., U.S. Pat. No. 5,674,908). These compounds are especially useful for delivery of nucleic acids into insect cells. A 1:1.5 (M/M) formulation of tetramethyltetrapalmitylspermine (TM-TPS) to DOPE is commercially available under the trade name CELLFECTIN® (Life Technologies, Inc., Rockville, Md.). The structure of TM-TPS is shown below:

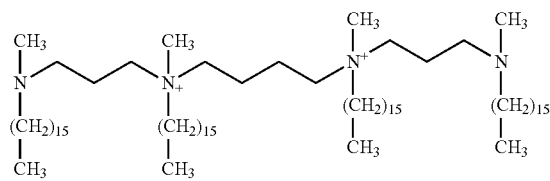

A cationic cholesterol derivative (DC-Chol) has been synthesized and formulated into liposomes in combination with DOPE. (Gao, X. and Huang, L. (1991) Biochim. Res. Comm. 179:280-285). The compound's structure is:

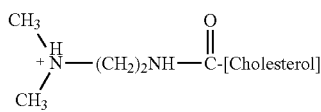

Liposomes formulated with DC-Chol are said to provide more efficient transfection and lower toxicity than DOTMA-containing liposomes for some cell lines.

Lipopolylysine, formed by conjugating polytysine to DOPE, has been reported to be especially effective for transfection in the presence of serum, a condition likely to be encountered in vivo (Zhou, X. et al. (1991) Biochim. Biophys. Acta 1065: 8-14).

Despite advances in the field, a need remains for a variety of improved cationic lipid compounds. In particular, no single cationic lipid to date has been found to work well with all cell types. Since different cell types differ from one another in membrane composition, it is not surprising that different compositions and types of lipid aggregates are effective for different cell types, either for their ability to contact and fuse with target cell membranes, or for aspects of the transfer process itself. At present these processes are not well understood, consequently the design of effective liposomal precursors is largely empirical. Besides content and transfer, other factors are of importance, for example, ability to form lipid aggregates suited to the intended purpose, the possibility of transfecting cells in the presence of serum-toxicity to the target cell, stability as a carrier for the compound to be delivered, and ability to function in an in vivo environment. In addition, lipid aggregates can be improved by broadening the range of substances which can be delivered to cells. The cationic lipid compounds of the present invention have improved function with respect to several of the foregoing attributes.

SUMMARY OF THE INVENTION

The present invention provides novel cationic lipids according to the general Formula (A):

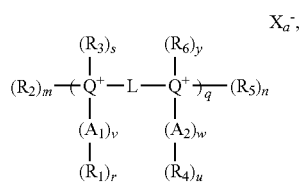

wherein

Q is selected from the group consisting of N, O and S; L is any bivalent organic radical capable of covatently linking each Q, such as C, CH, $(CH_2)_l$ or $\{(CH_2)_i-Y-\{(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by —$X_1$-L'-$X_2$—Z or —Z;

$R_1$-$R_6$, independently of one another, are selected from the group consisting of H, —$\{CH_2\}_p$-D-Z, an alkyl, an alkenyl, an aryl, and an alkyl or alkyl ether optionally substituted by one or more of an alcohol, an amino alcohol, an amine, an amide, an ether, a polyether, a polyamide, an ester, a mercaptan, an alkylthio, a urea, a thiourea, a guanidyl, or a carbamoyl group, and wherein at least one of $R_1$, $R_3$, $R_4$ and $R_5$ is a straight chain or branched, cyclic, alkyl, alkenyl, alkynyl or aryl group; and any one or more of $R_1$, $R_3$, $R_4$ and $R_6$ may optionally be covalently linked with each other, with Y or with L when L is C or CH to form a cyclic moiety;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, peptide, and protein;

$X_1$ and $X_2$, independently of one another, are selected from the group consisting of NH, O, S, alkylene, and arylene;

L' is selected from the group consisting of alkylene, alkenylene, alkynylene, arylene, alkylene ether, and polyether;

D is Q or a bond;

$A_1$ and $A_2$, independently of one another, are selected from the group consisting of $CH_2O$, $CH_2S$, $CH_2NH$, $C(O)$, $C(NH)$, $C(S)$ and $(CH_2)_t$;

X is a physiologically acceptable anion;

m, n, r, s, u, v, w and y are 0 or 1, with the proviso that when both m and n are 0 at least one of r, s, u and y is other than 0;

i, j, k, l, p and t are from a to about 100;

q is an integer from 1 to about 1000; and a is the number of positive charge divided by the valence of the anion.

Further, the present invention provides novel cationic lipids according to the general Formula (B):

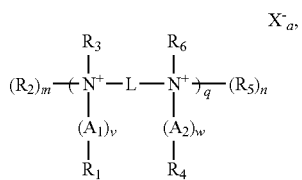

wherein

L is $(CH_2)_l$ or $\{(CH_2)_i-Y-(CH_2)_j\}_k$ wherein Y is selected from the group consisting of an ether, a polyether, an amide, a polyamide, an ester, a sulfide, a urea, a thiourea, a guanidyl, a carbamoyl, a carbonate, and a secondary amino group;

$R_1$-$R_6$, independently of one another, are selected from the group consisting of H, $-(CH_{2p}-Z$, an alkyl, an alkenyl, an aryl, and an alkyl or an alkyl ether optionally substituted by one or more of an alcohol, an aminoalcohol an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group, preferably having from about 2 to 100, preferably 4 to 75, more preferably 6 to 64, more preferably 8 to 50, more preferably 8 to 40, more preferably 8 to 30, more preferably 6 to 30, more preferably 4 to 30, more preferably 2 to 30, and most preferably 8 to about 24 carbon atoms, and anyone or more of $R_1$, $R_3$, $R_4$ and/or $R_6$ may optionally be covalently linked with each other to form a cyclic moiety;

Z is selected from the group consisting of amine, spermiyl, carboxyspermiyl guanidyl, spemlidinyl, putricinyl, diaminoalkyl, pyridyl, piperidinyl, pyrrolidinyl, polyamine, amino acid, amino acid derivative, peptide, and protein;

$A_1$ and $A_2$, independently of one another, are selected from the group consisting of $CH_2O$, $CH_2S$, $CH_2NH$, $C(O)$, $C(NH)$, $C(S)$ and $(CH_2)$t;

X is a physiologically acceptable anion, such as the halide anions, chloride, bromide, and iodide as well as acetate, sulfate, trifluoroacetate, etc.;

m, n, v and w are 0 or 1;

i, j, k, l, p and t are integers from 1 to about 100, more preferably 1 to 50, more preferably 1 to 25, more preferably 1 to 15, more preferably 1 to 10 and most preferably 1 to about 4;

q is an integer from 1 to about 1000, preferably from 1 to about 500, more preferably from 1 to about 250, more preferably from 1 to about 100, more preferably from 1 to about 50, more preferably from 1 to about 25, more preferably from 1 to about 12, most preferably from 1 to about 6; and a is the number of positive charges divided by the valence of the anion, wherein when m and n are 0, then a is O.

Also, the present invention provides novel cationic lipids according to the Formula (C):

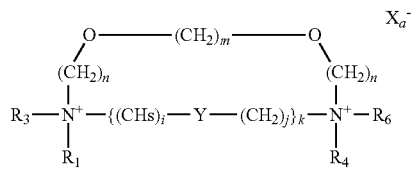

wherein

Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $-X_1$-L'-$X_2$-Z or -Z;

$R_1$, $R_3$, $R_4$ and $R_6$, independently of one another, are selected from the group consisting of H, $-\{CH_2\}_p$-D-Z, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group, most preferably having from about 8 to about 24 carbon atoms, and $R_1$, $R_3$, $R_4$ and $R_5$ may optionally be covalently linked with each other or with Y, to form a cyclic moiety;

Z is selected from the group consisting of amine, spemliyl, carboxyspemliyl, guanidyl, spemlidinyl, putricinyl, diaminoalkyl, pyridyl, piperidinyl, pyrrolidinyl, polyamine, amino acid, peptide, and protein;

$X_1$ and $X_2$, independently of one another, are selected from the group consisting of NH, O, S, alkylene, and arylene;

L' is selected from the group consisting of alkylene, alkenylene, alkynylene, arylene, alkylene ether, and polyether;

D is Q or a bond;

m and n are 0 or 1; and i, j, k, l and p are integers from 1 to about 10.

Further, the present invention provides compounds or polycations according to the Formula (D):

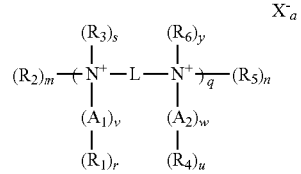

wherein

L is C, CH, $(CH_2)_l$ or $\{(CH_2)_i-Y-(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $-X_1$-L'-$X_2$-Z or -Z;

$R_1$-$R_6$, independently of one another, are selected from the group consisting of H, —$(CH_2)_p$-D-Z, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and wherein at least one of $R_1$, $R_3$, $R_4$ and $R_6$ is a straight chain or branched, cyclic, alkyl, alkenyl, alkynyl or aryl groups, preferably having from about 2 to about 30 carbon atoms, more preferably from 8 to 24 carbon atoms;

Z is selected from the group consisting of amine, spenniyl, carboxyspenniyl, guanidyl, spennidinyl, putricinyl, diaminoalkyl, pyridyl, piperidinyl, pyrrolidinyl, polyamine, amino acid, amino acid derivative, peptide, and protein;

$X_1$ and $X_2$, independently of one another, are selected from the group consisting of NH, O, S, alkylene and arylene;

L' is selected from the group consisting of alkylene, alkenylene, alkynylene, arylene, alkylene ether, and polyether;

$A_1$ and $A_2$, independently of one another, are selected from the group consisting of $CH_2O$, $CH_2S$, $CH_2NH$, $C(O)$, $C\{NH\}$, $C(S)$ and $(CH_2)t$;

m, n, r, s, u, v, w and y are 0 or 1, with the proviso that when both m and n are 0 at least one of r, s, u and y is other than 0;

i, j, k, l, p and t are integers from 0 to about 100; and q is an integer from 1 to about 1000.

Also, the present invention provides compounds or polycations according to the Formula (E):

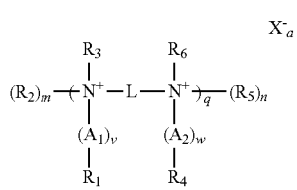

wherein

L is $(CH_2)_l$ or $\{(CH_2)_i—Y—(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, and a secondary amino group;

$R_1$, $R_6$, independently of one another, are selected from the group consisting of H, —$(CH_2)_p$—Z, an alkyl, an alkenyl, an aryl, and an alkyl or an alkyl ether optionally substituted by one or more of an alcohol, an amino alcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkenyl or aryl group, preferably having from about 2 to about 30 carbon atoms, more preferably having from about 8 to about 24 carbon atoms;

Z is selected from the group consisting of amine, spenniyl, carboxyspenniyl, guanidyl, spennidinyl, putricinyl, diaminoalkyl, pyridyl, piperidinyl, pyrrolidinyl, polyamine, amino acid, amino acid derivative, peptide, and protein;

$A_1$ and $A_2$, independently of one another, are selected from the group consisting of $CH_2O$, $CH_2S$, $CH_2NH$, $C(O)$, $C(NH)$, $C(S)$ and $(CH_2)t$;

m, n, v and w are 0 or 1;

i, j, k, l, p and t are integers from 1 to about 100; and q is an integer from 1 to about 1000.

Also, the present invention provides novel compounds falling within the scope of the above formulae.

The compounds of the invention are useful, either alone or in combination with other lipid aggregate-forming components (e.g., DOPE, DOPC or cholesterol) for formulation into liposomes or other lipid aggregates. Such aggregates are polycationic, able to form stable complexes with anionic macromolecules, such as nucleic acids. The lipid aggregate macromolecular complex interacts with cells making the polyanionic macromolecule available for absorption and uptake by the cell.

The present invention provides a lipid aggregate comprising one or more of the compounds of the present invention. Preferably, the lipid aggregate comprises at least one lipid aggregate-forming compound. Preferably, the lipid aggregate-forming compound is selected from the group consisting of DOPE, DOPC and cholesterol.

The compounds of the present invention may also be conjugated to or mixed with or used in conjunction with a variety of useful molecules and substances such as proteins, peptides, growth factors and the like to enhance cell-targeting, uptake, internalization, nuclear targeting and expression.

This invention also includes lipid aggregates comprising one or more compounds of the present invention or mixtures thereof. Such lipid aggregates may be combined with one or more aggregate-forming components and/or transfection enhancers.

The transfection methods of the present invention employing the compounds or compositions (such as those described above) of the present invention or mixtures thereof can be applied to in vitro and in vivo transfection of cells, particularly to transfection of eukaryotic cells or tissues including animal cells, human cells, insect cells, plant cells, avian cells, fish cells, mammalian cells and the like.

Accordingly, the present invention provides a method for introducing a polyanion into a cell or cells, wherein the method comprises forming a liposome from a positively charged compound according to the invention, contacting the liposome with polyanion to form a positively-charged polyanion-liposome complex and incubating the complex with a cell or cells.

The methods of this invention can be used to generate transfected cells or tissues which express useful gene products. The methods of this invention can also be used as a step in the production of transgenic animals. The methods of this invention are useful in any therapeutic method requiring introducing of nucleic acids into cells or tissues. In particular, these methods are useful in cancer treatment, in in vivo and ex vivo gene therapy, and in diagnostic methods. See, for example, U.S. Pat. No. 5,589,466 to Felgner, et al. and U.S. patent application Ser. No. 08/450,555 filed on May 25, 1995 to Jessee, et al. The transfection compounds or compositions of this invention can be employed as research reagents in any transfection of cells or tissues done for research purposes. Nucleic acids that can be transfected by the methods of this invention include DNA and RNA from any source comprising natural bases or non-natural bases, and include those encoding and capable of expressing therapeutic or otherwise useful proteins in cells or tissues, those which inhibit expression of nucleic acids in cells or tissues, those which inhibit enzymatic activity or activate enzymes, those which catalyze reactions (ribozymes), and those which function in diagnostic assays.

The compounds, compositions and methods provided herein can also be readily adapted in view of the disclosure herein to introduce biologically active macromolecules or substances other than nucleic acids, including, among others, polyamines, polyamine acids, polypeptides, proteins, biotin, and polysaccharides into cells. Other useful materials for example, therapeutic agents, diagnostic materials and research reagents, can be introduced into cells by the methods of this invention. In a preferred aspect, any nucleic acid vector may be delivered to or into a cell by the present invention.

Accordingly, the present invention provides a method for introducing a biologically active substance into a cell, wherein the method comprises forming a liposome of a compound according to the invention and a biologically active substance and incubating the liposome with a cell or cell culture.

The invention also relates to compositions comprising the compounds of the invention and one or more additional components selected from the group consisting of nucleic acids, cells, buffers, culture media, biologically active substance, neutral lipids, and transfection enhancers, preferably a nucleic acid.

This invention also includes transfection kits which include one or more of the compounds or compositions of the present invention or mixtures thereof. Particularly, the invention provides a kit comprising one or more of the compounds of the present invention and at least one additional component selected from the group consisting of a cell, cells, a cell culture media, a nucleic acid, a transfection enhancer and instructions for transfecting a cell or cells.

The invention also relates to intermediates and methods for using such intermediates for making the compounds or compositions of the invention. The invention also relates to the compositions, compounds or components obtained by the interaction of materials (intermediates, compounds, lipids etc.) used in the synthesis methods of the invention.

Other preferred embodiments of the present invention will be apparent to one of ordinary skill in the art in view of the following drawings and description of the invention.

DETAILED DESCRIPTION OF THE PREFERRED EMBODIMENTS

Figure 1:
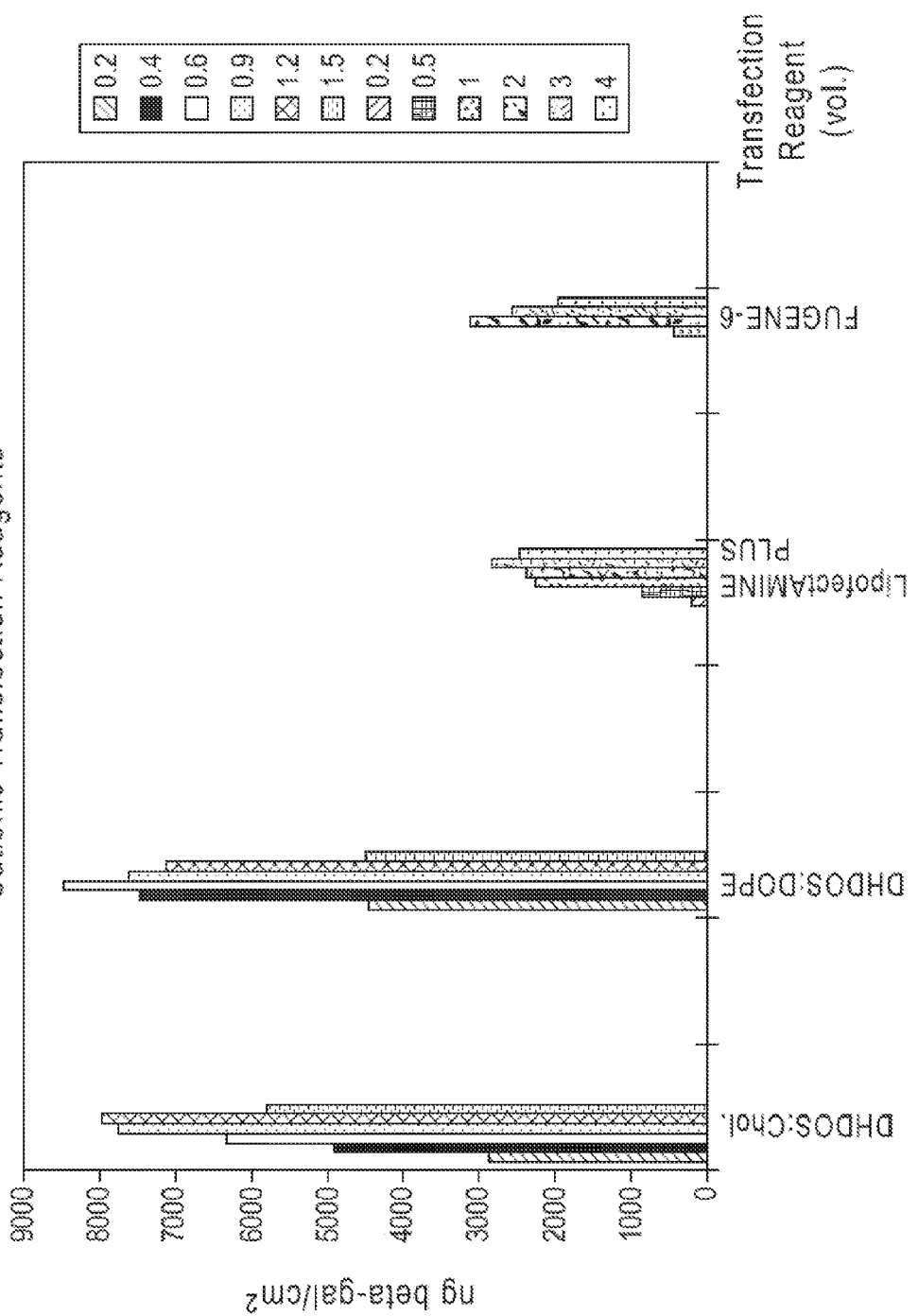
FIG. 1 is a graph showing the transfection of HEK-293 cells with cationic transfection reagents.

The present invention relates to cationic lipids and compositions of cationic lipids having utility in lipid aggregates for delivery of macromolecules and other compounds into cells. The compounds can be used alone or in combination with other compounds to prepare liposomes and other lipid aggregates suitable for transfection or delivery of compounds to target cells, either in vitro or in vivo.

The compounds of the present invention are preferably polycationic and preferably thus form highly stable complexes with various anionic macromolecules, particularly polyanions such as nucleic acids. These compounds have the property, when dispersed in water, of forming lipid aggregates which associate strongly, via their cationic portion, with polyanions. By using an excess of cationic charges relative to the anionic compound, the polyanion-lipid complexes may be adsorbed on cell membranes, thereby facilitating uptake of the desired compound by the cells.

The present invention also relates to intermediates for preparing the compound and compositions of the invention.

More specifically, the present invention relates to a cationic lipid for transfection which has a greater transfection efficiency than commercially available products in the three most common cell types used in expression research (CHO-KI, COS-7, and HEK293) making it useful for high throughput applications; and which has a simple to use protocol as defined by the fact that no additional reagents are required (e.g., such as 10 LIPOFECTAMINE® PLUS™ Reagent available from Life Technologies, Inc., Rockville, Md.), no removal of serum and therefore no media changes are required, and the DNA/lipid complex do not need to be removed from the cells prior to assay.

The compounds according to the present invention have the Formula (A):

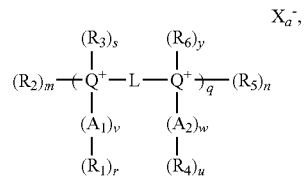

wherein

Q is selected from the group consisting of N, O and S;

L is any bivalent organic radical capable of covalently linking each Q, such as C, CH, $(CH_2)_i$ or $\{(CH_2)_i-Y-(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $-X_1-L'-X_2-Z$ or $-Z$;

$R_1$ $R_6$, independently of one another, are selected from the group consisting of H, $-(CH_2)_p$-D-Z, an alkyl, an alkenyl, an aryl, and an alkyl or alkyl ether optionally substituted by one or more of an alcohol, an amino alcohol, an amine, an amide, an ether, a polyether, a polyamide, an ester, a mercaptan, an alkylthio, a urea, a thiourea, a guanidyl, or a carbamoyl group, and wherein at least one of $R_1$, $R_3$, $R_4$ and $R_6$ is a straight chain or branched, cyclic, alkyl, alkenyl, alkynyl or aryl group; and $R_1$ and $R_4$ or $R_3$ and $R_6$ may optionally be covalently linked with each other, with Y or with L when L is C or CH to form a cyclic moiety;

Z is selected from the group consisting of amine, spermiyl, carboxyspermiyl, guanidyl, spennidinyl, putricinyl, diaminoalkyl, pyridyl, piperidinyl, pyrrolidinyl, polyamine, amino acid, peptide, and protein;

$X_1$ and $X_2$, independently of one another, are selected from the group consisting of NH, O, S, alkylene, and arylene;

L' is selected from the group consisting of alkylene, alkenylene, alkynylene, arylene, alkylene ether, and polyether;

D is Q or a bond;

$A_1$ and $A_2$, independently of one another, are selected from the group consisting of $CH_2O$, $CH_2S$, $CH_2NH$, $C(O)$, $C(NH)$, $C(S)$ and $(CH_2)t$;

X is a physiologically acceptable anion;

m, n, r, s, u, v, w and y are 0 or 1, with the proviso that when both m and n are 0 at least one of r, s, u and y is other than 0;

i, j, k, l, p and t are integers from 0 to about 100;

q is an integer from 1 to about 1000; and a is the number of positive charge divided by the valence of the anion.

Preferably the alkyl ether optionally substituted by one or more alcohol groups comprises a carbohydrate. Preferably, the carbohydrate is selected from the group consisting of galactose, fructose, glucose, maltose, sucrose, cellobiose, lactose, mannose, glucopyranose, mannopyranose and galactopyranose.

Preferably, i, j, k, l, p and t are integers independently selected from 1 to 100, more preferably from 1 to 50, more preferably 1 to 25, more preferably 1 to 15, more preferably 1 to 10 and most preferably 1 to about 4. Preferably, 1, b and c are integers from 1 to about 4, i and j are integers from about 2 to about 3 and k is an integer from 1 to about 3.

Preferably, q is an integer from 1 to about 500, more preferably from 1 to about 250, more preferably from 1 to about 100, more preferably from 1 to about 50, more preferably from 1 to about 25, more preferably from 1 to about 12, most preferably from 1 to about 6.

Preferably, at least one of $R_1$, $R_3$, $R_4$ and $R_6$ is a straight chain or branched, cyclic, alkyl, alkenyl, alkynyl or aryl group having from about 2 to 100, preferably 4 to 75, more preferably 6 to 64, more preferably 8 to 50, more preferably 8 to 40, more preferably 8 to 30, more preferably 6 to 30, more preferably 4 to 30, and most preferably 8 to about 24 carbon atoms.

In all aspects of the invention, most suitable R1 and R4 groups, which can be the same or different, preferably the same, are $C_{6-30}$ hydrocarbon radicals derived from fatty acids or activated derivatives thereof, such as fatty acyl chlorides. Thus, typical $R_1$ and $R_4$ groups are $C_{6-30}$ alkyl or alkenyl groups.

Preferably, $R_1$, $R_2$, $R_3$, $R_4$, $R_5$ and $R_6$, independently of one another, are selected from the group consisting of H, $C_1$-$C_8$ alkyl, alkenyl, aryl, and alkyl optionally substituted by one or more of an alcohol, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group having from about 8 to about 24 carbon atoms.

Preferably Q is N.

Preferably, Y is selected from the group consisting of $CH_2$, O, S and NH.

Useful compounds falling within the scope of the above formula (A) include compounds having the following formulae:

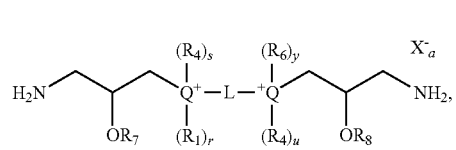

(A1)

wherein

Q and L are as defined above;

$R_1$, $R_3$, $R_4$ and $R_6$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

r, s, u and y are 0 or 1; and $R_7$ and $R_8$ are independently H or a carbohydrate;

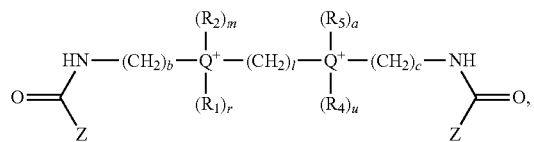

(A2)

wherein

Q is as defined above;

$R_1$, $R_2$, $R_4$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

Z is selected from the group consisting of spermiyl, spermidiyl, amino acid, peptidyl, diaminoalkyl, and polyamine;

m, n, r and u are 0 or 1; and l, b and c are integers independently selected from 1 to about 4;

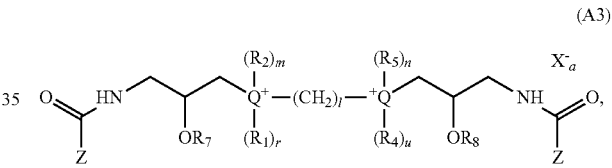

(A3)

wherein

Q, $R_1$, $R_4$, m, n, r and u are as defined above;

$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

Z is selected from the group consisting of spermiyl, spermidiyl, amino acid, peptidyl, diaminoalkyl, and polyamine;

$R_7$ and $R_8$ are independently H or a carbohydrate; and l is an integer from 1 to about 4;

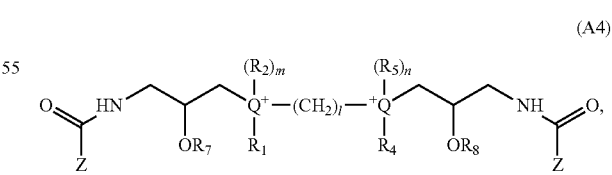

(A4)

wherein

Q is as defined above, preferably N;

at least one of $R_1$ and $R_4$ are straight chain or branched, cyclic, alkyl, alkenyl, alkynyl or aryl groups having from about 8 to about 24 carbon atoms;

$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

Z is selected from the group consisting of spermiyl, spermidiyl, amino acid, peptidyl, diaminoalkyl, and polyamine;

$R_7$ and $R_8$ are independently H or a carbohydrate, preferably H;

m and n are as defined above; and is an integer from 1 to about 4;

Y is selected from the group consisting of $CH_2$, O, S and NH;

(A7)

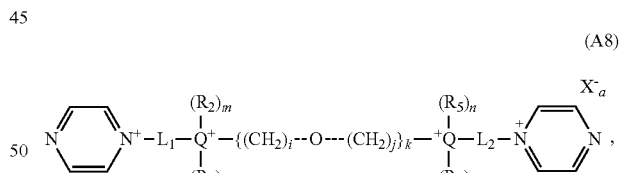

(A5)

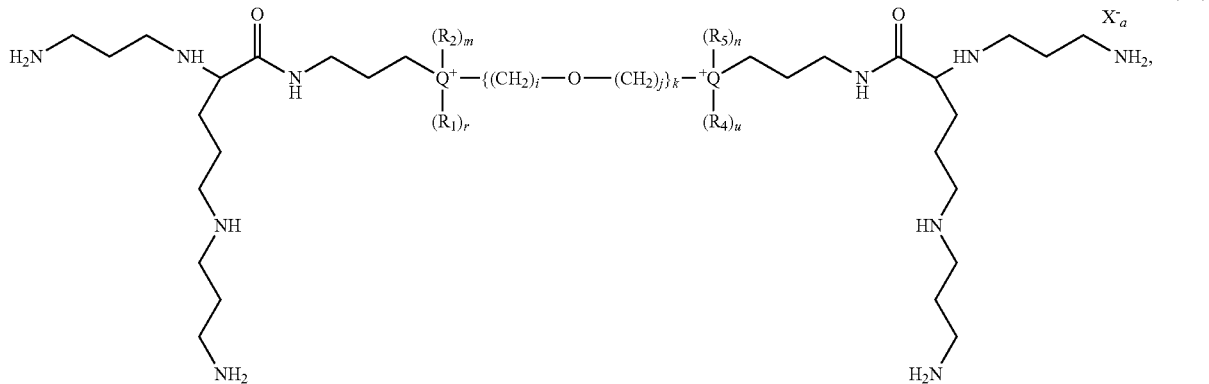

wherein $Q, R_1, R_4, r, u, m$ and n are as defined above:

$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

i and j are integers from about 2 to about 3; and k is an integer from 1 to about 3;

wherein $Q, R_1, R_4, r, u, m$ and n are as defined above;

$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

i and j are integers from about 2 to about 3;

k is an integer from 1 to about 3;

$L_1$ and $L_2$, independently from one another, are an alkylene or an alkylene ether; Y is selected from the group consisting of $CH_2$, O, S and NH;

(A6)

(A8)

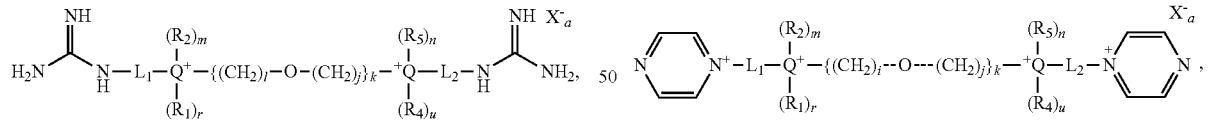

wherein $Q, R_1, R_4, r, u, m$ and n are as defined above;

$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

i and j are integers from about 2 to about 3;

k is an integer from 1 to about 3;

$L_1$ and $L_2$, independently from one another, are an alkylene or an alkylene ether;

wherein $Q, R_1, R_4, r, u, m$ and n are as defined above;

$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

i and j are integers from about 2 to about 3;

k is an integer from 1 to about 3;

$L_1$ and $L_2$, independently from one another, are an alkylene or an alkylene ether;

Y is selected from the group consisting of $CH_2$, O, S and NH;

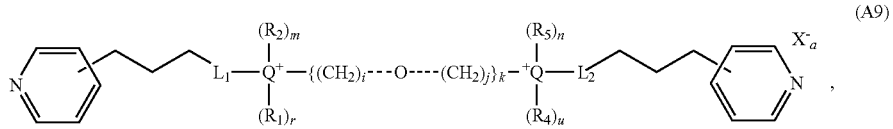

(A9)

wherein

Q, $R_1$, $R_2$, r, u, m and n are as defined above;

$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

i and j are integers from about 2 to about 3;

k is an integer from 1 to about 3;

$L_1$ and $L_2$, independently from one another, are an alkylene or an alkylene ether;

Y is selected from the group consisting of $CH_2$, O, S and NH; and an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group, and anyone or more of $R_1$, $R_4$, $R_3$ and $R_6$ may optionally be covalently linked with each other to form a cyclic moiety;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, peptide, and protein;

$A_1$ and $A_2$, independently of one another, are selected from the group consisting of $CH_2O$, $CH_2S$, $CH_2NH$, $C(O)$, $C(NH)$, $C(S)$ and $(CH_2)_t$;

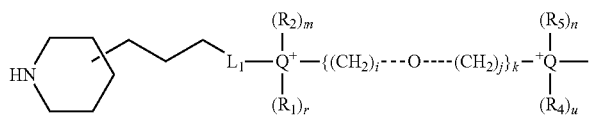

(A10)

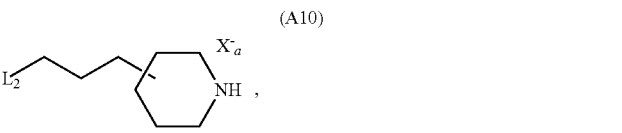

wherein

Q, $R_1$, $R_4$, r, u, m, and n are as defined above;

$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

i and j are integers from about 2 to about 3;

k is an integer from 1 to about 3;

$L_1$ and $L_2$, independently from one another, are an alkylene or an alkylene ether;

Y is selected from the group consisting of $CH_2$, O, S and NH.

Also, compounds of the present invention have the Formula (B):

X is a physiologically acceptable anion;

m, n, v and w are 0 or 1;

i, j, k, l, p and t are integers from 1 to about 100;

q is an integer from 1 to about 1000; and a is the number of positive charge divided by the valence of the anion, wherein when m and n are 0, then a is 0.

Preferably, $R_1$-$R_6$, i, j, k, l, p, t, q, b and c are as defined with reference to Formula (A).

Preferably, Y is selected from the group consisting of $CH_2$, O, S and NH.

Useful compounds falling within the scope of the Formula (B) include compounds having the following formulae:

(B1)

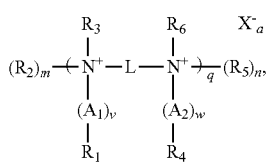

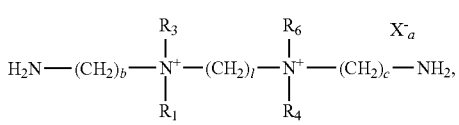

wherein

L is $(CH_2)_l$ or $\{(CH_2)_i—Y—(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, and a secondary amino group;

$R_1$-$R_6$, independently of one another, are selected from the group consisting of H, —$(CH_2)_p$—Z, an alkyl, an alkenyl, an aryl, and an alkyl or alkyl ether optionally substituted by one or more of an alcohol, an aminoalcohol, an amine, an amide, wherein $R_1$, $R_3$, $R_4$ and $R_6$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group having from about 8 to about 24 carbon atoms; and l, b and c are integers independently selected from 1 to about 4;

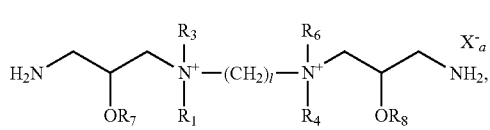

(B2)

wherein $R_1$, $R_3$, $R_4$ and $R_6$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group having from about 8 to about 24 carbon atoms;

$R_7$ and $R_8$ are independently H or a carbohydrate; and
l is an integer from 1 to about 4;

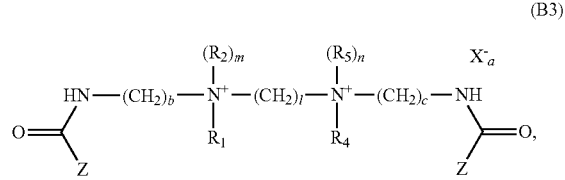

(B3)

wherein $R_1$, $R_2$, $R_4$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group, and at least one of $R_1$, $R_2$, $R_3$ and $R_5$ is a straight chain or branched, cyclic, alkyl, alkenyl, alkynyl or aryl group having from about 8 to about 24 carbon atoms;

Z is selected from the group consisting of spermiyl, spermidiyl, amino acid, peptidyl, diaminoalkyl, and polyamine;
m and n are 0 or 1; and
l, b and c are integers independently selected from 1 to about 4;

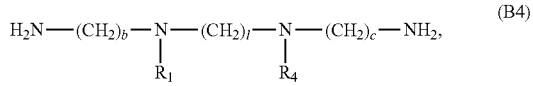

(B4)

wherein at least one of $R_1$ and $R_4$ is a straight chain or branched, cyclic, alkyl, alkenyl, alkynyl or aryl group having from about 8 to about 24 carbon atoms; and
l, b and c are integers independently selected from 1 to about 4;

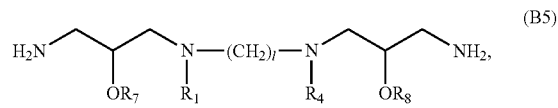

(B5)

wherein at least one of $R_1$ and $R_4$ are straight chain or branched, cyclic, alkyl, alkenyl, alkynyl or aryl groups having from about 8 to about 24 carbon atoms; $R_7$ and $R_8$ are independently hydrogen or a carbohydrate, preferably hydrogen; and
l is an integer from 1 to about 4;

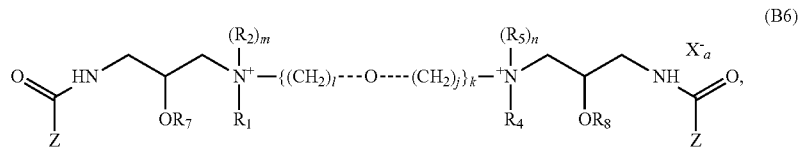

(B6)

wherein

Z is as defined above;
at least one of $R_1$ and $R_4$ is a straight chain or branched, cyclic, alkyl, alkenyl, alkynyl or aryl group having from about 8 to about 24 carbon atoms;
$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
$R_7$ and $R_8$ are independently H or a carbohydrate;
m and n are 0 or 1;
i and j are integers from about 2 to about 3; and
k is an integer from 1 to about 3;

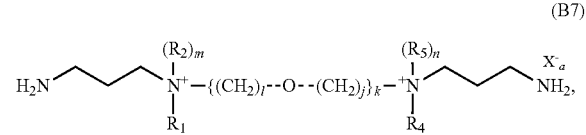

(B7)

wherein at least one of $R_1$ and $R_4$ is a straight chain or branched, cyclic, alkyl, alkenyl, alkynyl or aryl group having from about 8 to about 24 carbon atoms;
$R_2$ and $R_5$, independently of one another, are selected from the group consisting of H and a $C_1$ $C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
m and n are 0 or 1;
i and j are integers from about 2 to about 3; and
k is an integer from 1 to about 3;

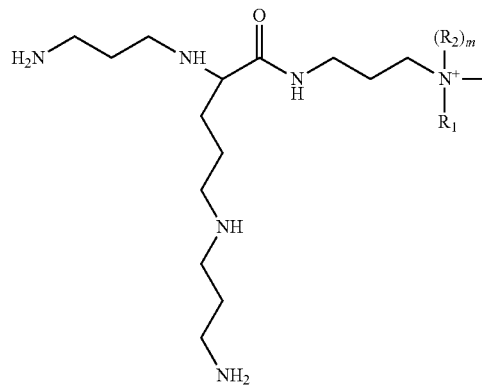

(B8)

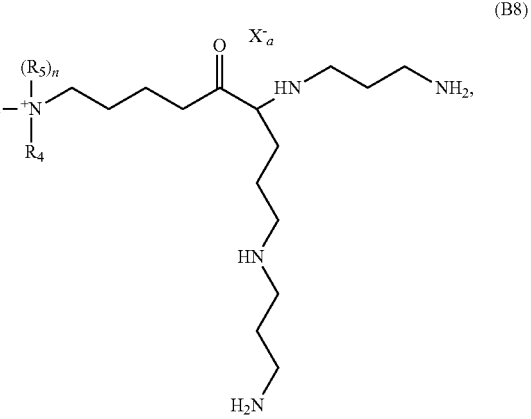

wherein
at least one of $R_1$ and $R_4$ is a straight chain or branched, cyclic, alkyl, alkenyl, alkynyl or aryl group having from about 8 to about 24 carbon atoms;
$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl or a carbamoyl group;
m and n are 0 or 1;
i and j are integers from about 2 to about 3; and
k is an integer from 1 to about 3;

wherein
at least one of $R_1$ and $R_4$ is a straight chain or branched, cyclic, alkyl, alkenyl, alkynyl or aryl group having from about 8 to about 24 carbon atoms;
$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
m and n are 0 or 1;
i and j are integers from about 2 to about 3;
k is an integer from 1 to about 3;
$L_1$ and $L_2$, independently from one another, are an alkylene or an alkylene ether;
Y is selected from the group consisting of $CH_2$, O, S and NH;

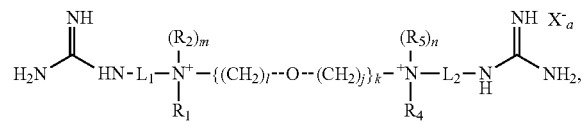

(B9)

wherein
at least one of $R_1$ and $R_4$ is a straight chain or branched, cyclic, alkyl, alkenyl, alkynyl or aryl group having from about 8 to about 24 carbon atoms;
$R_2$ and $R_5$, independently of one another, are selected from the group consisting of H and a C1 C8 alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
m and n are 0 or 1;
i and j are integers from about 2 to about 3;
k is an integer from 1 to about 3;
$L_1$ and $L_2$, independently from one another, are an alkylene or an alkylene ether:
Y is selected from the group consisting of $CH_2$, O, S and NH;

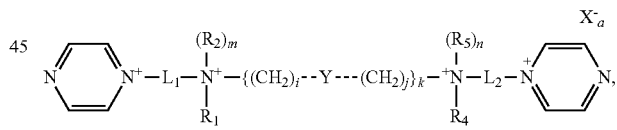

(B11)

wherein
at least one of $R_1$ and $R_4$ is a straight chain or branched, cyclic, alkyl, alkenyl, alkynyl or aryl group having from about 8 to about 24 carbon atoms;
$R_2$ and $R_5$, independently of one another, are selected from the group consisting of H and a $C_1$ $C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;
m and n are 0 or 1;
i and j are integers from about 2 to about 3;
k is an integer from 1 to about 3;
$L_1$ and $L_2$, independently from one another, are an alkylene or an alkylene ether;

(B10)

Y is selected from the group consisting of $CH_2$, O, S and NH; and

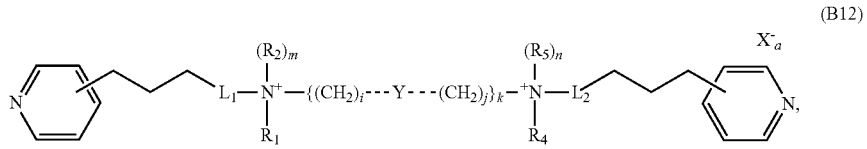

(B12)

wherein
at least one of $R_1$ and $R_4$ is a straight chain or branched, cyclic, alkyl, alkenyl, alkynyl or aryl group having from about 8 to about 24 carbon atoms;

$R_2$ and $R_5$, independently of one another, are selected from the group consisting of H and a $C_1$-$C_8$ alkyl alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

m and n are 0 or 1;
i and j are integers from about 2 to about 3;
k is an integer from 1 to about 3;
$L_1$ and $L_2$, independently from one another, are an alkylene or an alkylene ether;
Y is selected from the group consisting of CHI, O, S and NH; and

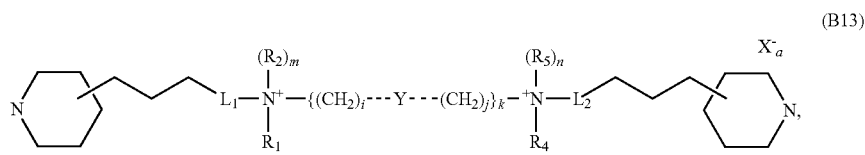

(B13)

wherein
at least one of $R_1$ and $R_5$ is a straight chain or branched, cyclic, alkyl, alkenyl, alkynyl or aryl group having from about 8 to about 24 carbon atoms;

$R_2$ and $R_5$, independently of one another, are selected from the group consisting of H and a $C_1$-$C_8$ alkyl, alkenyl, aryl, and alkyl optionally substituted by one or more of an alcohol, an amine, an amide, an ether, a polyether, a polyamide, an ester, a mercaptan, a urea, a thiourea, a guanidyl, or a carbamoyl group;

m and n are 0 or 1;
i and j are integers from about 2 to about 3;
k is an integer from 1 to about 3;
$L_1$ and $L_2$, independently from one another, are an alkylene or an alkylene ether;
Y is selected from the group consisting of $CH_2$, O, S and NH.

In each of formulae (B1) through (B13) preferably $R_1$ and $R_4$ are each $C_{6-30}$ alkyl or alkenyl, more preferably $C_{8-24}$ alkyl or alkenyl, and $R_2$ and $R_5$ or $R_3$ and $R_6$ are each hydrogen or $C_{1-8}$ alkyl.

Specific compounds within the scope of the invention include the following examples. $R_7$ and $R_8$ in the formulae are independently H or a carbohydrate, preferably H.

23                                    24
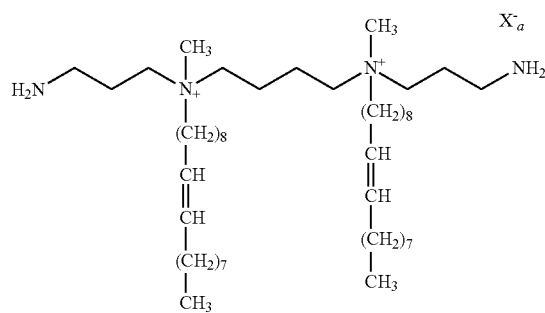
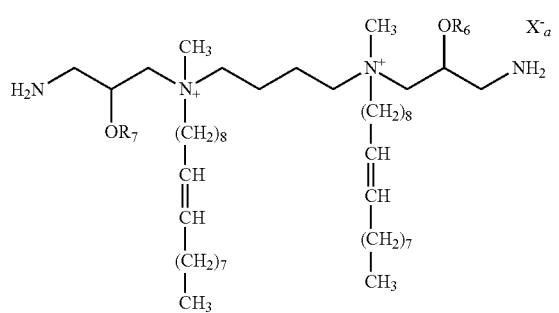
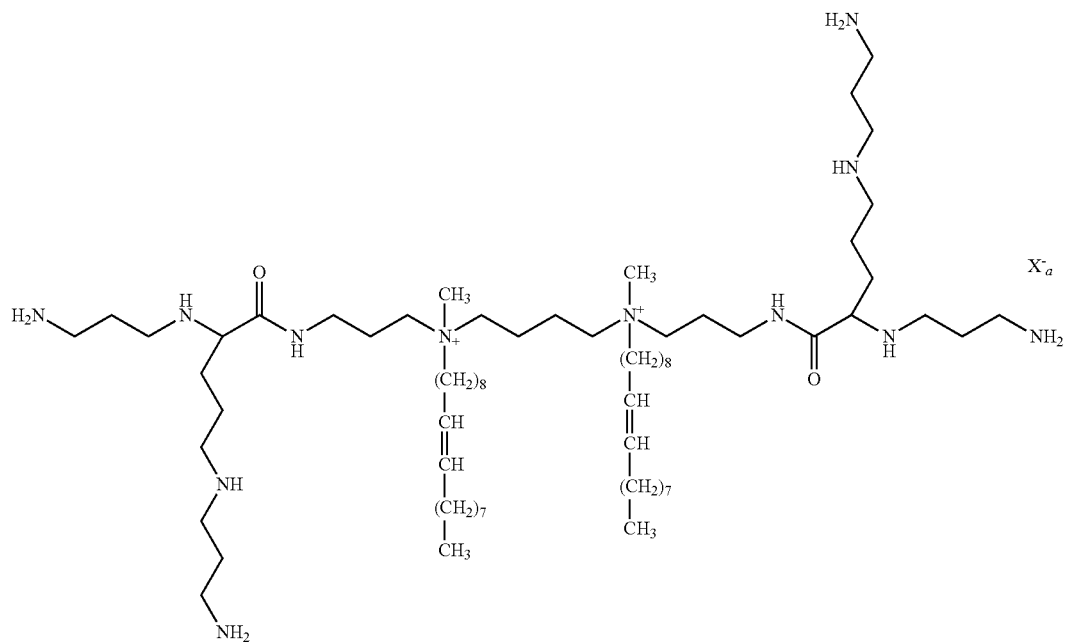
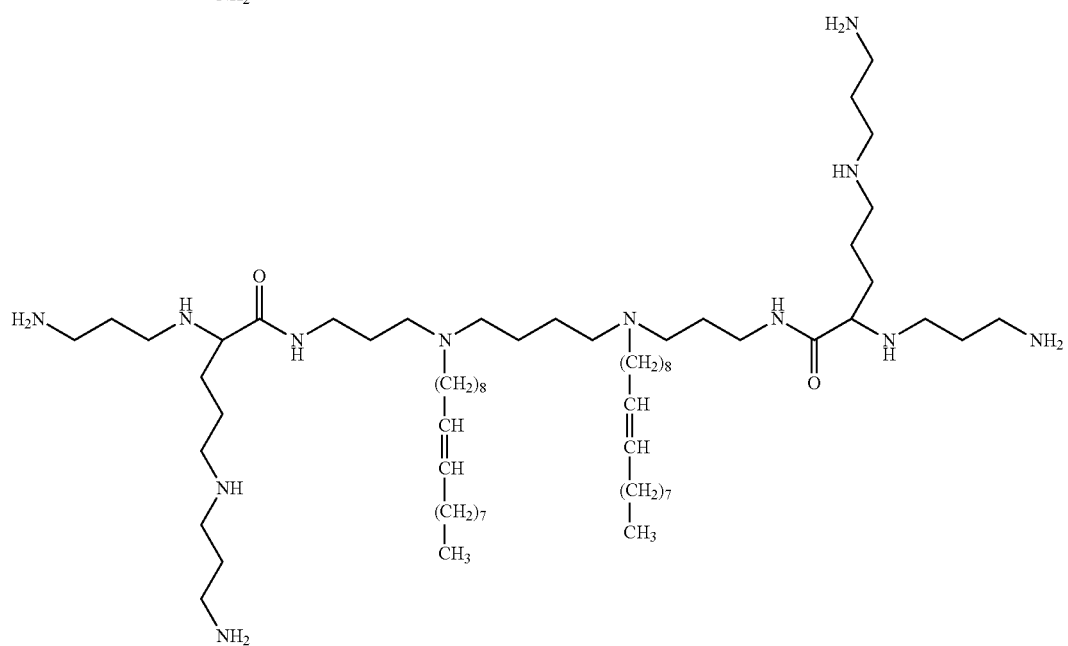

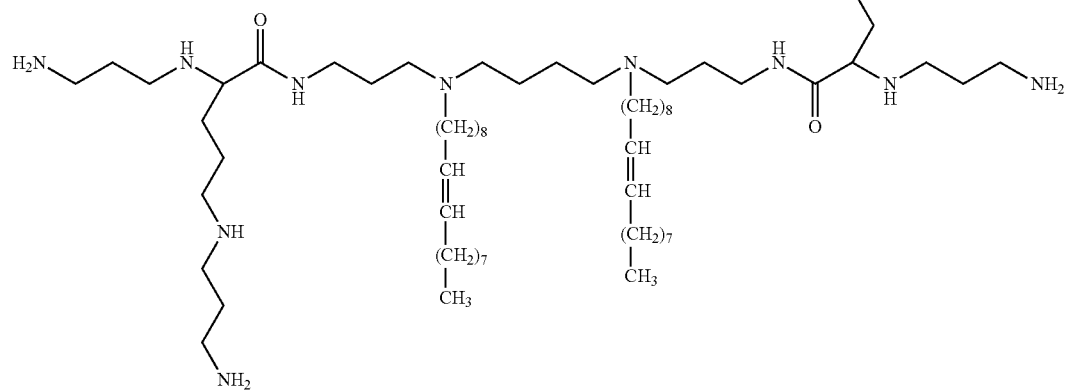
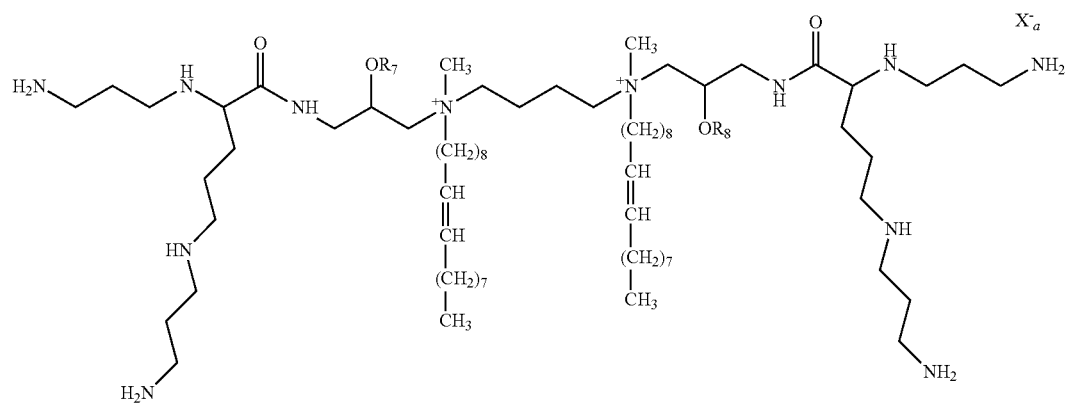
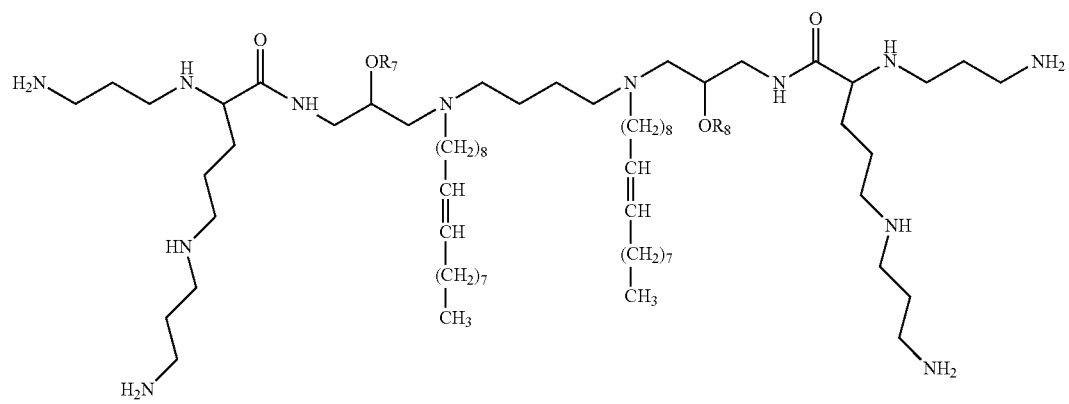

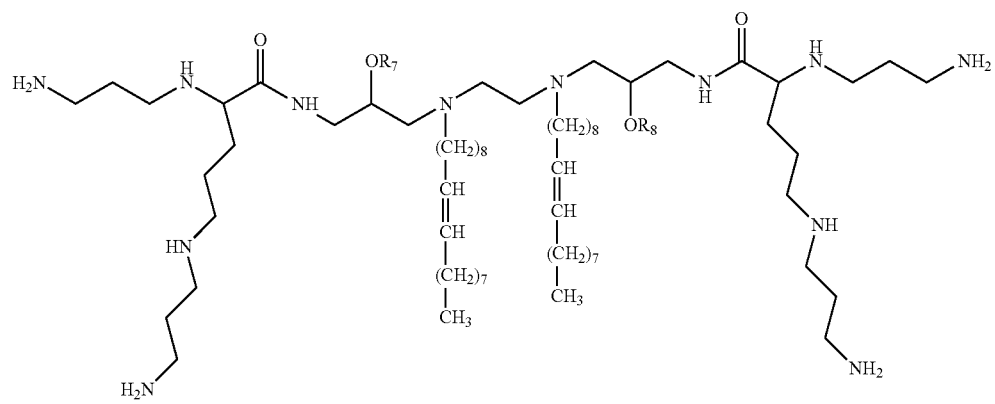
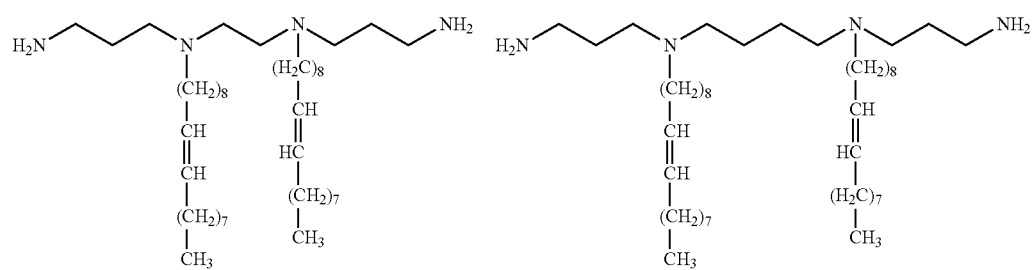
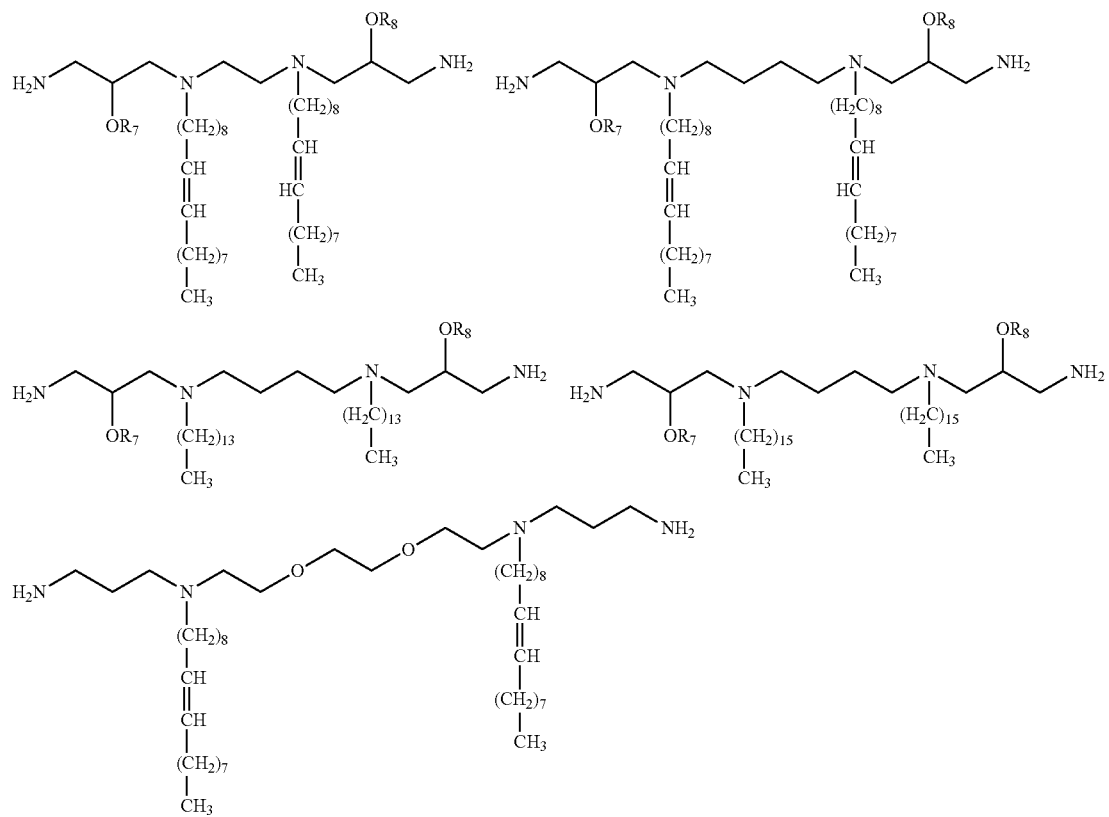

-continued
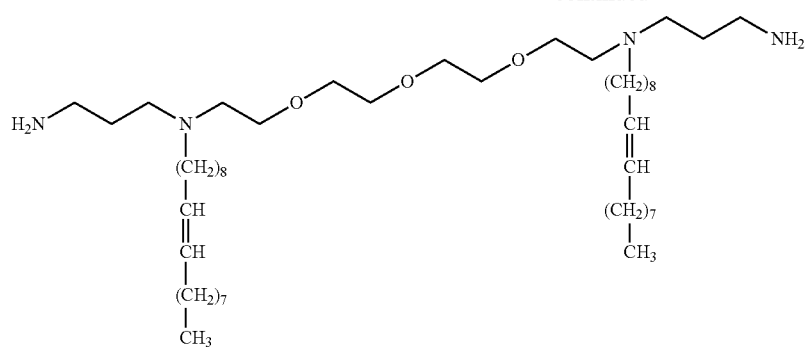
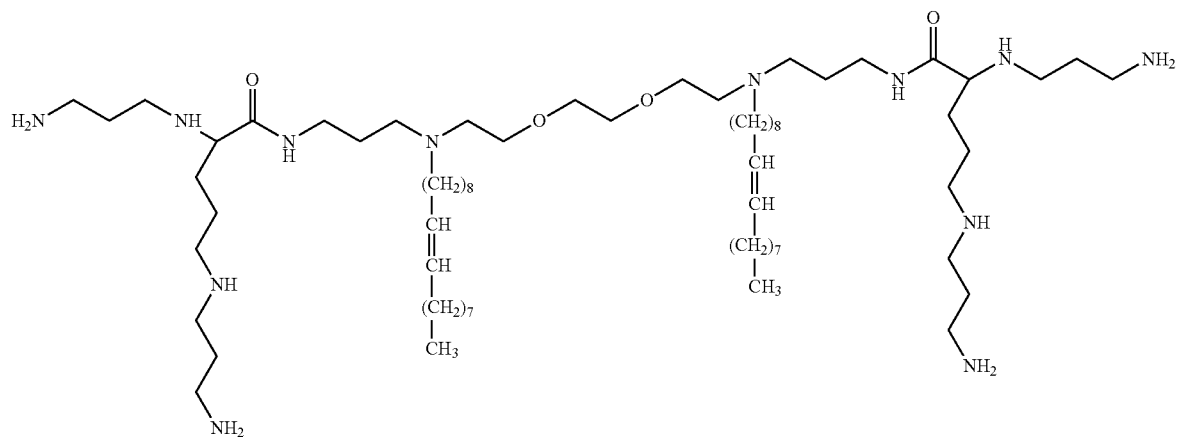
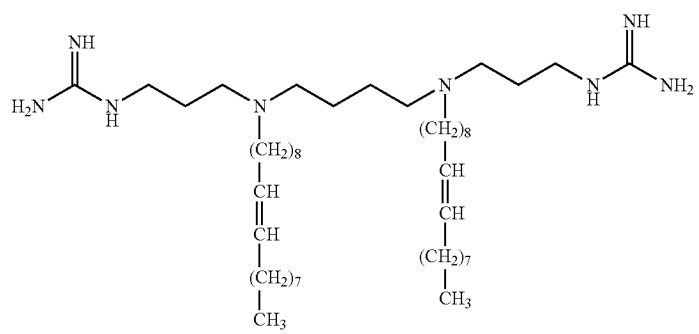
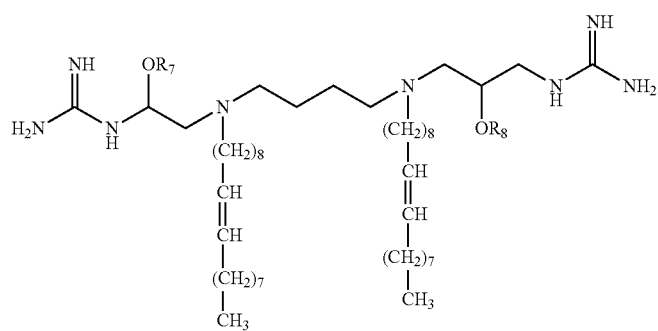

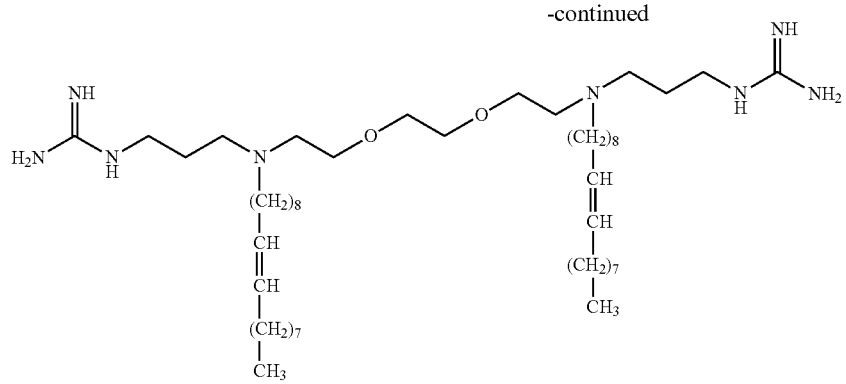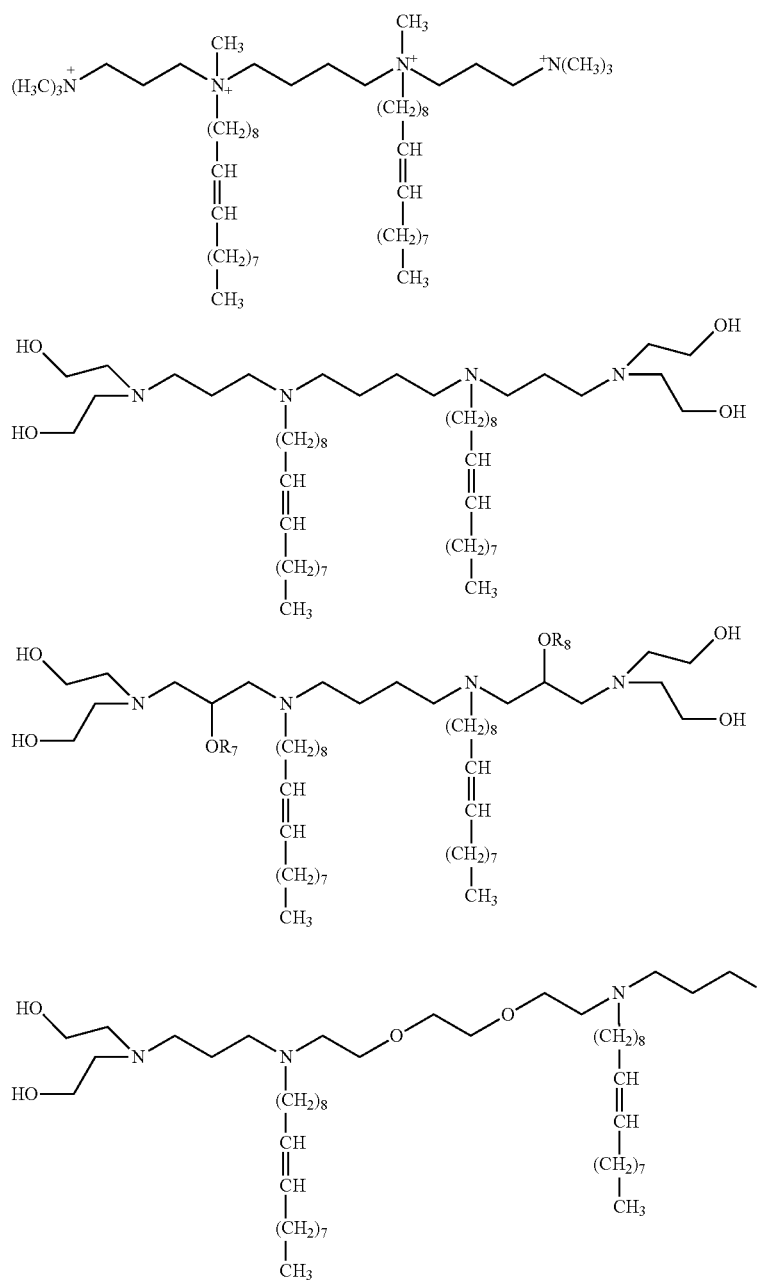

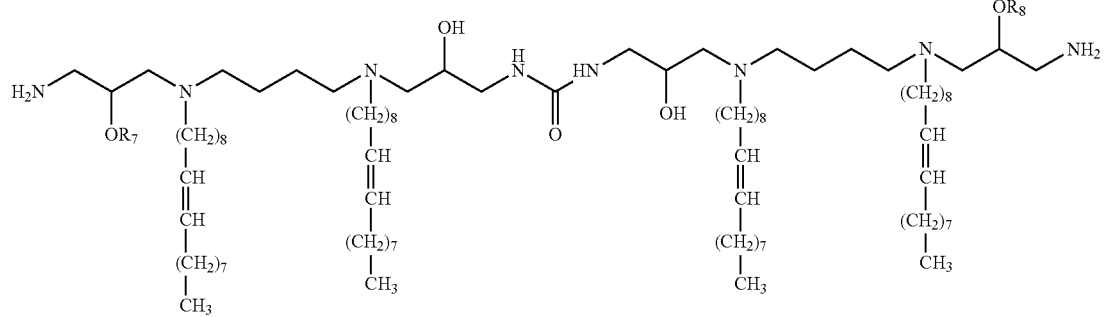
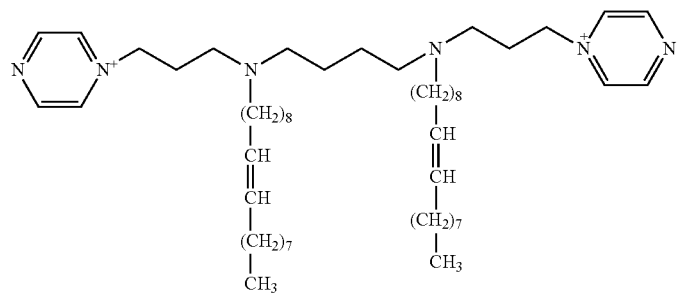
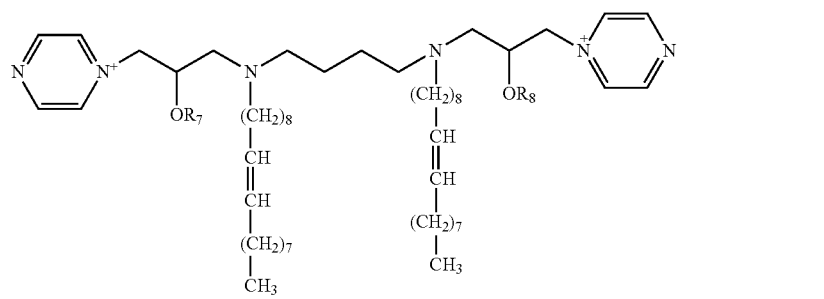
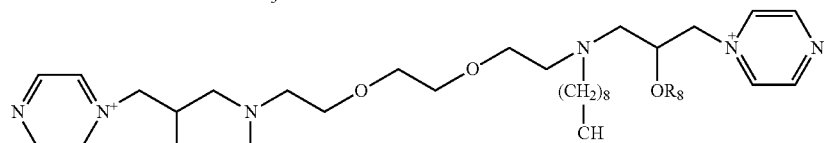
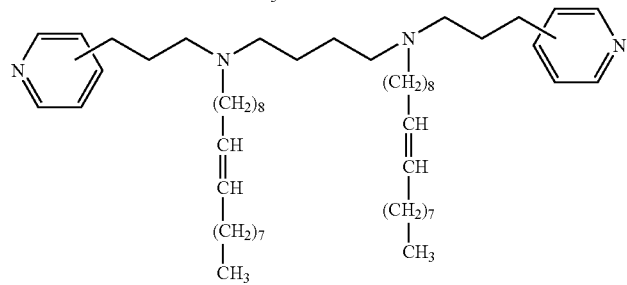

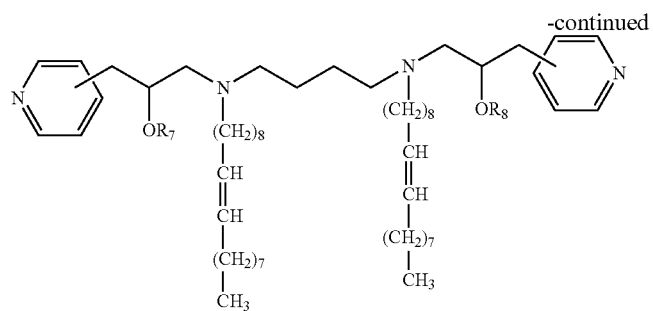
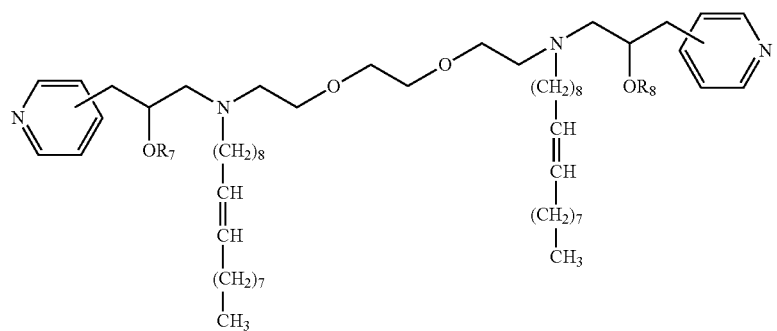
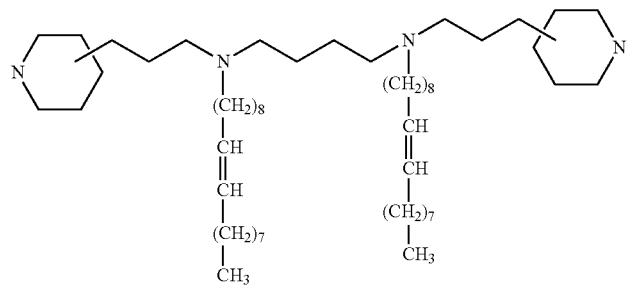
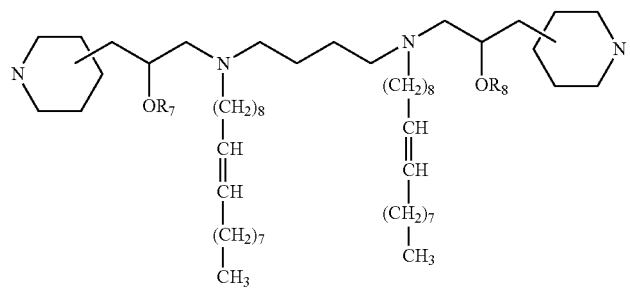
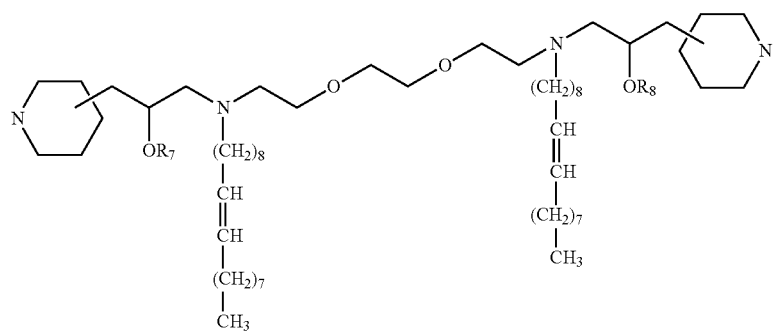

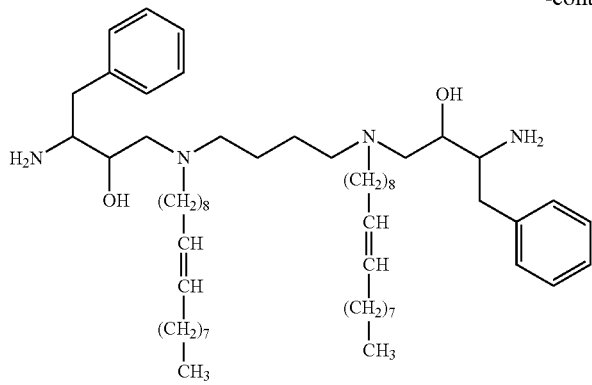

Further, the compounds according to the present invention have the Formula (C):

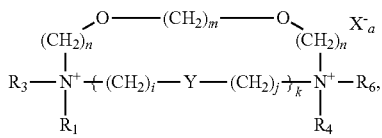

wherein

Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine a carbonyl, and a secondary amino group and wherein Y is optionally substituted by $—X_1$-$L'$-$X_2$—Z or —Z;

$R_1$, $R_3$, $R_4$ and $R_6$, independently of one another, are selected from the group consisting of H, $—(CH_2)_p$-D-Z, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, an alkylthio, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group, and $R_1$, $R_3$, $R_4$ and $R_6$ may optionally be covalently linked with each other or with Y, to form a cyclic moiety;

Z is selected from the group consisting of amine, spermiyl, carboxyspermiyl, guanidyl, spermidinyl, putricinyl, diaminoalkyl, pyridyl, piperidinyl, pyrrolidinyl, polyamine, amino acid, peptide, and protein;

$X_1$ and $X_2$, independently of one another, are selected from the group consisting of NH, O, S, alkylene, and arylene;

$L'$ is selected from the group consisting of alkylene, alkenylene, alkynylene, arylene, alkylene ether, and polyether;

D is Q or a bond;

m and n are 0 or 1; and i, j, k, l and p are integers independently selected from 1 to about 10.

Preferably, Y is selected from the group consisting of $CH_2$, an ether, a polyether, an amide, a polyamide, an ester, a sulfide, a urea, a thiourea, a guanidyl, a carbamoyl, a carbonate, and a secondary amino group.

Preferably, $R_1$, $R_3$, $R_4$ and $R_6$, independently of one another, are selected from the group consisting of H, $—(CH_2)_p$—Z, an alkyl, an alkenyl, an aryl, and an alkyl or an alkyl ether optionally substituted by one or more of an alcohol, an aminoalcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkenyl or aryl group, and $R_1$, $R_3$, $R_4$ and $R_6$ may be covalently linked with each other, to form a cyclic moiety.

Preferably, at least one of $R_1$ and $R_4$ is straight chain or branched, cyclic, alkyl, alkenyl, alkynyl or aryl group having from about 2 to 100, preferably 4 to 75, more preferably 6 to 64, more preferably 8 to 50, more preferably 8 to 40, more preferably 8 to 30, more preferably 6 to 30, more preferably 4 to 30, and most preferably 8 to about 24 carbon atoms.

Preferably, Y is selected from the group consisting of $CH_2$, O, S and NH.

The compounds and polycations of the present invention have the following Formula (D):

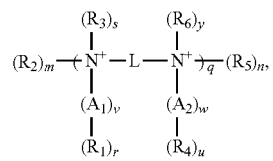

wherein

L is C, CH, $(CH_2)$, or $\{(CH_2)_i—Y—(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, a phosphate, a sulfate, a sulfoxide, an imine, a carbonyl, and a secondary amino group and wherein Y is optionally substituted by $—X_1$-$L'$-$X_2$—Z or —Z.

$R_1$-$R_6$, independently of one another, are selected from the group consisting of H, $—(CH_2)_p$-D-Z, an alkyl, an alkenyl, an aryl, and an alkyl or an alkyl ether optionally substituted by one or more of an alcohol, an amino alcohol, an amine, an amide, an ether, a polyether, a polyamide, an ester, a mercaptan, an alkylthio, a urea, a thiourea, a guanidyl, or a carbamoyl group, and wherein at least one of $R_1$, $R_3$, $R_4$ and $R_6$ is a straight chain or branched, cyclic, alkyl, alkenyl, alkynyl or aryl group;

Z is selected from the group consisting of amine, spermiyl, carboxyspermiyl, guanidyl, spermidinyl, putricinyl, diaminoalkyl, pyridyl piperidinyl, pyrrolidinyl, polyamine, amino acid, amino acid derivative, peptide, and protein;

$X_1$ and $X_2$, independently of one another, are selected from the group consisting of NH, O, S, alkylene and arylene;

L' is selected from the group consisting of alkylene, alkenylene, alkynylene, arylene, alkylene ether, and polyether;

$A_1$ and $A_2$, independently of one another, are selected from the group consisting of $CH_2O$, $CH_2S$, $CH_2NH$, $C(O)$, $C(NH)$, $C(S)$ and $(CH_2)_t$;

m, n, r, s, u, v, w and y are 0 or 1, with the proviso that when both m and n are 0 at least one of r, s, u and y is other than 0;

i, j, k, l, p and t are integers from 0 to about 100; and q is an integer from 1 to about 1000.

Also, the present invention provides compounds or polycations according to the Formula (E):

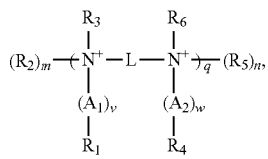

wherein

L is $(CH_2)_t$ or $\{(CH_2)_i—Y—(CH_2)_j\}_k$, wherein Y is selected from the group consisting of $CH_2$, an ether, a polyether, an amide, a polyamide, an ester, a sulfide, a urea, a thiourea, a guanidyl, a carbamoyl, a carbonate, and a secondary amino group;

$R_1$-$R_6$, independently of one another, are selected from the group consisting of H, $—(CH_2)_p—Z$, an alkyl, an alkenyl, an aryl, and an alkyl or an alkyl ether optionally substituted by one or more of an alcohol, an amino alcohol, an amine, an amide, an ether, a polyether, a polyamide, an ester, a mercaptan, a urea, a thiourea, a guanidyl, or a carbamoyl group, and at least one of $R_1$, $R_3$, $R_4$ and $R_6$ is a straight chain or branched, cyclic, alkyl, alkenyl, alkynyl or aryl group; $Z$, $A_1$, $A_2$, m, n, i, j, k, l, p, t and q are as defined above.

In the above formulae (D) and (E), $R_1$-$R_6$, Y, i, j, k, l, p, t and q are preferably as defined with reference to Formula (A).

It would be obvious for a skilled person that when Q is O or S, the number of substituents should be according their valency.

Certain of the compounds of the invention may be insufficiently soluble in physiological media to employ for delivery and transfection methods. Those of ordinary skill in the art will appreciate that there are a variety of techniques available in the art to enhance solubility of such compounds in aqueous media. Such methods are readily applicable without undue experimentation to the compounds described herein.

DEFINITIONS

Useful aryl groups are $C_{6-100}$ aryl, preferably $C_{6-75}$ aryl, more preferably $C_{6-64}$ aryl, more preferably $C_{6-50}$ aryl, more preferably $C_{6-40}$ aryl, more preferably $C_{6-30}$ aryl, most preferably $C_{5-24}$ aryl. Typical $C_{6-100}$ aryl groups include phenyl, naphthyl, phenanthryl, anthracyl, indenyl, azulenyl, biphenyl, biphenylenyl, fluorenyl, pyrenyl, aceanthrenyl, cholantrenyl, acephenanthrenyl, violantherenyl, hexaphenyl, hexacenyl, trinaphtyl and pyranthyl groups.

Useful alkyl groups are straight chain or branched $C_{2-100}$ alkyl groups, preferably $C_{4-75}$ alkyl, more preferably $C_{6-64}$ alkyl, more preferably $C_{8-50}$ alkyl, more preferably $C_{8-40}$ alkyl, more preferably $C_{8-30}$ alkyl, more preferably $C_{6-30}$ alkyl, more preferably $C_{4-30}$ alkyl, most preferably $C_{8-24}$ alkyl. Typical $C_{2-100}$ alkyl groups include ethyl, propyl, isopropyl, butyl, sec.-butyl, tert.-butyl, pentyl, hexyl, octyl, decyl, dodecyl, tetradecyl, hexadecyl, octadecyl, eicosyl, docosyl, tetracosyl, hexacosyl, octacosyl and triacontyl groups. Also contemplated is a trimethylene group substituted on two adjoining positions on any benzene ring of the compounds of the invention.

Useful alkenyl groups are straight chain or branched $C_{2-100}$ alkenyl, preferably $C_{4-75}$ alkenyl, more preferably $C_{6-64}$ alkenyl, more preferably $C_{8-50}$ alkenyl, more preferably $C_{8-40}$ alkenyl, more preferably $C_{8-30}$ alkenyl, more preferably $C_{6-30}$ alkenyl, more preferably $C_{4-30}$ alkenyl, most preferably $C_{8-24}$ alkenyl. Typical $C_{2-100}$ alkenyl groups include ethenyl, propenyl, isopropenyl, butenyl, sec.-butenyl, hexenyl, octenyl, decenyl, dodecenyl, especially 9-dodecenyl, tetradecenyl, especially 9-tetradecenyl, hexadecenyl, especially 9-hexadecenyl, octadecenyl, especially 9-octadecenyl, eicosenyl, docosenyl, tetracosenyl, hexacosenyl, octacosenyl and triacontenyl.

Useful alkynyl groups are straight chain or branched $C_{2-100}$ alkynyl, preferably $C_{4-75}$ alkynyl, more preferably $C_{6-64}$ alkynyl, more preferably $C_{8-50}$ alkynyl, more preferably $C_{8-4}$ alkynyl, more preferably $C_{8-30}$ alkynyl, more preferably $C_{6-30}$ alkynyl, more preferably $C_{4-30}$ alkynyl, most preferably $C_{8-24}$ alkynyl. Typical $C_{2-100}$ alkynyl groups include ethynyl, propynyl, butynyl, -butynyl, hexynyl, octynyl, decynyl, dodecynyl, tetradecynyl, hexadecynyl, octadecynyl, eicosynyl, docosynyl, tetracosynyl, hexacosynyl, octacosynyl and triacontynyl groups.

Typical alkyl ether groups include any of the above-mentioned $C_{2-100}$ alkyl groups having an ether group.

An ether group is —O—.

Typical polyether groups include the $—(CHR^{14}—CH_2—O)_t—$, wherein $R^{14}$ is H or a $C_{1-4}$ alkyl group and t is an integer as defined above, preferably t is 2 to 5.

For the purposes of the invention an amide group is an organic radical having —NHC(O)— as a functional group. Typical amide groups include alkyl amides, alkenyl amides, alkynyl amides, and aryl amides, wherein alkyl, alkenyl, alkynyl and aryl are as defined above.

Typically polyamide groups include organic radicals having two or more amide groups as defined above.

Typically an ester group is an organic radical having —C(O)—O— as a functional group. Typical ester groups include $R^{14}$—C(O)—O—$R^{15}$, wherein $R^{14}$ and $R^{15}$ are alkylene, alkenylene, alkynylene and arylene groups as defined above.

Typically urea groups are organic radicals having —NH—C(O)—NH— as a functional group. Typical urea groups include $R^{14}NH—C(O)—NHR^{14}$, $R^{14}NH—C(O)—NHR^{15}$, $R^{14}R^{15}N—C(O)—NR^{14}R^{15}$ wherein $R^{14}$ and $R^{15}$ are alkylene, alkenylene, alkynylene and arylene groups as defined above.

Typically thiourea groups are organic radicals having urea group as defined above wherein the oxygen in the urea group is substituted by sulfur.

Typically guanidyl groups are organic radicals having —NH—C(NH)—NH— as a functional group. Typical guanidyl groups include $R^{14}NH—C(NH)—NHR^{14}$, $R^{14}NH—C(NH)—NHR^{15}$ and $R^{14}R^{15}N—C(NH)—NR^{14}R^{15}$ wherein $R^{14}$ and $R^{15}$ are alkylene, alkenylene, alkynylene and arylene groups as defined above.

A carbamoyl group is —NH—C(O)—O—.

Typically carbonate groups include organic radicals containing a $CO_3^{2-}$ radical, i.e., —O—C(O)—O.

A phosphate group is a $PO_4^{3-}$ radical.

A sulfate group is a $SO_4^{2-}$ radical.

A sulfoxide group is —S(O)—.

An imine group is —C(N)—.

A carbonyl group is —C(O)—.

A secondary amino group is —NH—.

Typically amino alcohol groups are organic radicals having both a secondary amino group as defined above and a hydroxyl group. Typical aminoalcohols include amino ethanol, aminopropanol and aminobutanol.

The definition "D is a bond" means that when D is not Q there is a single bond between $(CH_2)_p$ and Z.

Biologically Active Substance refers to any molecule or mixture or complex of molecules that exerts a biological effect in vitro and/or in vivo, including pharmaceuticals, drugs, proteins, peptides, polypeptides, hormones, vitamins, steroids, polyanions, nucleosides, nucleotides, nucleic acids (e.g. DNA or RNA), nucleotides, polynucleotides, etc.

Cationic Lipids refers to any cationic lipids which may be used for transfection, including but not limited to, DOSPA, DOTMA, DMRIE, DOTAP, DOGS and TM-TPS.

Cell refers to eukaryotic cells of any type and from any source. Types of eukaryotic cells include epithelial, fibroblastic, neuronal, hematopoietic cells and the like from primary cells, tumor cells or immortalized cell lines. Sources of such cells include any animal such as human, canine, mouse, hamster, cat, bovine, porcine, monkey, ape, sheep, fish, insect, fungus and any plant including crop plants, ornamentals and trees.

Delivery is used to denote a process by which a desired compound is transferred to a target cell such that the desired compound is ultimately located inside the target cell or in, or on, the target cell membrane. In many uses of the compounds of the invention, the desired compound is not readily taken up by the target cell and delivery via lipid aggregates is a means for getting the desired compound into the cell. In certain uses, especially under in vivo conditions, delivery to a specific target cell type is preferable and can be facilitated by compounds of the invention.

Drug refers to any therapeutic or prophylactic agent other than food which is used in the prevention, diagnosis, alleviation, treatment, or cure of disease in man or animal.

Kit refers to transfection or protein expression kits which include one or more of the compounds of the present invention or mixtures thereof. Such kits may comprise a carrying means being compartmentalized to receive in close confinement one or more container means such as vials, test tubes and the like. Each of such container means comprises components or a mixture of components needed to perform transfection. Such kits may include one or more components selected from nucleic acids (preferably one or more vectors), cells, one or more compounds of the present invention, lipid-aggregate forming compounds, transfection enhancers, biologically active substances, etc.

Lipid Aggregate is a generic term which includes liposomes of all types both unilamellar and multilameller as well as micelles and more amorphous aggregates of cationic lipids or lipids mixed with amphiphatic lipids such as phospholipids and steroids.

Lipid Aggregate-forming Compounds refers to neutral compounds or lipids such as DOPE, DOPC and cholesterol, etc.

Target Cell refers to any cell to which a desired compound is delivered, using a lipid aggregate as carrier for the desired compound.

Transfection is used herein to mean the delivery of nucleic acid, protein or other macromolecule to a target cell, such that the nucleic acid, protein or other macromolecule is expressed or has a biological function in the cell. The term "expressible nucleic acid" includes both DNA and RNA without regard to molecular weight, and the term "expression" means any manifestation of the functional presence of the nucleic acid within the cell including, without limitation, both transient expression and stable expression. Functional aspects include inhibition of expression by oligonucleotides or protein delivery.

Transfection Enhancers refers generally to molecules and substances such as proteins, peptides, growth factors and the like that enhance cell-targeting, uptake, internalization, nuclear targeting and expression. Such molecules and substances include ligands such as insulin, transferrin, fibronectin that target the cell surface; peptides that target cellular integrin receptors; and other compounds such as Plus Reagent (available from Life Technologies, Inc., Rockville, Md.). Examples of transfection enhancers may be found in U.S. Pat. No. 5,736,392 and U.S. application Ser. No. 09/039,780 filed Mar. 16, 1998.

The invention will be further clarified by the following examples, which are intended to be purely exemplary of the invention. The polycationic lipids were prepared by following the general reaction schemes described below.

EXAMPLES

Example 1

Synthesis of $N_1,N^4$-dioleoyl-diaminobutane (I)

A solution of 1,4-diaminobutane (4.28 g, 48.6 mmol) and triethylamine (20.4 ml, 146 mmol) in 10 mL of dry methylene chloride was slowly added to a solution of oleoyl chloride (30.0 g, 99.7 mmol) in 300 ml of anhydrous methylene chloride in an ice bath 25 at 0° C. The reaction mixture was stirred vigorously with a mechanical stirrer. After the addition was complete, the ice bath was removed and the mixture was stirred at room temperature for 2.5 days. TLC analysis confirmed that the reaction had gone to completion and the product had precipitated. The excess oleoyl chloride was removed by filtration. The precipitate was washed twice with 50 ml of methylene chloride. The mother liquor was concentrated and more product precipitated. This precipitate was filtered and combined with the previous precipitate. The resulting solid was vacuum dried for 4 hours. A total of 27.0 g of a white solid of the desired product, $N^1,N^4$-dioleoyl-diaminobutane, was obtained.

Synthesis of N1,N-dioleyl-diaminobutane (II)

Lithium aluminum hydride (8.62 g, 95%, 216 mmol) was carefully added to a suspension of $N^1,N^4$-dioleoyl-diaminobutane (27.0 g, 43.8 mmol) in 400 ml of anhydrous diethyl ether at 0° C. After addition, the ice bath was removed. The reaction mixture was warmed slowly to room temperature and then heated gently to reflux with an appropriate condensing device and stirred for 16 hours. The reaction mixture was then cooled and quenched carefully at 0° C. with 70 mL of a 1 N sodium hydroxide solution. Another 500 mL of diethyl ether was added and the mixture was stirred at room temperature for additional 2 hours. The top ether layer turned clear gradually and then separated. The aqueous layer was extracted three times with 100 mL of diethyl ether each. The combined ether solution was concentrated, and dried on high vacuum overnight. Total of 17.0 g of oily colorless $N^1,N^4$-dioleyl-diaminobutane was obtained.

Synthesis of $N^1,N^4$-dioleyl-$N^1,N^4$-di-[2-hydroxy-3-(N-phthalamido)propyldiamino-butane (III)

Diisopropylethylamine (11.1 mL, 63.7 mmol) was added to a suspension of $N^1,N^4$-dioleyl-diaminobutane (15.5 g, 26.3 mmol) and N-(2,3-epoxypropyl)-phthalimide (15.6 g, 76.8 mmol) in 110 mL of dry N,N-dimethylformamide. After purging with nitrogen, the reaction mixture was sealed in a round-bottom flask and heated to around 90° C. for 24 hours. N,N-dimethylformamide and diisopropylethylamine were removed and a yellow oil was obtained. This crude material was recrystallized from ethanol. A total of 18.6 g of a white solid, $N^1,N^4$-dioleyl-$N^1,N^4$-di-[2-hydroxy-3-(N-phthalamido)propyl]-diamino-butane was obtained.

Synthesis of $N^1,N^4$-dioleyl-$N^1,N^4$-di-[2-hydroxy-3-(N-aminopropyl)]-diaminobutane (IV) (hereinafter referred to as DHDOS)

Hydrazine (4.0 mL, 80% aq., 103 mmol) was added to a suspension of $N^1,N^4$-dioleyl-$N^1$, $N^4$-di-[2-hydroxy-3-(N-phthalamido)propyl]-diaminobutane (17.0 g, 17.1 mmol) in 250 mL of dry ethanol at room temperature. With an appropriate condensing device, the reaction mixture was heated to a reflux, at which point the suspension turned into a clear solution. The oil bath was set to 85° C. After 45 minutes a white solid precipitated from the solution. The reaction mixture was stirred at reflux for 4 hours before being cooled to −20° C. The white solid settled down to the bottom. The top clear ethanol solution was decanted. The residue was washed twice with cold ethanol. The combined ethanol solution was concentrated and dried overnight over vacuum. 12.4 g of oily $N^1,N^4$-dioleyl-$N^1,N^4$-di-[2-hydroxy-3-(N-aminopropyl)]-diaminobutane was obtained.

The following compounds were synthesized by the above method using the corresponding diamine and a long chain acyl chloride:

$N^1,N^4$-dimyristyl-$N^1,N^4$-di-[2-hydroxy-3-(N-aminopropyl-)]-diaminobutane;
$N^1,N^4$-dipalmityl-$N^1,N^4$-di-[2-hydroxy-3-(N-aminopropyl-)]-diaminobutane;
$N^1,N^4$-dipalmitolyl-N  $N^1,N^4$-di-[2-hydroxy-3-(N-aminoprop-yl)]-diaminobutane;
$N^1,N^4$-distearyl-$N^1,N^4$-di-[2-hydroxy-3-(N-aminopropyl)-]-diaminobutane;
$N^1,N^4$-dilauryl-$N^1,N^4$-di-[2-hydroxy-3-(N-aminopropyl)]-diaminobutane;
$N^1,N^2$-dimyristyl-$N^1,N^2$-di-[2-hydroxy-3-(N-aminopropyl-)]-diaminoethane;
$N^1,N^2$-dipalmity-$N^1,N^2$-di-[2-hydroxy-3-(N-aminopropyl)-]-diaminoethane;
$N^1,N^2$-dipalmitolyl-$N^1,N^2$-di-[2-hydroxy-3-(N-aminopropyl)]-diaminoethane;
$N^1,N^2$-distearyl-$N^1,N^2$-di-[2-hydroxy-3-(N-aminopropyl)-]-diaminoethane;
$N^1,N^2$-dilauryl-$N^1,N^2$-di-[2-hydroxy-3-(N-aminopropyl)]-diaminoethane;
$N^1,N^2$dioleyl-$N^1,N^2$-di-[2-hydroxy-3-(N-aminopropyl)]-diaminoethane;
$N^1,N^8$-dimyristyl-$N^1,N^8$-di-[2-hydroxy-3-(N-aminopropyl-)]-Jeffamine;
$N^1,N^8$-dipalmityl-$N^1,N^8$-di-[2-hydroxy-3-(N-aminopropyl-)]-Jeffamine;
$N^1,N^8$-dipalmitolyl-$N^1,N^8$-di-[2-hydroxy-3-(N-aminopropyl)]-Jeffamine;
$N^1,N^8$-distearyl-$N^1,N^8$-di-[2-hydroxy-3-(N-aminopropyl)-]-Jeffamine;
$N^1,N^8$-dilauryl-$N^1,N^8$-di-[2-hydroxy-3-(N-aminopropyl)]-Jeffamine;
$N^1,N^8$-dioleyl-$N^1,N^8$-di-[2-hydroxy-3-(N-aminopropyl)]-Jeffamine;

Synthesis of $N^1,N^4$-dioleyl-$N^1,N^4$-di-[2-hydroxy-3-(N-carboxamidine)-aminopropyl]-diaminobutane (V)

1H-pyrazole-1-carboxamidine hydrochloride (45 mg, 0.31 mmol) was added to a solution of $N^1,N^4$-dioleyl-$N^1,N^4$-di-[2-hydroxy-3-(N-aminopropyl)]-diamino-butane (115 mg, 0.156 mmol) in 1 mL of dry N,N-dimethylformamide. The salt was not very soluble in dimethylformamide (DMF). However, the mixture turned clear after diisopropylethylamine (55 µl, 0.31 mmol) was added. The mixture was stirred under nitrogen at room temperature for 18 hours. After removal of solvent, the crude material was loaded on a C-18 reverse phase flash column, and eluted with 20% $H_2O$ in MeOH to 10% $H_2O$ in MeOH. The pure fractions were collected and concentrated. An 81 mg colorless oily $N^1,N^4$-dioleyl-$N^1,N^4$-di-[2-hydroxy-3-(N-carboxamidine)-aminopropyl]-diaminobutane was obtained, which was converted to its TFA and HCL salts.

Synthesis of $N^1,N^4$-dioleyl-$N^1,N^4$-di-{2-hydroxy-3-[N($N^I,N^{II},N^{III},N^{IV}$-butoxycarbonyl-spermine carboxamido)]aminopropyl}diaminobutane (VI)

Diisopropylcarbodiimide (5.32 mL, 34.0 mmol) was added drop wise to a solution of Boc-spermine acid (21.7 g, 33.5 mmol) and N-hydroxysuccinimide (NHS) (3.91 g, 34.0 mmol) in mixed solvents (100 mL of DMF and 100 mL of $CH_2Cl_2$) at room temperature. After stirring for 2.5 hours, a solution of $N^1,N^4$-dioleyl-$N^1,N^4$-di-[2-hydroxy-3-(N-aminopropyl)]diaminobutane (10 g, 13.6 mmol) in 40 mL of methylene chloride and DMF was added. The mixture was stirred for another 5 hours before quenching with 200 mL of a 2.5% sodium bicarbonate solution. An additional 300 mL of methylene chloride was added. The aqueous solution was extracted with 120 mL of methylene chloride three times. The combined organic solution was washed with water twice and dried over anhydrous magnesium sulfate. After concentration, a pale yellow oil was obtained. The crude material was purified with silica gel, eluting with 2% MeOH in $CH_2Cl_2$ to 5% MeOH in $CH_2Cl_2$. A total of 13.1 g of white solid $N^1,N^4$-dioleyl-$N^1,N^4$-di-{2-hydroxy-3-[N—($N^I$,N.sup.$^{II}$,$N^{III}$,$N^{IV}$-butoxycarbonyl-spermine carboxamido)]aminopropyl}diaminobutane was obtained.

Synthesis of $N^1,N^4$-dioleyl-$N^1,N^4$-di-[2-hydroxy-3-(N-spermine carboxamido)-aminopropyl]-diaminobutane (VII)

100 mL of a solution of 4.0 M hydrogen chloride in 1,4-dioxane was added to a solution of $N^1,N^4$-dioleyl-$N^1,N^4$-di-{2-hydroxy-3-[N—($N^I,N^{II},N^{III},N^{IV}$ butoxycarbonylspermine carboxamido]aminopropyl}diaminobutane (11.8 g, 5.92 mmol) in 100 mL of 1,4-dioxane at room temperature. The reaction mixture turned cloudy 10 minutes after addition of the acid. After 2.5 hours of stirring at room temperature, the excess acid and solvent was removed. The residue was dried for at least 5 hours over vacuum before being loaded on a C-18 reverse phase flash column. The column was eluted starting with 25% $H_2O$ in MeOH, then 20%, and then 17%. Pure fractions were collected and concentrated. A 3.06 g colorless solid $N^1,N^4$-dioleyl-$N^1,N^4$-di-[2-hydroxy-3-(N-spenninecarbox-amido)-aminopropyl]-diaminobutane was obtained.

The following compounds were synthesized using the protocol described above starting with the requisite diamine and long chain acyl chloride:

$N^1,N^4$-dimyristyl-$N^1,N^4$-di-[2-hydroxy-3-(N-sperminecarboxamido)-aminopropyl]-diaminobutane;

$N^1,N^4$-dipalmityl-$N^1,N^4$-di-[2-hydroxy-3-(N-sperminecarboxamido)-aminopropyl]-diaminobutane;

$N^1,N^4$-dipalmitolyl-$N^1,N^4$-di-[2-hydroxy-3-(N-sperminecarboxamido)-aminopropyl]-diaminobutane;

$N^1,N^4$-distearyl-$N^1,N^4$-di-[2-hydroxy-3-(N-sperminecarboxamido)-aminopropyl]-diaminobutane;

$N^1,N^4$-dilauryl-$N^1,N^4$-di-[2-hydroxy-3-(N-sperminecarboxamido)-aminopropyl]-diaminobutane;

$N^1,N^8$-dimyristyl-$N^1,N^8$-di-[2-hydroxy-3-(N-sperminecarboxamido)-aminopropyl]-Jeffamine;

$N^1,N^8$-dipalmityl-$N^1,N^8$-di-[2-hydroxy-3-(N-sperminecarboxamido)-aminopropyl]-Jeffamine;

$N^1,N^8$-dipalmitolyl-$N^1,N^8$-di-[2-hydroxy-3-(N-sperminecarboxamido)-aminopropyl]-Jeffamine;

$N^1,N^8$-distearyl-$N^1,N^8$-di-[2-hydroxy-3-(N-sperminecarboxamido)-aminopropyl]-Jeffamine;

$N^1,N^8$-dilauryl-$N^1,N^8$-di-[2-hydroxy-3-(N-sperminecarboxamido)-aminopropyl]-Jeffamine;

$N^1,N^8$-dioleyl-$N^1,N^8$-di-[2-hydroxy-3-(N-sperminecarboxamido)-aminopropyl]-Jeffamine;

$N^1,N^2$-dimyristyl-$N^1,N^2$-di-[2-hydroxy-3-(N-sperminecarboxamido)-aminopropyl]-diaminoethane;

$N^1,N^2$-dipalmityl-$N^1,N^2$-di-[2-hydroxy-3-(N-sperminecarboxamido)-aminopropyl]-diaminoethane;

$N^1,N^2$-dipalmitolyl-$N^1,N^2$-di-[2-hydroxy-3-(N-sperminecarboxamido)-aminopropyl]-diaminoethane;

$N^1,N^2$-distearyl-$N^1,N^2$-di-[2-hydroxy-3-(N-sperminecarboxamido)-aminopropyl]-diaminoethane;

$N^1,N^2$-dilauryl-$N^1,N^2$-di-[2-hydroxy-3-(N-sperminecarboxamido)-aminopropyl]-diaminoethane;

$N^1,N^2$-dioleyl-$N^1,N^2$-di-[2-hydroxy-3-(N-sperminecarboxamido)-aminopropyl]-diaminoethane;

Synthesis of dihydroxy-dioleyol-disperminecarboxamido spermine and analogs (Scheme I)

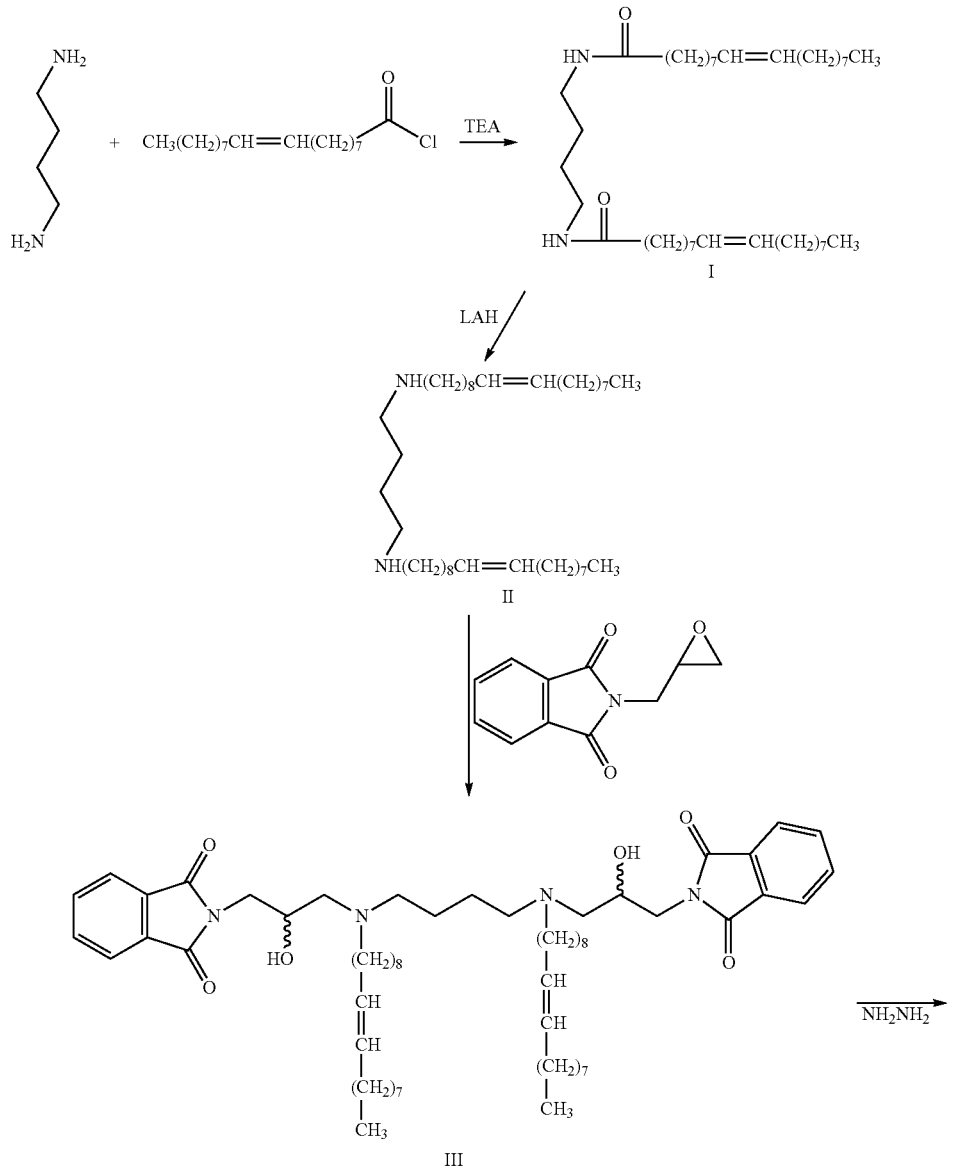

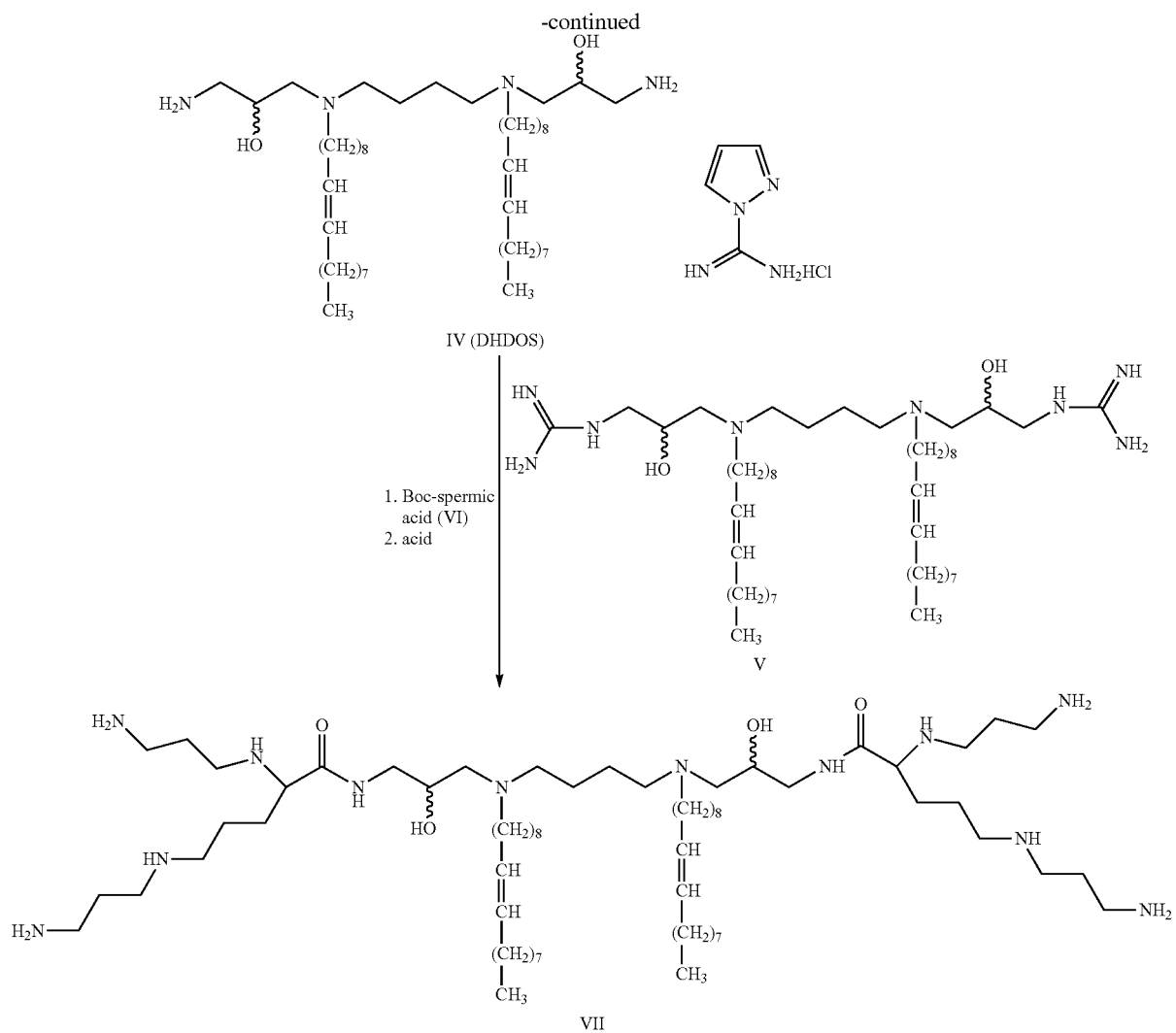

Example 2

Synthesis of $N^1,N^4$-dioleyl-$N^1,N^4$-di-3-cyanopropyl-diaminobutane (VIII)

Acrylonitrile (0.43 mL, 6.53 mmol) was added dropwise to a solution of $N^1,N^4$-dioleyl-diaminobutane (1.8 g, 3.06 mmol) in 20 mL of ethanol at room temperature. The mixture was stirred for 30 hours. All starting materials were converted to product as confirmed by TLC analysis. The crude material was purified using flash chromatography with a silica gel (1% MeOH in $CH_2Cl^2$. A clear oil was obtained at high yield.

Synthesis of $N^1,N_4$-dioleyl-$N^1,N^4$-di-3-(aminopropyl)-diaminobutane (XI)

A solution of LAH (9.2 mL, 1 M in ether, 9.2 mmol) was slowly added to a solution of $N^1,N^4$-dioleyl-$N^1,N^4$-di-3-cyanopropyl-diaminobutane (2.12 g, 3.05 mmol) in 15 mL of anhydrous diethyl ether at 0° C. After addition, the mixture was stirred at room temperature for 20 hours. All starting material was consumed. The reaction mixture was quenched with a 1 N NaOH solution at 0° C. After stirring 2 hours at room temperature, the mixture was extracted with diethyl ether three times. The combined ether solutions were concentrated and dried over vacuum for three hours. An oily $N^1,N^4$-dioleyl-$N^1,N^4$-di-3-(aminopropyl)diaminobutane was obtained at high yield.

Synthesis of $N^1,N^4$-dioleyl-$N^1,N^4$-di-[3-(N-spermine carboxamido)-aminopropyl]-diaminobutane (XI)

The procedure for making $N^1,N^4$-dioleyl-$N^1,N^4$-di-[2-hydroxy-3-(N-spermine carboxamido)-aminopropyl]-diaminobutane described above was followed.

Synthesis of dioleyol-disperminecarboxamido spermine and analogs (Scheme 2)
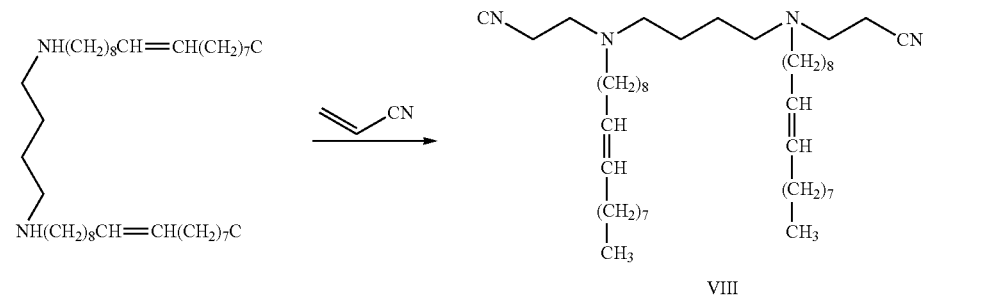
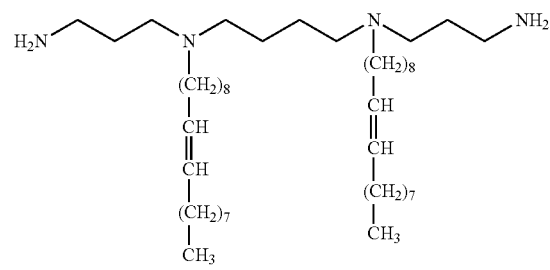
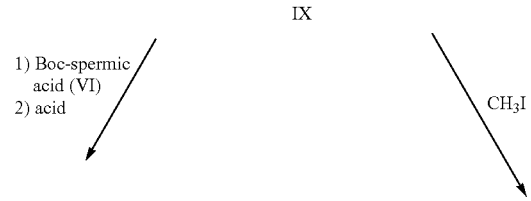
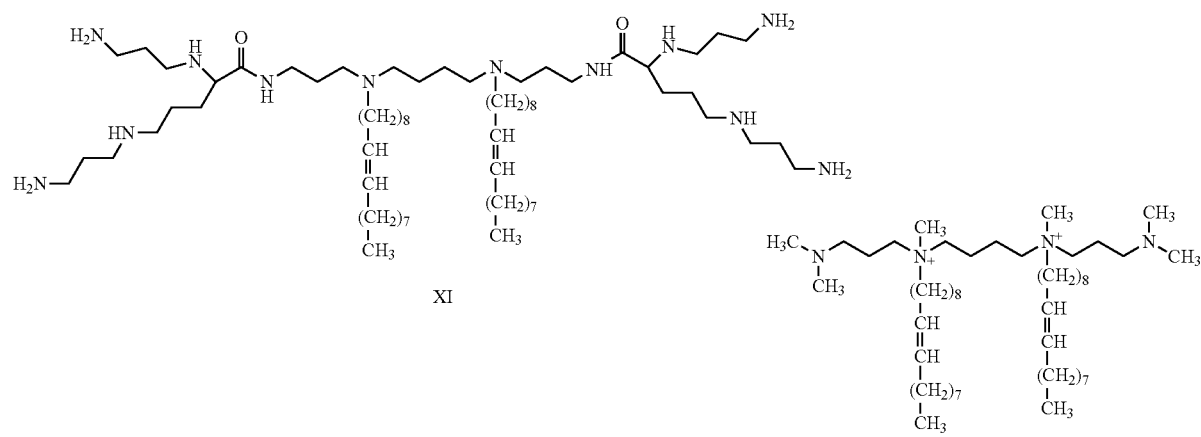

Example 3

Synthesis of Cholesterol Analogs

The cholesterol analogs can be synthesized by using the scheme given below (Scheme 3). Jeffamine is alkylated with cholestryl chloride to provide the dicholestryl jeffamine analog (XII). Further alkylation with the epoxide phthalamide (XIII) and deblocking with hydrazine gives the compound of the invention (XIV).

Synthesis of cholesterol analogs (Scheme 3)

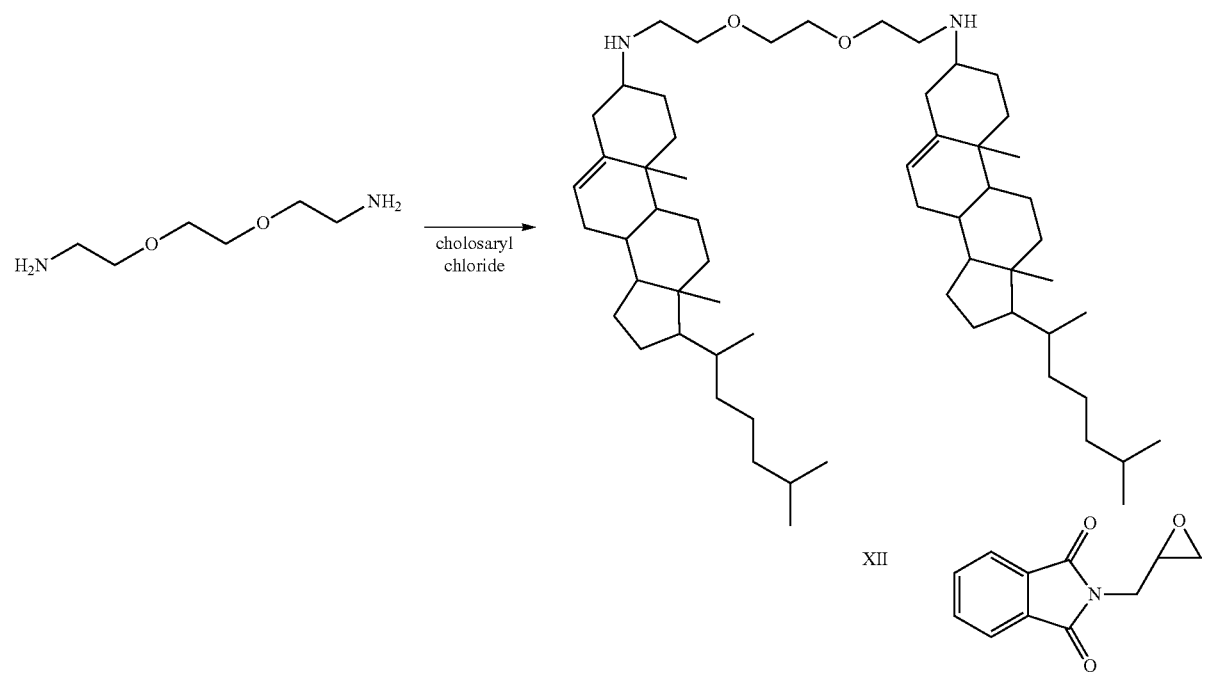

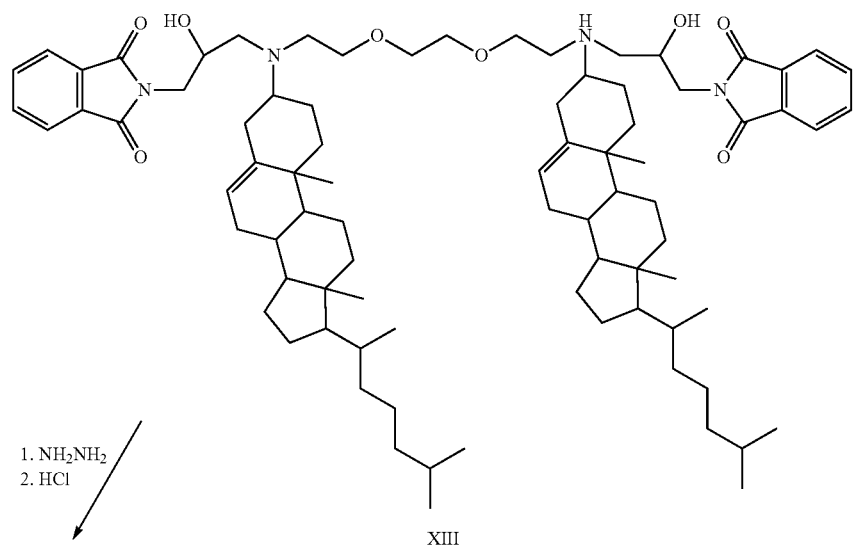

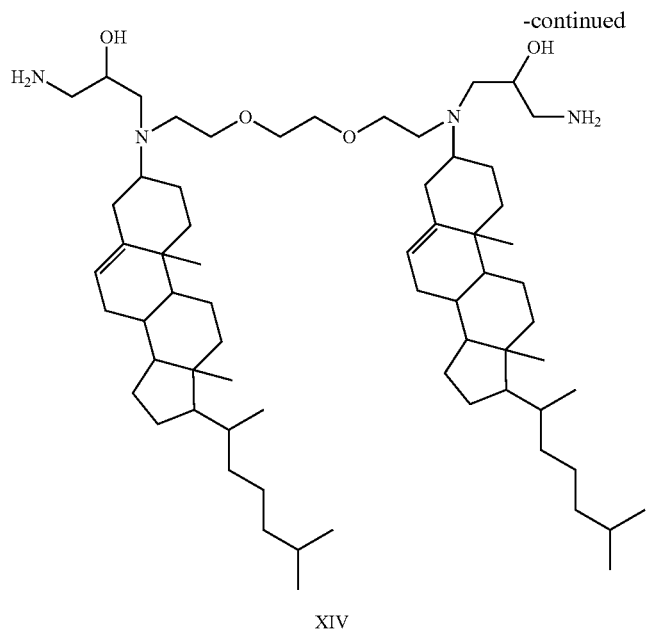

XIV

Example 4

Synthesis of Monoalkyl Analogs

When monoalkyl analogs are desired, the above Scheme 1 can be modified such that one of the amines in the starting material is protected before the acylation step. Thus, trityl-protected diaminobutane (XV) is acylated with alkanoyl chloride (e.g., oleoyl chloride) followed with LAH reduction to obtain compound XVIII. The amine is then alkylated with the desired phthalamide epoxide to obtain compound XVIII. Removing the phthalamide using hydrazine renders the desired amine XIX. (See Scheme 4).

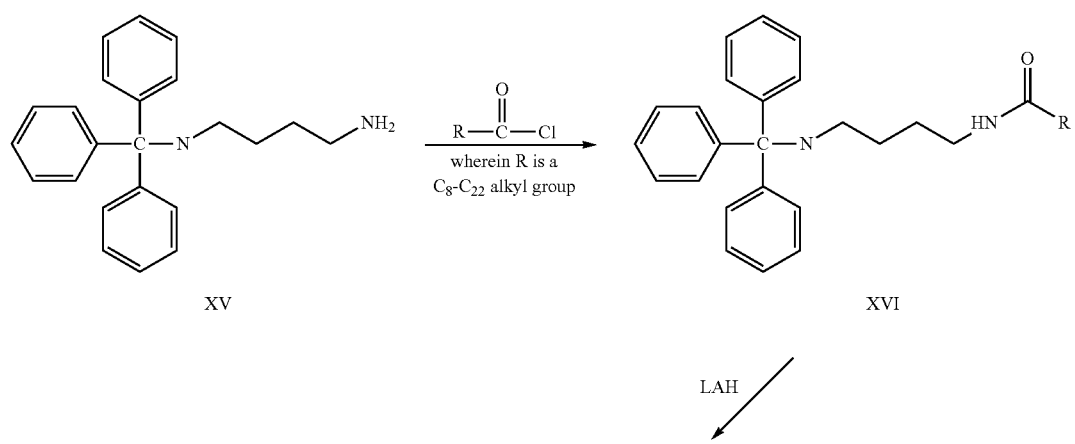

Synthesis of monoalkyl analogs (Scheme 4)

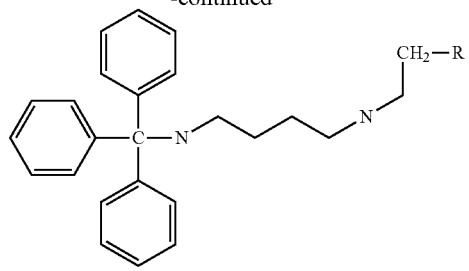

XVII

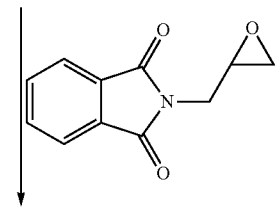

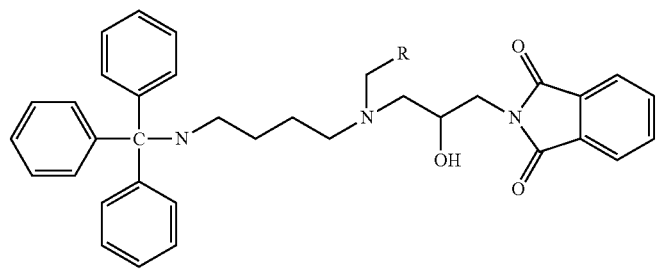

XVIII

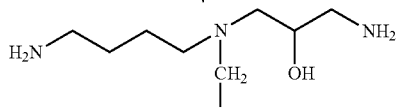

XIX

Example 5

Synthesis of Cyclic Analogs

The following scheme (Scheme 5) can be used to make the cyclic analogs. Trityl protected amino alcohol (XX) with the desired chain is alkylated using dibromoalkyl (e.g., dibromobutane). The trityl is removed from the desired dimer (XXI) and acylated using diacyl chlorides (e.g., succinyl chloride). The amide (XXIII) is then reduced with LAB and alkylated using the desired phthalamide epoxide. Removal of the phthalamide gives the desired compound of the invention.

Synthesis of cyclic analogs (Scheme 5):

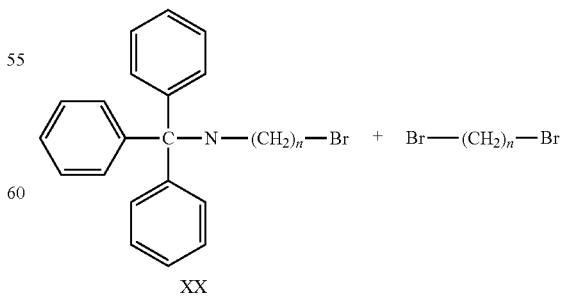

XX

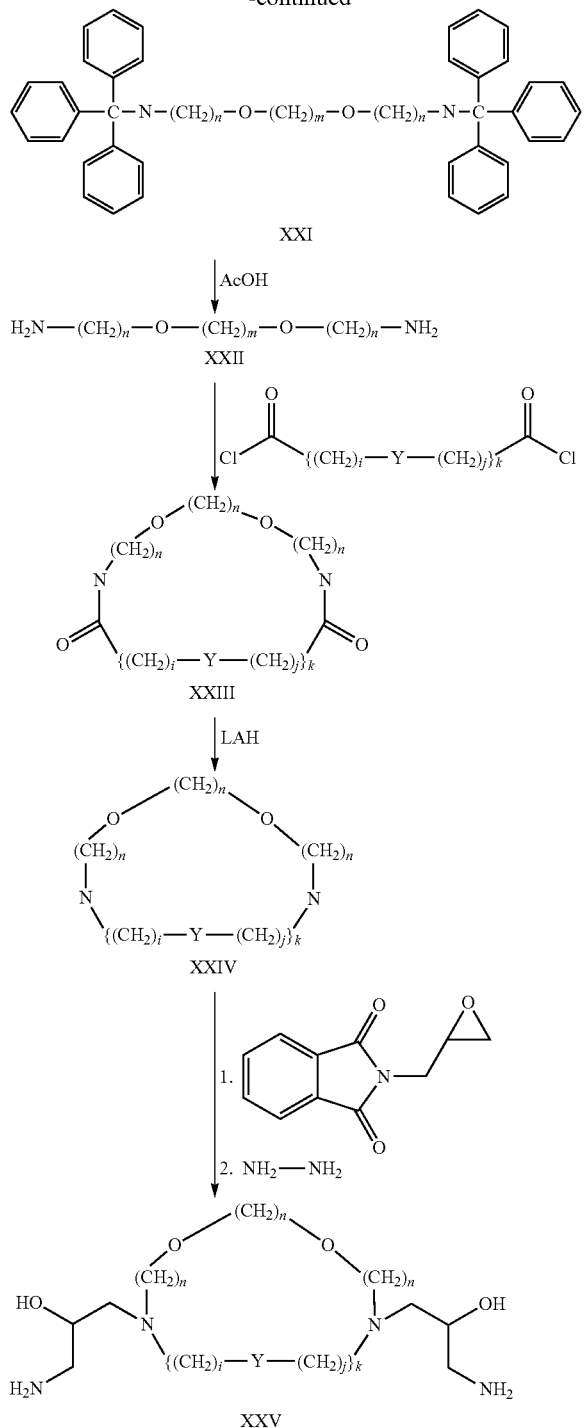

XXI wherein n = 8-22
m = 2-6
wherein i, j = 2-6
k = 1-2, and
Y = CH$_2$, O, S

Example 6

Synthesis of Polymeric Analogs

Polymeric analogs of the present invention can be synthesized by using polymeric amines such as PEI as starting material or dendrimeric polyamines. For example, PEI can be acylated with alkyloyl chloride (e.g., oleoyl chloride) and the acylated PEI can then be reduced with lithium aluminum hydride to obtain compounds of the invention.

Although the above methods exemplify the synthesis of specific compounds, the reaction schemes provide a general method for preparing a variety of compounds according to the present invention. Those of ordinary skill in the art will appreciate that alternate methods and reagents other than those specifically detailed herein can be employed or readily adapted to produce compounds of the invention.

The compounds of the present invention can be used in the same manner as are prior art compounds such as DOTMA, DOTAP, DOGS, DOSPA and the like. Methods for incorporating such cationic lipids into lipid aggregates are well-known in the art. Representative methods are disclosed by Felgner, et al., supra; Eppstein et al. supra; Behr et al. supra; Bangham, A. et al. (1965) M. Mol. Biol. 23:238 252; Olson, F. et al. (1979) Biochim. Biophys. Acta 557:9 23; Szoka, F. et al. (1978) Proc. Natl. Acad. Sci. USA 75:4194 4198; Mayhew, E. et al. (1984) Biochim. Biophys. Acta 775:169 175; Kim, S. et al. (1983) Biochim. Biophys. Acta 728: 339 348; and Fukunaga, M. et al. (1984) Endocrinol. 115:757 761. Techniques for preparing lipid aggregates of appropriate size for use as delivery vehicles include sonication and freeze-thaw plus extrusion as perhaps the most commonly used. See, e.g., Mayer, L. et al. (1986) Biochim. Biophys. Acta 858:161 168. Microfluidization is used when consistently small (50 200 nm) and relatively uniform aggregates are desired (Mayhew, E., supra). Aggregates ranging from about 50 nm to about 200 nm diameter are preferred; however, both larger and smaller sized aggregates are functional.

Methods of transfection and delivery of other compounds are well-known in the art. The compounds and compositions of the present invention yield lipid aggregates that can be used in the same processes used for other known transfection agents.

It will be readily apparent to those of ordinary skill in the art that a number of general parameters are important for optimal efficiency of transfection or delivery. These parameters include, for example, the cationic lipid concentration, the concentration of compound to be delivered, the number of cells transfected, the medium employed for delivery, the length of time the cells are incubated with the polyanion-lipid complex, and the relative amounts of cationic and non-cationic lipid. It may be necessary to optimize these parameters for each particular cell type. Such optimization is routine employing the guidance provided herein and knowledge generally available to the art.

It will also be apparent to those of ordinary skill in the art that alternative methods, reagents, procedures and techniques other than those specifically detailed herein can be employed or readily adapted to produce the liposomal precursors and transfection compositions of this invention. Such alternative methods, reagents, procedures and techniques are within the spirit and scope of this invention.

The use of representative compounds of the invention are further detailed by reference to the following examples. All abbreviations used herein are standard abbreviations in the art. Specific procedures not described in detail are either referenced or well-known in the art.

Example 7

This example compares transfection of HEK-293 (human embryonic kidney-derived cell line), COS-7 (SV40 transformed monkey cell line), CHO-KI (Chinese Hamster Ovaryderived cell line), and HeLa (Human cervical carcinoma-derived cell line) cells with the β-galactosidase reporter plasmid DNA pCMV SPORT-β-gal (Life Technologies, Rockville, Md.) using commercially available cationic lipid transfection reagents and the compounds of the present invention.

The cells were plated the day before transfection in 24-well tissue culture plates in a total volume of 0.4 ml DMEM (Dulbecco's Modified Eagle's Medium, Life Technologies, Rockville, Md.) culture medium containing a 1% non-essential amino acid (NEAA) solution (LifeTechnologies), and 10% FBS. For the HEK-293 and COS-7 cells, tissue culture plates were pre-coated with Poly-L-Lysine to enhance cell attachment.

The next day, DNA-transfection reagent complexes were prepared as follows:

The cationic lipid reagents and DNA were diluted separately into 25.mu.l aliquots of serum-free DMEM, containing 1% NEAA. For LIPOFECTAMINE® PLUS, 7 14 μl of PLUS reagent was added to the DNA, mixed, and incubated for 15 minutes at room temperature. The diluted DNA was combined with the diluted lipid and incubated at room temperature for at least 15 minutes to allow the DNA and the lipid to form complexes. Following this incubation the complexes were added directly into the culture medium dropwise and mixed by rocking the culture plate back and forth. The cells were further incubated at 37° C. for a total of 24 hours to allow expression of the lacZ transgene encoded by the reporter plasmid, pCMV SPORT-β-gal. At 24 hours post-transfection, the growth medium and transfection complexes were removed from the wells, and the cells in each well were rinsed briefly with 1 ml of D-PBS (Dulbecco's PBS, Life Technologies, Rockville, Md.). The cells in each well were lysed by the addition of 0.15 to 2.0 ml of 0.1% Tris, pH 8.0, containing 0.1 M Triton X-100. The plates were frozen at −80° C. for a minimum of 2 hours, and thawed at room temperature or 37° C. The thawed cell lysates were cleared by centrifugation and the supernatants were assayed for β-gal activity using the enzymatic substrate ONPG. The concentration of total protein in cell lysates was also determined using a Bradford assay (Bio-Rad Laboratories, Hercules Calif.). β-gal activity in transfected cell extracts was calculated against a standard curve and expressed as ng β-gal per surface area of tissue culture plate (ng/cm2) to reflect activity per transfection, or as ng β-gal per μg of total protein (ng/μg) to reflect specific activity.

Figure 2:
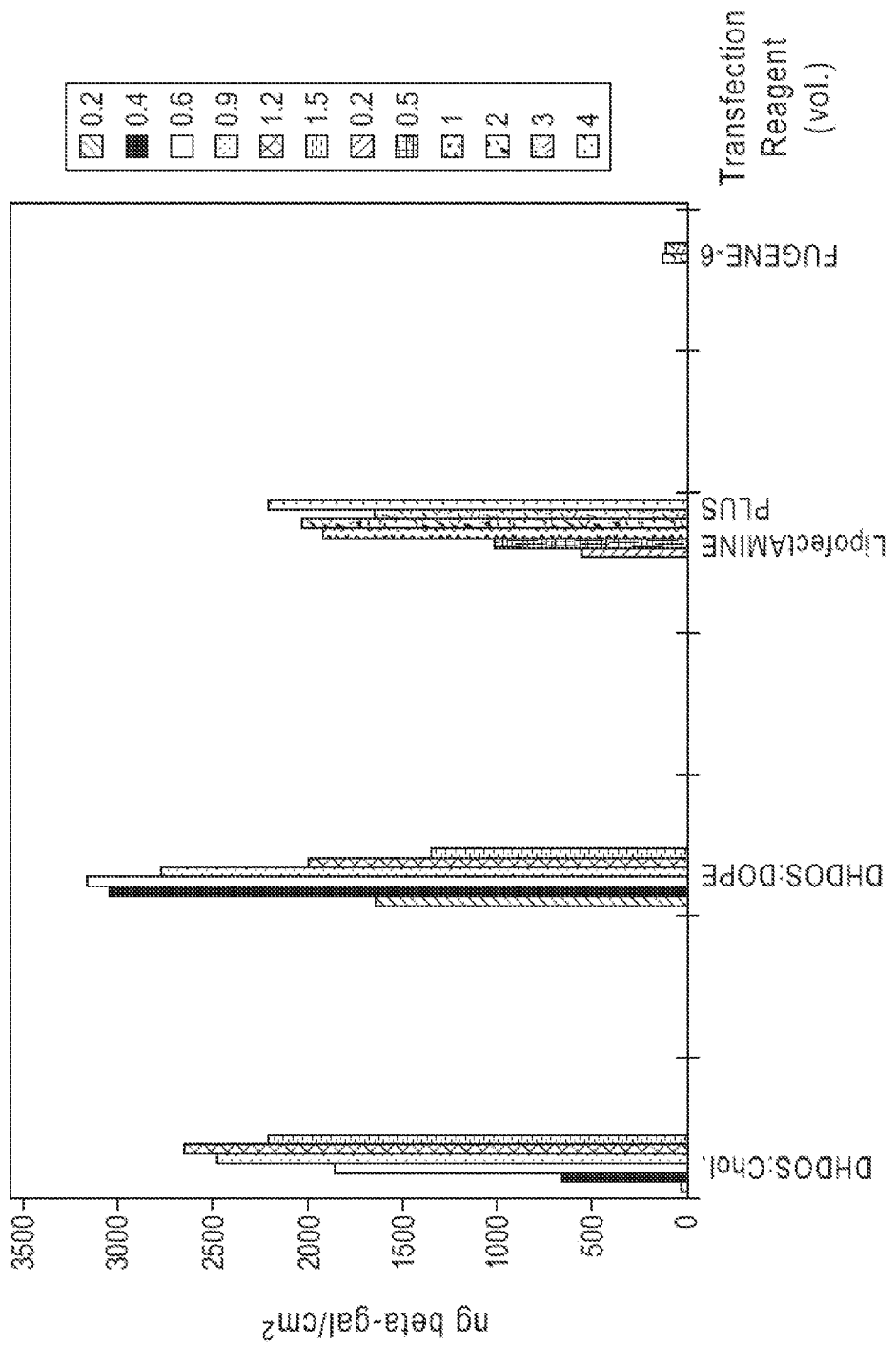
FIG. 2 is a graph showing transfection of COS-7 cells with cationic transfection reagents.
Figure 3:
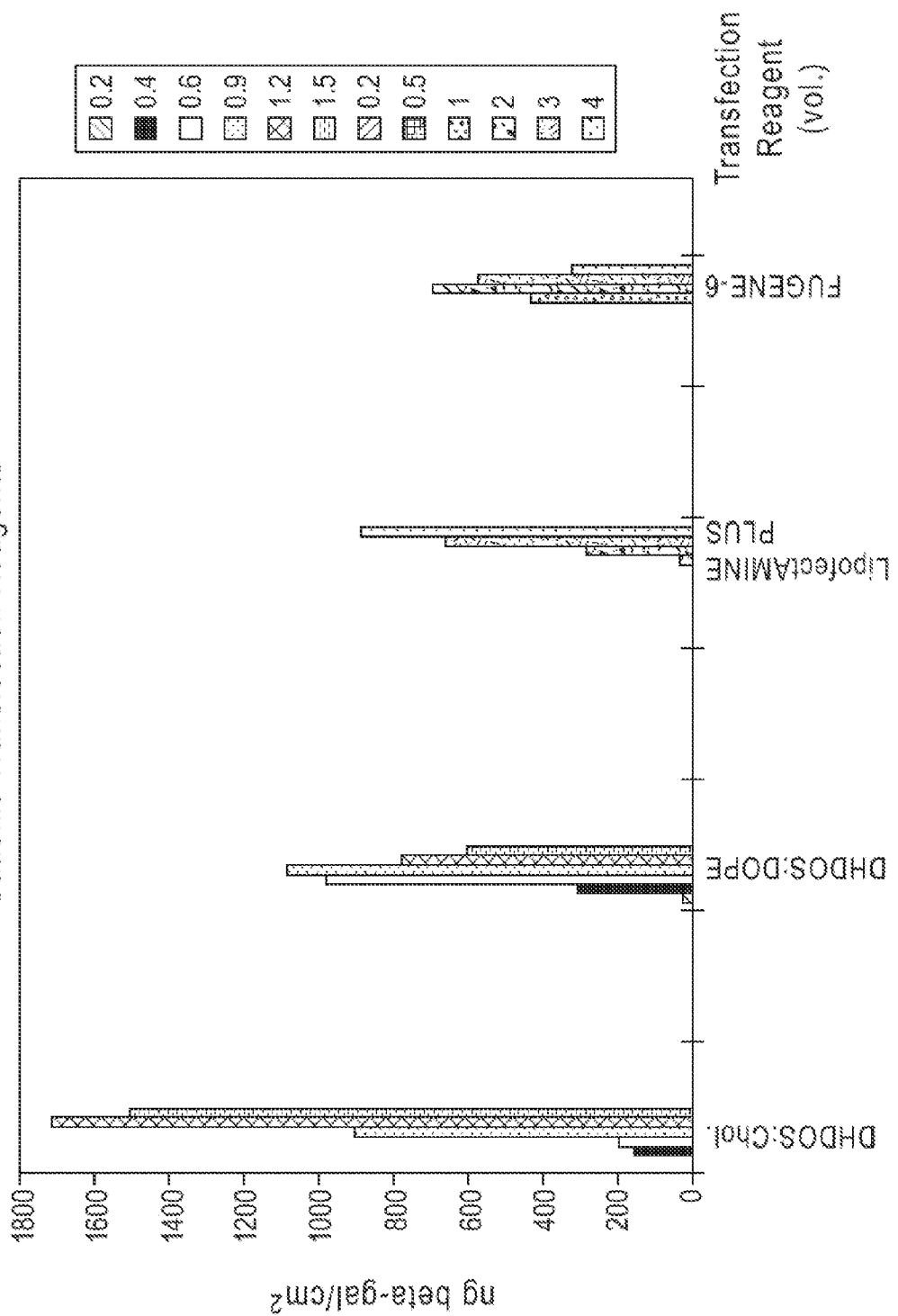
FIG. 3 is a graph showing transfection of CHO-KI cells with cationic transfection reagents.
Figure 4:
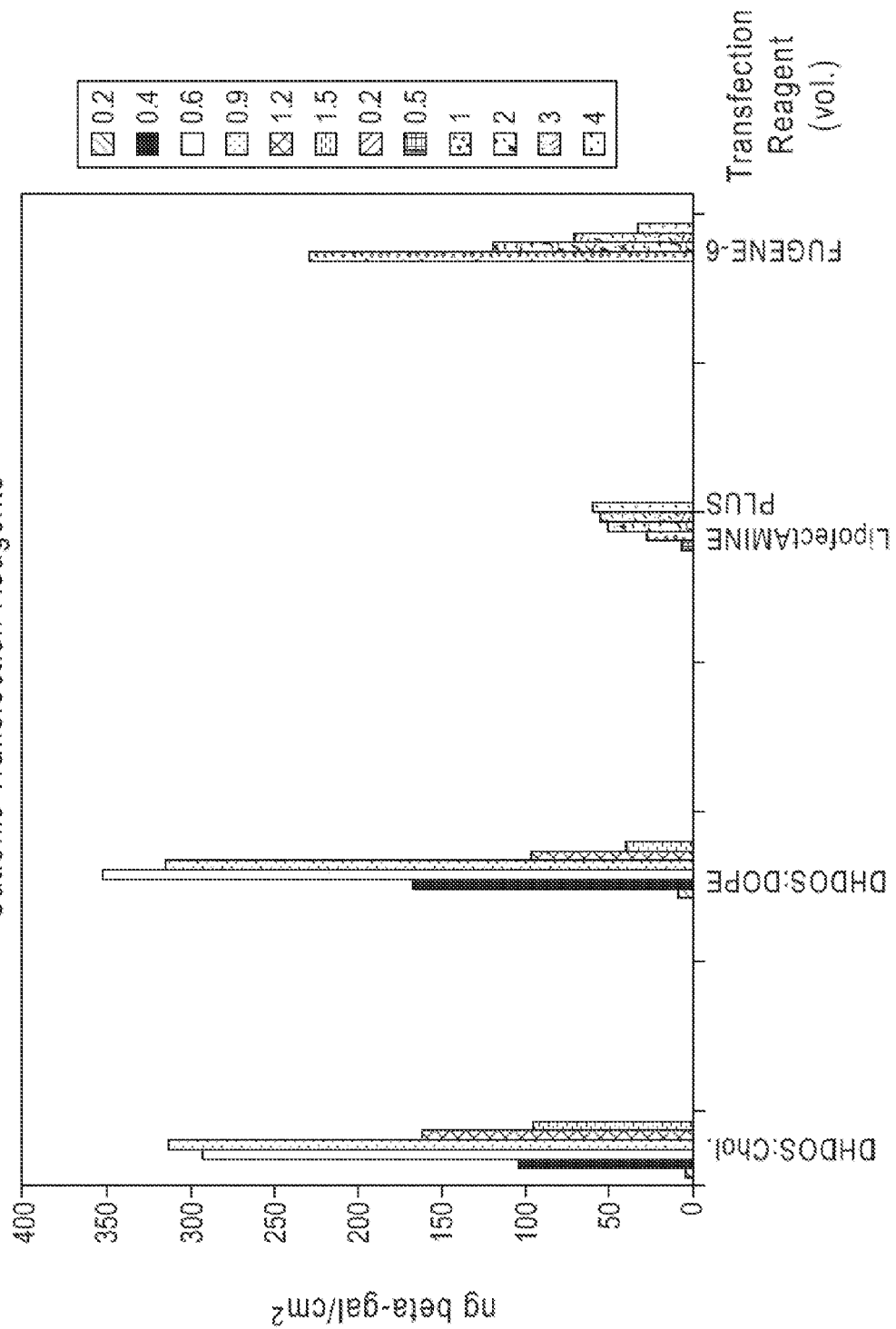
FIG. 4 is a graph showing transfection of He La cells with cationic transfection reagents.

HEK-293 (FIG. 1), COS-7 (FIG. 2), CHO-KI (FIG. 3), and HeLa (FIG. 4) cells were transfected with 0.4 or 0.8 μg of pCMV SPORT-β-gal DNA and 0.2 to 4.0 μl of transfection reagent. The transfection reagents tested were DHDOS (IV) formulated at 2 mg/ml with the neutral co-lipid, cholesterol (at a ratio of 1:15 (M/M) DHDOS to cholesterol); DHDOS formulated at 2 mg/ml with the neutral co-lipid DOPE (dioleylphosphatidyl ethanolamine) (at a ratio of 1:1 (M/M) DHDOS to DOPE); LIPOFECTAMINE® PLUS (Life Technologies, Rockville Md.); and FuGENE™-6 (Boehringer Mannheim, Germany). DHDOS formulations were tested in the range of 0.2 to 1.5 μl; LIPOFECTAMINE® PLUS and FuGENE-6 were tested in the range of 0.2 to 4.0 μl. FuGENE-6 was used according to the manufacturer's recommended protocol. DHDOS and LIPOFECTAMINE® PLUS were used according to the above protocol. The data presented in the Figures are expressed as total activity (ng/cm$^2$) to better compare total expression from the transfected DNA. Only data with 0.8 μg of DNA is shown, since similar results were obtained with 0.4 and 0.8 μg of DNA.

Example 8

Primary, passaged, normal human fibroblasts (NHFs) were plated in 96-well plates at a density of 1.6.times.104 cells per well and transfected the following day. Cells in each well were transfected with 40 ng pCMV SPORT-β-gal DNA and 0.1 or 0.2 μl lipid.

The DNA and lipid were diluted separately into 10 μl of DMEM. The DNA was either used alone or pre-mixed with PLUS, insulin, transferrin, or an integrin-targeting peptide prior to complexing with the lipid. After 15 minutes of complexing, the DNA-lipid was added to cells. Cells were assayed for p-gal activity as described above.

| | ACTIVITY (ng/βgal/cm$^2$) | | | | |
|---|---|---|---|---|---|
| LIPID | DNA | DNA and PLUS | DNA and INSULIN | DNA and TRANSFERRIN | DNA and INTEGRIN-TARGETING PRPTIDE |
| LipofectAMINE | 10.36 | 28.6 | ND | 17.4 | ND |
| Compound of Formula X 1:1.5 DOPE 1 mg/ml | ND | 37.5 | ND | ND | 40.9 |
| Compound of Formula VII 2 mg/ml | 29.4 | 637.9 | 195.7 | 21.7 | 587.9 |

ND = no detectable activity
*PLUS Reagent is available from Life Technologies, Inc., Rockville, Maryland
**Reference: S.L. HART, et al (1998), Human Gene Therapy, 9: 575-585

The results show that these cationic lipid formulations can deliver DNA molecules alone, but also that delivery, and ultimately gene expression, may be enhanced when the lipids are used in conjunction with peptides or proteins that bind DNA and/or act as ligands for cell surface receptors, or otherwise enhance cellular and/or nuclear uptake.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

We claim:

1. A transfection complex formed in an aqueous medium, said transfection complex comprising:
    an expressible nucleic acid;
    a compound having the structure:

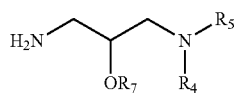

or a polycation thereof;
    wherein $R_4$ is a straight-chain, branched or cyclic, alkyl or alkenyl group having 8 to 24 carbon atoms, $R_5$ is an alkyl group substituted with one or more amines and one or more alcohols, and $R_7$ is H or a carbohydrate; and
    at least one protein or peptide transfection enhancer.

2. The transfection complex according to claim 1, wherein the protein or peptide transfection enhancer enhances cell-targeting, uptake, internalization, nuclear targeting or expression of the expressible nucleic acid.

3. The transfection complex according to claim 1, wherein the protein or peptide transfection enhances uptake of the expressible nucleic acid.

4. The transfection complex according to claim 1, wherein $R_5$ is an alkyl group substituted with one amine and one or more alcohols.

5. The transfection complex according to claim 1, wherein the amine substituent of the $R_5$ alkyl group comprises an aminoethanol, an aminopropanol or an aminobutanol group.

6. The transfection complex according to claim 5, wherein the amine substituent of the $R_5$ alkyl group has the structure:

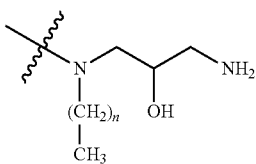

wherein n is an integer from 7-23.

7. The transfection complex according to claim 1, wherein $R_5$ is an alkyl group having 3-30 carbon atoms and is substituted by one amine and one or more alcohols.

8. The transfection complex according to claim 7, wherein the amine substituent of the $R_5$ alkyl group comprises an aminoethanol, an aminopropanol or an aminobutanol group.

9. The transfection complex according to claim 7, wherein the amine substituent of the $R_5$ alkyl group has the structure:

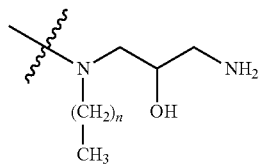

wherein n is an integer from 7-23.

10. The transfection complex according to claim 2, wherein the protein or peptide transfection enhancer enhances uptake, internalization or nuclear targeting of the expressible nucleic acid.

11. The transfection complex according to claim 10, wherein the amine substituent of the $R_5$ alkyl group has the structure:

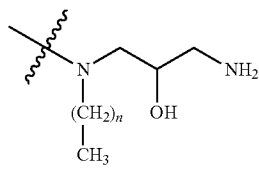

wherein n is an integer from 7-23.

12. The transfection complex according to claim 1, wherein $R_7$ is H.

13. The transfection complex according to claim 12, wherein $R_4$ is a straight-chain alkyl group having 8 to 24 carbon atoms.

14. The transfection complex according to claim 13, wherein $R_5$ is an alkyl group having 3-30 carbon atoms and is substituted with one amine and one or more alcohols.

15. The transfection complex according to claim 14, wherein the amine substituent of the $R_5$ alkyl group comprises an aminoethanol, an aminopropanol or an aminobutanol group.

16. The transfection complex according to claim 14, wherein the amine substituent of the $R_5$ alkyl group has the structure:

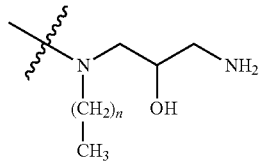

wherein n is an integer from 7-23.

17. The transfection complex according to claim 14, wherein $R_5$ is a propyl or a butyl group which is substituted by one amine and one or more alcohols.

18. The transfection complex according to claim 17, wherein the amine substituent of the $R_5$ alkyl group comprises an aminoethanol, an aminopropanol or an aminobutanol group.

19. The transfection complex according to claim 18, wherein the amine substituent of the $R_5$ alkyl group has the structure:

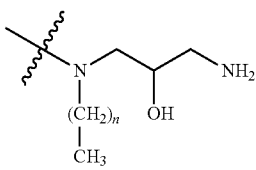

wherein n is an integer from 7-23.

20. The transfection complex according to claim 1, wherein $R_4$ is a Straight-chain alkyl group having 8 to 24 carbon atoms, $R_5$ is a butyl group substituted with one amine and one or more alcohols, and $R_7$ is H.

21. The transfection complex according to claim 20, wherein the amine substituent of the $R_5$ alkyl group comprises an aminoethanol, an aminopropanol or an aminobutanol group.

22. The transfection complex according to claim 21, wherein the amine substituent of the $R_5$ alkyl group has the structure:

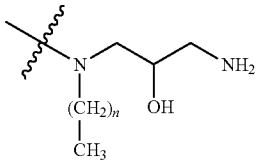

wherein n is an integer from 7-23.

23. The transfection complex according to claim 1, wherein $R_4$ is a straight-chain alkyl group having 8 to 24 carbon atoms, $R_5$ is a propyl group substituted with one amine and one alcohol, and $R_7$ is H.

24. The transfection complex according to claim 23, wherein the amine substituent of the $R_5$ alkyl group comprises an aminoethanol, an aminopropanol or an aminobutanol group.

25. The transfection complex according to claim 24, wherein the amine substituent of the $R_5$ alkyl group has the structure:

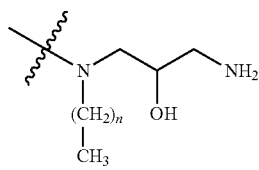

wherein n is an integer from 7-23.

26. The transfection complex according to claim 1, wherein the transfection complex further comprises one or more neutral lipids.

27. The transfection complex according to claim 26, wherein the neutral lipid is DOPE, DOPC or cholesterol.

28. The transfection complex according to claim 1, wherein the transfection complex comprises a liposome.

* * * * *